US007300749B2

(12) United States Patent
Bertin et al.

(10) Patent No.: US 7,300,749 B2
(45) Date of Patent: Nov. 27, 2007

(54) MOLECULES OF THE PYRIN DOMAIN PROTEIN FAMILY AND USES THEREOF

(75) Inventors: John Bertin, Watertown, MA (US); Gulam A. Manji, Pacifica, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 508 days.

(21) Appl. No.: 10/127,516

(22) Filed: Apr. 22, 2002

(65) Prior Publication Data

US 2002/0187922 A1  Dec. 12, 2002

Related U.S. Application Data

(63) Continuation-in-part of application No. 10/027,629, filed on Dec. 20, 2001, now abandoned, which is a continuation-in-part of application No. 09/964,955, filed on Sep. 26, 2001, now abandoned, which is a continuation-in-part of application No. 09/653,901, filed on Sep. 1, 2000, now abandoned, which is a continuation-in-part of application No. 09/506,067, filed on Feb. 17, 2000, now abandoned.

(51) Int. Cl.
*C12Q 1/00* (2006.01)
*G01N 33/53* (2006.01)

(52) U.S. Cl. .............................. 435/4; 435/7.1; 435/7.2; 435/7.8

(58) Field of Classification Search ...................... 435/4
See application file for complete search history.

(56) References Cited

U.S. PATENT DOCUMENTS 6,953,691 B2 * 10/2005 Reed et al. ................. 435/325
2003/0077699 A1 4/2003 Reed et al.

FOREIGN PATENT DOCUMENTS

| WO | WO 99/46290 A1 | 9/1999 |
| WO | WO 01/23402 A1 | 4/2001 |
| WO | WO 01/30971 A2 | 5/2001 |
| WO | WO 01/30971 A3 | 5/2001 |
| WO | WO 03/031639 * | 4/2003 |

OTHER PUBLICATIONS

Grenier et al, FEBS Letters, 2002, vol. 530, pp. 73-78.*
Centola et al, Blood, 2000, vol. 95, pp. 3223-3231.*
Burgess et al. (Journal of Cell Bio. 111:2129-2138, 1990).*
Lazar et al. Molecular and Cellular Biology 8:1247-1252 (1988).*
Bork (Genome Research, 2000, 10:398-400).*
Ibragimova and Eade (Biophysical Journal, Oct. 1999, vol. 77, pp. 2191-2198).*
Hofmann, K. et al., "The Card Domain: a New Apoptotic Signalling Motif", Trends in Biochemical Sciences, 22:155-156, (1997).
Imai, Y. et al., "The CED-4-Homologous Protein FLASH Is Involved In Fas-Mediated Activation of Caspase-8 During Apoptosis", Nature, 398:777-784, (1999).

Nicholson, D.W., "Caspase Structure, Proteolytic Substrates, and Function During Apoptotic Cell Death", Cell Death and Differentiation, 6:1028-1042, (Apr. 29, 1999).
Schwandner, R. et al., "Peptidoglycan-and Lipoteichoic Acid-induced Cell Activation Is Mediated by Toll-like Receptor 2" Journal of Biological Chemistry 274(25):17406-17409 (Jun. 18, 1999).
Van der Biezen, E.A. and Jones, J.D.G. "The NB-ARC domain: a novel signaling motif shared by plant resistance gene products and regulators of cell death in animals" Current Biology, 8(7):R226-R227, Mar. 26, 1998.
Yang, R.B. et al., "Signaling events induced by lipopolysaccharide-activated toll-like receptor 2" Journal of Immunology 163(2):639-43 (Jul. 15, 1999).
Yang, R.B. et al., "Toll-like receptor-2 mediates lipopolysaccharide-induced cellular signalling" Nature 395(6699):284-288 (Sep. 17, 1998).
Yoshimura, A. et al., "Cutting Edge: Recognition of Gram-Positive Bacterial Cell Wall Components by the Innate Immune System Occurs Via Toll-Like Receptor 2" Journal of Immunology, 163(1):1-5 (1999).
Bertin, J. and DiStefano, P.S., "The PYRIN domain: a novel motif found in apoptosis and inflammation proteins" Cell Death and Differentiation 7:1273-1274 (2000).
Mao, M., et al., angiotensin/vasopressin receptor AII/AVP [Homo sapiens], May 22, 2001 (sequence) GenBank [online] Bethesda, MD, USA: National Center for Biotechnology Information [retrieved on May 27, 2001] Retrieved from the Internet: URL: http://www.ncbi.nlm.nih.gov/>. GenBank Accession No. AAC39910.
Tong, Z.B. and Nelson, L.M., MATER Protein [Mus musculus], May 10, 2000 (sequence) GenBank [online] Bethesda, MD, USA: National Center for Biotechnology Information [retrieved on Sep. 9, 2002] Retrieved from the Internet: URL: http://www.ncbi.nlm.nih.gov/>. GenBank Accession No. AAD51762.
Mao, M., et al., Homo sapiens angiotensin/vasopressin receptor AII/AVP mRNA, complete cds, May 22, 2001 (sequence) GenBank [online] Bethesda, MD, USA: National Center for Biotechnology Information [retrieved on May 27, 2001] Retrieved from the Internet: URL: http://www.ncbi.nlm.nih.gov/>. GenBank Accession No. AF054176.
Watanabe, K., et al., Homo sapiens cDNA FLJ20510 fis, clone KAT09662, Feb. 22, 2000 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AK000517.

(Continued)

*Primary Examiner*—Karen A. Canella

(57) ABSTRACT

Diagnostic, screening and therapeutic methods utilizing NBS-1 and PYRIN-1 are disclosed. The methods take advantage of the interactions between NBS-1 or PYRIN-1 and various proteins involved in apoptotic and inflammatory signaling pathways. Also disclosed are methods for identifying modulators of ASC and NF-κB.

34 Claims, 32 Drawing Sheets

OTHER PUBLICATIONS

Bird, C., Human DNA sequence from clone RP1-154J13 on chromosome Xq26.1-26 Contains STSs and a GSS, complete sequence, Jan. 11, 2000 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AL049734.

Strausberg, R., hd29b11.x1 Soares_NFL_T_GBC_S1 Homo sapiens cDNA clones IMAGE:29109093', mRNA sequence, Feb. 24, 2000 (sequence) GenBank [online]Bethesda, MD, USA: National Center for Biotechnology Information [retrieved on May 27, 2001] Retrieved from the Internet: URL: http://www.ncbi.nlm.nih.gov/>. GenBank Accession No. AW468866.

Macke, J. et al., 70G12 Human retina cDNA Tsp5091-cleaved sublibrary Homo sapiens cDNA not directional, mRNA sequence, May 6, 1996 (sequence) GenBank [online Sep. 9, 2002] Bethesda, MD, USA: National Center for Biotechnology Information [retrieved on May 15, 2000] Retrieved from the Internet: URL: http://www.ncbi.nlm.nih.gov/>. GenBank Accession No. W22630.

Baker, B. et al., "Signaling in Plant-Microbe Interactions," Science 276:726-733 (May 2, 1997).

Bertin, J. et al., "Human CARD4 Protein Is a Novel CED-4/Apaf-1 Cell Death Family Member That Activates NF-kB", Journal of Biological Chemistry 274(19):12955-12958 (May 7, 1999).

Booth, D.R. et al.,"Pyrin/marenostrin mutations in familial Mediterranean fever," Quarterly Journal of Medicine 91(9)603-606 (Sep. 1998).

Hillier, L., et al. zq69all.c1 stratagene neuroepithelium (#937231) Homo sapiens cDNA clone IMAGE: 646844 5' similar to SW:RINI_PIG P10775 Ribonuclease Inhibitor. mRNA sequence, Jan. 27, 1997 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AA205674.

Hillier, L., et al. zq68g11.r1 Stratagene neuroepithelium (#937231) Homo sapiens cDNA clone IMAGE: 646820 51 similar to SW:RINI_RAT P29315 Ribonuclease Inhibitor mRNA sequence, Jan. 27, 1997 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AA205775.

Adams, M.D., et al. EST94433 Activated T-cells I Homo sapiens cDNA 5' end, mRNA sequence, Apr. 21, 1997 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AA381361.

Hillier, L., et al., af75h01.r1 Soares_NhHMPu_S1 Homo sapiens cDNA clone IMAGE: 1047889 5' similar to SW:RINI_RAT P29315 Robonuclease Inhibitor mRNA sequence, Jan. 29, 1998 (sequence) GenBank [online] Bethesda, MD, USA: National Center for Biotechnology Information [retrieved on May 15, 2000] Retrieved from the Internet: URL: http://www.ncbi.nlm.nih.gov/>. GenBank Accession No. AA773929.

Masumoto, J. et al., "ASC, a Novel 22-kDa Protein, Aggregates during Apoptosis of Human Promyelocytic Leukemia HL-60 Cells" Journal of Biological Chemistry 274(48):33835-33838 (Nov. 26, 1999).

Zhang, Q., et al., CBDAKD01 coding sequence Nov. 26, 1999 (sequence) GenBank [online] Bethesda, MD, USA: National Center for Biotechnology Information [retrieved on Sep. 9, 2002] Retrieved from the Internet: URL: http://www.ncbi.nlm.nih.gov/>. GenBank Accession No. AAZ20641.

DOE Joint Genome Institute and Stanford Human Genome Center Homo sapiens chromosome 19 clone CTC-550B14 *sequencing in progress* , 2 ordered pieces, Oct. 8, 1999 (sequence) GenBank [online] Bethesda, MD, USA: National Center for Biotechnology Information [retrieved on Sep. 9, 2002] Retrieved from the Internet: URL: http://www.ncbi.nlm.nih.gov/>. GenBank Accession No. AC011476.

Birren, B., et al., "Homo sapiens chromosome 18, clone RP11-482N10 map18, Low Pass sequence Sampling", Feb. 15, 2000 GenBank [online] Bethesda, MD, USA: National Center for Biotechnology Information [retrieved on Sep. 9, 2002] Retrieved from the Internet: URL: http://www.ncbi.nlm.nih.gov/>. GenBank Accession No. AC023386.

Manji, G.A., et al., "PYPAF1, a PYRIN-containing APafl-like Protein that assembles with ASC and regulates activation of NF-kB" Journal of Biological Chemistry, vol. 277, Issue 13, 11570-11575, Mar. 29, 2002.

Wang, L., et al., "CARD10 is a Novel caspase recruitment domain/membrane-associated guanylate kinase family member that interacts with BCL10 and Activates NF-kB" Journal of Biological Cheministry, vol. 276, Issue 24, 21405-21409, Jun. 15, 2001.

Bertin, J., et al., "CARD11 and CARD 14 are Novel caspase recruitment domain (CARD)/Membrane-associated guanylate kinase (MAGUK) family members that interact with BCL10 and Activate NF-kB" Journal of Biological Chemistry, vol. 276, Issue 15, 11877-11882, Apr. 13, 2001.

* cited by examiner

```
CAGCCCTCAT CTCCGCCGGC GAGTAGGGCC AGGTGTTGGG AGCTCCCACG TGGGACAAGG    60
TGGTGTCTTC GGCGCAG                                                   77
```

| | | | | | | | | | | | | | | | | |
|---|---|---|---|---|---|---|---|---|---|---|---|---|---|---|---|---|
| atg | ggt | ttc | aac | ctg | cag | gct | ctc | ctg | gag | cag | ctc | agc | cag | gat | gag | 125 |
| Met | Gly | Phe | Asn | Leu | Gln | Ala | Leu | Leu | Glu | Gln | Leu | Ser | Gln | Asp | Glu | |
| 1 | | | | 5 | | | | | 10 | | | | | 15 | | |

| ttg | agc | aag | ttc | aag | tat | ctg | atc | acg | acc | ttc | tcc | ccg | gca | cac | gag | 173 |
|---|---|---|---|---|---|---|---|---|---|---|---|---|---|---|---|---|
| Leu | Ser | Lys | Phe | Lys | Tyr | Leu | Ile | Thr | Thr | Phe | Ser | Pro | Ala | His | Glu | |
| | | | 20 | | | | | 25 | | | | | 30 | | | |

| ctc | cag | aag | atc | ccc | cac | aag | gag | gta | gac | aag | gct | gat | ggg | aag | caa | 221 |
|---|---|---|---|---|---|---|---|---|---|---|---|---|---|---|---|---|
| Leu | Gln | Lys | Ile | Pro | His | Lys | Glu | Val | Asp | Lys | Ala | Asp | Gly | Lys | Gln | |
| | | 35 | | | | | 40 | | | | | 45 | | | | |

| ctg | gta | gaa | atc | ctc | acc | acc | cat | tgt | gac | agc | tac | tgg | gtg | gag | atg | 269 |
|---|---|---|---|---|---|---|---|---|---|---|---|---|---|---|---|---|
| Leu | Val | Glu | Ile | Leu | Thr | Thr | His | Cys | Asp | Ser | Tyr | Trp | Val | Glu | Met | |
| | 50 | | | | | 55 | | | | | 60 | | | | | |

| gcg | agc | ctc | cag | gtc | ttt | gaa | aag | atg | cac | cga | atg | gat | ctg | tct | gag | 317 |
|---|---|---|---|---|---|---|---|---|---|---|---|---|---|---|---|---|
| Ala | Ser | Leu | Gln | Val | Phe | Glu | Lys | Met | His | Arg | Met | Asp | Leu | Ser | Glu | |
| 65 | | | | 70 | | | | | 75 | | | | | 80 | | |

| aga | gca | aag | gat | gaa | gtc | aga | gaa | gca | gct | ttg | aaa | tcc | ttt | aat | aaa | 365 |
|---|---|---|---|---|---|---|---|---|---|---|---|---|---|---|---|---|
| Arg | Ala | Lys | Asp | Glu | Val | Arg | Glu | Ala | Ala | Leu | Lys | Ser | Phe | Asn | Lys | |
| | | | | 85 | | | | | 90 | | | | | 95 | | |

| agg | aag | cct | cta | tca | tta | ggg | ata | aca | cgg | aaa | gaa | cga | cca | cct | cta | 413 |
|---|---|---|---|---|---|---|---|---|---|---|---|---|---|---|---|---|
| Arg | Lys | Pro | Leu | Ser | Leu | Gly | Ile | Thr | Arg | Lys | Glu | Arg | Pro | Pro | Leu | |
| | | | 100 | | | | | 105 | | | | | 110 | | | |

| gac | gtg | gac | gaa | atg | ctg | gag | cgc | ttc | aaa | aca | gaa | gca | caa | gac | aaa | 461 |
|---|---|---|---|---|---|---|---|---|---|---|---|---|---|---|---|---|
| Asp | Val | Asp | Glu | Met | Leu | Glu | Arg | Phe | Lys | Thr | Glu | Ala | Gln | Asp | Lys | |
| | | 115 | | | | | 120 | | | | | 125 | | | | |

| gac | aat | agg | tgc | agg | tat | ata | ttg | aag | acg | aag | ttc | cgg | gag | atg | tgg | 509 |
|---|---|---|---|---|---|---|---|---|---|---|---|---|---|---|---|---|
| Asp | Asn | Arg | Cys | Arg | Tyr | Ile | Leu | Lys | Thr | Lys | Phe | Arg | Glu | Met | Trp | |
| | 130 | | | | | 135 | | | | | 140 | | | | | |

| aag | agc | tgg | cct | gga | gat | agc | aaa | gag | gtc | cag | gtt | atg | gct | gag | aga | 557 |
|---|---|---|---|---|---|---|---|---|---|---|---|---|---|---|---|---|
| Lys | Ser | Trp | Pro | Gly | Asp | Ser | Lys | Glu | Val | Gln | Val | Met | Ala | Glu | Arg | |
| 145 | | | | 150 | | | | | 155 | | | | | 160 | | |

| tac | aag | atg | ctg | atc | cca | ttt | agc | aac | ccc | agg | gtg | ctt | ccc | ggg | ccc | 605 |
|---|---|---|---|---|---|---|---|---|---|---|---|---|---|---|---|---|
| Tyr | Lys | Met | Leu | Ile | Pro | Phe | Ser | Asn | Pro | Arg | Val | Leu | Pro | Gly | Pro | |
| | | | | 165 | | | | | 170 | | | | | 175 | | |

| ttc | tca | tac | acg | gtg | gtg | ctg | tat | ggt | cct | gca | ggc | ctt | ggg | aaa | acc | 653 |
|---|---|---|---|---|---|---|---|---|---|---|---|---|---|---|---|---|
| Phe | Ser | Tyr | Thr | Val | Val | Leu | Tyr | Gly | Pro | Ala | Gly | Leu | Gly | Lys | Thr | |
| | | | 180 | | | | | 185 | | | | | 190 | | | |

| acg | ctg | gcc | cag | aaa | cta | atg | cta | gac | tgg | gca | gag | gac | aac | ctc | atc | 701 |
|---|---|---|---|---|---|---|---|---|---|---|---|---|---|---|---|---|
| Thr | Leu | Ala | Gln | Lys | Leu | Met | Leu | Asp | Trp | Ala | Glu | Asp | Asn | Leu | Ile | |
| | 195 | | | | | 200 | | | | | 205 | | | | | |

FIG. 1A

```
cac aaa ttc aaa tat gcg ttc tac ctc agc tgc agg gag ctc agc cgc    749
His Lys Phe Lys Tyr Ala Phe Tyr Leu Ser Cys Arg Glu Leu Ser Arg
    210                 215                 220 ctg ggc ccg tgc agt ttt gca gag ctg gtc ttc agg gac tgg cct gaa    797
Leu Gly Pro Cys Ser Phe Ala Glu Leu Val Phe Arg Asp Trp Pro Glu
225                 230                 235                 240 ttg cag gat gac att cca cac atc cta gcc caa gca cgg aaa atc ttg    845
Leu Gln Asp Asp Ile Pro His Ile Leu Ala Gln Ala Arg Lys Ile Leu
            245                 250                 255 ttc gtg att gac ggc ttt gat gag ctg gga gcc gca cct ggg gcg ctg    893
Phe Val Ile Asp Gly Phe Asp Glu Leu Gly Ala Ala Pro Gly Ala Leu
            260                 265                 270 atc gag gac atc tgc ggg gac tgg gag aag aag aag ccg gtg ccc gtc    941
Ile Glu Asp Ile Cys Gly Asp Trp Glu Lys Lys Lys Pro Val Pro Val
            275                 280                 285 ctc ctg ggg agt ttg ctg aac agg gtg atg tta ccc aag gcc gcc ctg    989
Leu Leu Gly Ser Leu Leu Asn Arg Val Met Leu Pro Lys Ala Ala Leu
290                 295                 300 ctg gtc acc acg cgg ccc agg gcc ctg agg gac ctc cgg atc ctg gcg   1037
Leu Val Thr Thr Arg Pro Arg Ala Leu Arg Asp Leu Arg Ile Leu Ala
305                 310                 315                 320 gag gag ccg atc tac ata agg gtg gag ggc ttc ctg gag gag gac aag   1085
Glu Glu Pro Ile Tyr Ile Arg Val Glu Gly Phe Leu Glu Glu Asp Lys
                325                 330                 335 agg gcc tat ttc ctg aga cac ttt gga gac gag gac caa gcc atg cgt   1133
Arg Ala Tyr Phe Leu Arg His Phe Gly Asp Glu Asp Gln Ala Met Arg
            340                 345                 350 gcc ttt gag cta atg agg agc aac gcg gcc ctg ttc cag ctg ggc tcg   1181
Ala Phe Glu Leu Met Arg Ser Asn Ala Ala Leu Phe Gln Leu Gly Ser
            355                 360                 365 gcc ccc gcg gtg tgc tgg atc gtg tgc acg act ctg aag ctg cag atg   1229
Ala Pro Ala Val Cys Trp Ile Val Cys Thr Thr Leu Lys Leu Gln Met
370                 375                 380 gag aag ggg gag gac ccg gtc ccc acc tgc ctc acc cgc acg ggg ctg   1277
Glu Lys Gly Glu Asp Pro Val Pro Thr Cys Leu Thr Arg Thr Gly Leu
385                 390                 395                 400 ttc ctg cgt ttc ctc tgc agc cgg ttc ccg cag ggc gca cag ctg cgg   1325
Phe Leu Arg Phe Leu Cys Ser Arg Phe Pro Gln Gly Ala Gln Leu Arg
            405                 410                 415 ggc gcg ctg cgg acg ctg agc ctc ctg gcc gcg cag ggc ctg tgg gcg   1373
Gly Ala Leu Arg Thr Leu Ser Leu Leu Ala Ala Gln Gly Leu Trp Ala
            420                 425                 430
```

FIG. 1B

```
cag acg tcc gtg ctt cac cga gag gat ctg gaa agg ctc ggg gtg cag    1421
Gln Thr Ser Val Leu His Arg Glu Asp Leu Glu Arg Leu Gly Val Gln
        435                 440                 445 gag tcc gac ctc cgt ctg ttc ctg gac gga gac atc ctc cgc cag gac    1469
Glu Ser Asp Leu Arg Leu Phe Leu Asp Gly Asp Ile Leu Arg Gln Asp
    450                 455                 460 aga gtc tcc aaa ggc tgc tac tcc ttc atc cac ctc agc ttc cag cag    1517
Arg Val Ser Lys Gly Cys Tyr Ser Phe Ile His Leu Ser Phe Gln Gln
465                 470                 475                 480 ttt ctc act gcc ctg ttc tac acc ctg gag aag gag gag gaa gag gat    1565
Phe Leu Thr Ala Leu Phe Tyr Thr Leu Glu Lys Glu Glu Glu Glu Asp
                485                 490                 495 agg gac ggc cac acc tgg gac att ggg gac gta cag aag ctg ctt tcc    1613
Arg Asp Gly His Thr Trp Asp Ile Gly Asp Val Gln Lys Leu Leu Ser
            500                 505                 510 gga gta gaa aga ctc agg aac ccc gac ctg atc caa gca ggc tac tac    1661
Gly Val Glu Arg Leu Arg Asn Pro Asp Leu Ile Gln Ala Gly Tyr Tyr
        515                 520                 525 tcc ttt ggc ctc gct aac gag aag aga gcc aag gag ttg gag gcc act    1709
Ser Phe Gly Leu Ala Asn Glu Lys Arg Ala Lys Glu Leu Glu Ala Thr
    530                 535                 540 ttt ggc tgc cgg atg tca ccg gac atc aaa cag gaa ttg ctc cga tgc    1757
Phe Gly Cys Arg Met Ser Pro Asp Ile Lys Gln Glu Leu Leu Arg Cys
545                 550                 555                 560 gac ata agt tgt aag ggt gga cat tca acg gtg aca gac ctg cag gag    1805
Asp Ile Ser Cys Lys Gly Gly His Ser Thr Val Thr Asp Leu Gln Glu
                565                 570                 575 ctc ctc ggc tgt ctg tac gag tct cag gag gag gag ctg gtg aag gag    1853
Leu Leu Gly Cys Leu Tyr Glu Ser Gln Glu Glu Glu Leu Val Lys Glu
            580                 585                 590 gtg atg gct cag ttc aaa gaa ata tcc ctg cac tta aat gca gta gac    1901
Val Met Ala Gln Phe Lys Glu Ile Ser Leu His Leu Asn Ala Val Asp
        595                 600                 605 gtt gtg cca tct tca ttc tgc gtc aag cac tgt cga aac ctg cag aaa    1949
Val Val Pro Ser Ser Phe Cys Val Lys His Cys Arg Asn Leu Gln Lys
    610                 615                 620 atg tca ctg cag gta ata aag gag aat ctc ccg gag aat gtc act gcg    1997
Met Ser Leu Gln Val Ile Lys Glu Asn Leu Pro Glu Asn Val Thr Ala
625                 630                 635                 640 tct gaa tca gac gcc gag gtt gag aga tcc cag gat gat cag cac atg    2045
Ser Glu Ser Asp Ala Glu Val Glu Arg Ser Gln Asp Asp Gln His Met
                645                 650                 655
```

FIG. 1C

| | |
|---|---|
| ctt cct ttc tgg acg gac ctt tgt tcc ata ttt gga tca aat aag gat<br>Leu Pro Phe Trp Thr Asp Leu Cys Ser Ile Phe Gly Ser Asn Lys Asp<br>660                                     665                      670 | 2093 |
| ctg atg ggt cta gca atc aat gat agc ttt ctc agt gcc tcc cta gta<br>Leu Met Gly Leu Ala Ile Asn Asp Ser Phe Leu Ser Ala Ser Leu Val<br>          675                             680                           685 | 2141 |
| agg atc ctg tgt gaa caa ata gcc tct gac acc tgt cat ctc cag aga<br>Arg Ile Leu Cys Glu Gln Ile Ala Ser Asp Thr Cys His Leu Gln Arg<br>690                                     695                      700 | 2189 |
| gtg gtg ttc aaa aac att tcc cca gct gat gct cat cgg aac ctc tgc<br>Val Val Phe Lys Asn Ile Ser Pro Ala Asp Ala His Arg Asn Leu Cys<br>705                      710                        715                      720 | 2237 |
| cta gct ctt cga ggt cac aag act gta acg tat ctg acc ctt caa ggc<br>Leu Ala Leu Arg Gly His Lys Thr Val Thr Tyr Leu Thr Leu Gln Gly<br>                    725                             730                        735 | 2285 |
| aat gac cag gat gat atg ttt ccc gca ttg tgt gag gtc ttg aga cat<br>Asn Asp Gln Asp Asp Met Phe Pro Ala Leu Cys Glu Val Leu Arg His<br>                740                             745                      750 | 2333 |
| cca gaa tgt aac ctg cga tat ctc ggg ttg gtg tct tgt tcc gct acc<br>Pro Glu Cys Asn Leu Arg Tyr Leu Gly Leu Val Ser Cys Ser Ala Thr<br>          755                             760                         765 | 2381 |
| act cag cag tgg gct gat ctc tcc ttg gcc ctt gaa gtc aac cag tcc<br>Thr Gln Gln Trp Ala Asp Leu Ser Leu Ala Leu Glu Val Asn Gln Ser<br>770                                     775                      780 | 2429 |
| ctg acg tgc gta aac ctc tcc gac aat gag ctt ctg gat gag ggt gct<br>Leu Thr Cys Val Asn Leu Ser Asp Asn Glu Leu Leu Asp Glu Gly Ala<br>785                      790                        795                      800 | 2477 |
| aag ttg ctg tac aca act ttg aga cac ccc aag tgc ttt ctg cag agg<br>Lys Leu Leu Tyr Thr Thr Leu Arg His Pro Lys Cys Phe Leu Gln Arg<br>                805                             810                      815 | 2525 |
| ttg tcg ttg gaa aac tgt cac ctt aca gaa gcc aat tgc aag gac ctt<br>Leu Ser Leu Glu Asn Cys His Leu Thr Glu Ala Asn Cys Lys Asp Leu<br>          820                             825                        830 | 2573 |
| gct gct gtg ttg gtt gtc agc cgg gag ctg aca cac ctg tgc ttg gcc<br>Ala Ala Val Leu Val Val Ser Arg Glu Leu Thr His Leu Cys Leu Ala<br>                835                             840                      845 | 2621 |
| aag aac ccc att ggg aat aca ggg gtg aag ttt ctg tgt gag ggc ttg<br>Lys Asn Pro Ile Gly Asn Thr Gly Val Lys Phe Leu Cys Glu Gly Leu<br>850                                   855                        860 | 2669 |
| agg tac ccc gag tgt aaa ctg cag acc ttg gtg ctt tgg aac tgc gac<br>Arg Tyr Pro Glu Cys Lys Leu Gln Thr Leu Val Leu Trp Asn Cys Asp<br>865                                   870                      875                      880 | 2717 |

FIG. 1D

```
ata act agc gat ggc tgc tgc gat ctc aca aag ctt ctc caa gaa aaa      2765
Ile Thr Ser Asp Gly Cys Cys Asp Leu Thr Lys Leu Leu Gln Glu Lys
                885                 890                 895 tca agc ctg ttg tgt ttg gat ctg ggg ctg aat cac ata gga gtt aag      2813
Ser Ser Leu Leu Cys Leu Asp Leu Gly Leu Asn His Ile Gly Val Lys
            900                 905                 910 gga atg aag ttc ctg tgt gag gct ttg agg aaa cca ctg tgc aac ttg      2861
Gly Met Lys Phe Leu Cys Glu Ala Leu Arg Lys Pro Leu Cys Asn Leu
        915                 920                 925 aga tgt ctg tgg ttg tgg gga tgt tcc atc cct ccg ttc agt tgt gaa      2909
Arg Cys Leu Trp Leu Trp Gly Cys Ser Ile Pro Pro Phe Ser Cys Glu
    930                 935                 940 gac ctc tgc tct gcc ctc agc aac cag agc ctc gtc act ctg gac ctg      2957
Asp Leu Cys Ser Ala Leu Ser Asn Gln Ser Leu Val Thr Leu Asp Leu
945                 950                 955                 960 ggt cag aat ccc ttg ggg tct agt gga gtg aag atg ctg ttt gaa acc      3005
Gly Gln Asn Pro Leu Gly Ser Ser Gly Val Lys Met Leu Phe Glu Thr
                965                 970                 975 ttg aca tgt tcc agt ggc acc ctc cgg aca ctc agg ttg aaa atc gat      3053
Leu Thr Cys Ser Ser Gly Thr Leu Arg Thr Leu Arg Leu Lys Ile Asp
            980                 985                 990 gac ttt aat gat gaa ctc aat aag ctg ctg gaa gaa ata gaa gaa aaa      3101
Asp Phe Asn Asp Glu Leu Asn Lys Leu Leu Glu Glu Ile Glu Glu Lys
        995                 1000                1005 aac cca caa ctg att att gat act gag aaa cat cat ccc tgg gca gaa      3149
Asn Pro Gln Leu Ile Ile Asp Thr Glu Lys His His Pro Trp Ala Glu
    1010                1015                1020 agg cct tct tct cat gac ttc atg atc                                  3176
Arg Pro Ser Ser His Asp Phe Met Ile
1025                1030

TGAATCCCCC CGAGTCATTC ATTCTCCATG AAGTCATCGA TTTTCCAGGT GTTGGTGAAC    3236
TGCCTGTGAC TCCTCTCCTC CCCGGCCCCT ACCCTCAGG GATAATGAGT TCATTGCTGG     3296
GCTAGATGTT TTAGCCATGA TTCTGCCTCT GTTTTATACC TGCACACATC CTTATCTTTG    3356
TTACATATGA AATATCTGTA TCACGGGTAT ATTGAGAGAA ATAAAGGTGA GAGCATTCAC    3416
AAAAAAAAAA AAAAA                                                     3431
```

FIG. 1E

```
ccacgcgtcc gcccacgcgt ccgggcatct ggggaaacct ttcttccatg gctcaggaca      60
cactcctgga tcgagccaac aggagaactt tctgtgtgga ccgaagccta aggaccctga     120
aaacagctgc agatgaag atg gca agc acc cgc tgc aag ctg gcc agg tac      171
                    Met Ala Ser Thr Arg Cys Lys Leu Ala Arg Tyr
                     1           5                  10 ctg gag gac ctg gag gat gtg gac ttg aag aaa ttt aag atg cac tta      219
Leu Glu Asp Leu Glu Asp Val Asp Leu Lys Lys Phe Lys Met His Leu
            15                  20                  25 gag gac tat cct ccc cag aag ggc tgc atc ccc ctc ccg agg ggt cag      267
Glu Asp Tyr Pro Pro Gln Lys Gly Cys Ile Pro Leu Pro Arg Gly Gln
        30                  35                  40 aca gag aag gca gac cat gtg gat cta gcc acg cta atg atc gac ttc      315
Thr Glu Lys Ala Asp His Val Asp Leu Ala Thr Leu Met Ile Asp Phe
    45                  50                  55 aat ggg gag gag aag gcg tgg gcc atg gcc gtg tgg atc ttc gct gcg      363
Asn Gly Glu Glu Lys Ala Trp Ala Met Ala Val Trp Ile Phe Ala Ala
60                  65                  70                  75 atc aac agg aga gac ctt tat gag aaa gca aaa aga gat gag ccg aag      411
Ile Asn Arg Arg Asp Leu Tyr Glu Lys Ala Lys Arg Asp Glu Pro Lys
                80                  85                  90 tgg ggt tca gat aat gca cgt gtt tcg aat ccc act gtg ata tgc cag      459
Trp Gly Ser Asp Asn Ala Arg Val Ser Asn Pro Thr Val Ile Cys Gln
            95                  100                 105 gaa gac agc att gaa gag gag tgg atg ggt tta ctg gag tac ctt tcg      507
Glu Asp Ser Ile Glu Glu Glu Trp Met Gly Leu Leu Glu Tyr Leu Ser
        110                 115                 120 aga atc tct att tgt aaa atg aag aaa gat tac cgt aag aag tac aga      555
Arg Ile Ser Ile Cys Lys Met Lys Lys Asp Tyr Arg Lys Lys Tyr Arg
    125                 130                 135 aag tac gtg aga agc aga ttc cag tgc att gaa gac agg aat gcc cgt      603
Lys Tyr Val Arg Ser Arg Phe Gln Cys Ile Glu Asp Arg Asn Ala Arg
140                 145                 150                 155 ctg ggt gag agt gtg agc ctc aac aaa cgc tac aca cga ctg cgt ctc      651
Leu Gly Glu Ser Val Ser Leu Asn Lys Arg Tyr Thr Arg Leu Arg Leu
                160                 165                 170 atc aag gag cac cgg agc cag cag gag agg gag cag gag ctt ctg gcc      699
Ile Lys Glu His Arg Ser Gln Gln Glu Arg Glu Gln Glu Leu Leu Ala
            175                 180                 185 atc ggc aag acc aag acg tgt gag agc ccc gtg agt ccc att aag atg      747
Ile Gly Lys Thr Lys Thr Cys Glu Ser Pro Val Ser Pro Ile Lys Met
        190                 195                 200 gag ttg ctg ttt gac ccc gat gat gag cat tct gag cct gtg cac acc      795
Glu Leu Leu Phe Asp Pro Asp Asp Glu His Ser Glu Pro Val His Thr
    205                 210                 215
```

FIG. 4A

```
gtg gtg ttc cag ggg gcg gca ggg att ggg aaa aca atc ctg gcc agg      843
Val Val Phe Gln Gly Ala Ala Gly Ile Gly Lys Thr Ile Leu Ala Arg
220             225             230             235 aag atg atg ttg gac tgg gca tcg ggg aca ctc tac caa gac agg ttt      891
Lys Met Met Leu Asp Trp Ala Ser Gly Thr Leu Tyr Gln Asp Arg Phe
            240             245             250 gac tat ctg ttc tat atc cac tgt cgg gag gtg agc ctt gtg aca cag      939
Asp Tyr Leu Phe Tyr Ile His Cys Arg Glu Val Ser Leu Val Thr Gln
            255             260             265 agg agc ctg ggg gac ctg atc atg agc tgc tgc ccc gac cca aac cca      987
Arg Ser Leu Gly Asp Leu Ile Met Ser Cys Cys Pro Asp Pro Asn Pro
        270             275             280 ccc atc cac aag atc gtg aga aaa ccc tcc aga atc ctc ttc ctc atg     1035
Pro Ile His Lys Ile Val Arg Lys Pro Ser Arg Ile Leu Phe Leu Met
285             290             295 gac ggc ttc gat gag ctg caa ggt gcc ttt gac gag cac ata gga ccg     1083
Asp Gly Phe Asp Glu Leu Gln Gly Ala Phe Asp Glu His Ile Gly Pro
300             305             310             315 ctc tgc act gac tgg cag aag gcc gag cgg gga gac att ctc ctg agc     1131
Leu Cys Thr Asp Trp Gln Lys Ala Glu Arg Gly Asp Ile Leu Leu Ser
            320             325             330 agc ctc atc aga aag aag ctg ctt ccc gag gcc tct ctg ctc atc acc     1179
Ser Leu Ile Arg Lys Lys Leu Leu Pro Glu Ala Ser Leu Leu Ile Thr
            335             340             345 acg aga cct gtg gcc ctg gag aaa ctg cag cac ttg ctg gac cat cct     1227
Thr Arg Pro Val Ala Leu Glu Lys Leu Gln His Leu Leu Asp His Pro
        350             355             360 cgg cat gtg gag atc ctg ggt ttc tcc gag gcc aaa agg aaa gag tac     1275
Arg His Val Glu Ile Leu Gly Phe Ser Glu Ala Lys Arg Lys Glu Tyr
    365             370             375 ttc ttc aag tac ttc tct gat gag gcc caa gcc agg gca gcc ttc agt     1323
Phe Phe Lys Tyr Phe Ser Asp Glu Ala Gln Ala Arg Ala Ala Phe Ser
380             385             390             395 ctg att cag gag aac gag gtc ctc ttc acc atg tgc ttc atc ccc ctg     1371
Leu Ile Gln Glu Asn Glu Val Leu Phe Thr Met Cys Phe Ile Pro Leu
            400             405             410 gtc tgc tgg atc gtg tgc act gga ctg aaa cag cag atg gag agt ggc     1419
Val Cys Trp Ile Val Cys Thr Gly Leu Lys Gln Gln Met Glu Ser Gly
            415             420             425 aag agc ctt gcc cag aca tct aag acc acc acc gcg gta tac gtc ttc     1467
Lys Ser Leu Ala Gln Thr Ser Lys Thr Thr Thr Ala Val Tyr Val Phe
        430             435             440
```

FIG. 4B

| | | | | | | | | | | | | | | | |
|---|---|---|---|---|---|---|---|---|---|---|---|---|---|---|---|
| ttc | ctt | tcc | agt | ttg | ctg | cag | ccc | cgg | gga | ggg | agc | cag | gag | cac | ggc |
| Phe | Leu | Ser | Ser | Leu | Leu | Gln | Pro | Arg | Gly | Gly | Ser | Gln | Glu | His | Gly |
| | 445 | | | | 450 | | | | | 455 | | | | | |

1515 ctc tgc gcc cac ctc tgg ggg ctc tgc tct ttg gct gca gat gga atc  1563
Leu Cys Ala His Leu Trp Gly Leu Cys Ser Leu Ala Ala Asp Gly Ile
460              465                470                475 tgg aac cag aaa atc ctg ttt gag gag tcc gac ctc agg aat cat gga  1611
Trp Asn Gln Lys Ile Leu Phe Glu Glu Ser Asp Leu Arg Asn His Gly
              480                485                490 ctg cag aag gcg gat gtg tct gct ttc ctg agg atg aac ctg ttc caa  1659
Leu Gln Lys Ala Asp Val Ser Ala Phe Leu Arg Met Asn Leu Phe Gln
            495                500                505 aag gaa gtg gac tgc gag aag ttc tac agc ttc atc cac atg act ttc  1707
Lys Glu Val Asp Cys Glu Lys Phe Tyr Ser Phe Ile His Met Thr Phe
        510                515                520 cag gag ttc ttt gcc gcc atg tac tac ctg ctg gaa gag gaa aag gaa  1755
Gln Glu Phe Phe Ala Ala Met Tyr Tyr Leu Leu Glu Glu Lys Glu
525                530                535 gga agg acg aac gtt cca ggg agt cgt ttg aag ctt ccc agc cga gac  1803
Gly Arg Thr Asn Val Pro Gly Ser Arg Leu Lys Leu Pro Ser Arg Asp
540                545                550                555 gtg aca gtc ctt ctg gaa aac tat ggc aaa ttc gaa aag ggg tat ttg  1851
Val Thr Val Leu Leu Glu Asn Tyr Gly Lys Phe Glu Lys Gly Tyr Leu
          560                565                570 att ttt gtt gta cgt ttc ctc ttt ggc ctg gta aac cag gag agg acc  1899
Ile Phe Val Val Arg Phe Leu Phe Gly Leu Val Asn Gln Glu Arg Thr
        575                580                585 tcc tac ttg gag aag aaa tta agt tgc aag atc tct cag caa atc agg  1947
Ser Tyr Leu Glu Lys Lys Leu Ser Cys Lys Ile Ser Gln Gln Ile Arg
        590                595                600 ctg gag ctg ctg aaa tgg att gaa gtg aaa gcc aaa gct aaa aag ctg  1995
Leu Glu Leu Leu Lys Trp Ile Glu Val Lys Ala Lys Ala Lys Lys Leu
605                610                615 cag atc cag ccc agc cag ctg gaa ttg ttc tac tgt ttg tac gag atg  2043
Gln Ile Gln Pro Ser Gln Leu Glu Leu Phe Tyr Cys Leu Tyr Glu Met
620                625                630                635 cag gag gag gac ttc gtg caa agg gcc atg gac tat ttc ccc aag att  2091
Gln Glu Glu Asp Phe Val Gln Arg Ala Met Asp Tyr Phe Pro Lys Ile
              640                645                650 gag atc aat ctc tcc acc aga atg gac cac atg gtt tct tcc ttt tgc  2139
Glu Ile Asn Leu Ser Thr Arg Met Asp His Met Val Ser Ser Phe Cys
            655                660                665

FIG. 4C

```
att gag aac tgt cat cgg gtg gag tca ctg tcc ctg ggg ttt ctc cat     2187
Ile Glu Asn Cys His Arg Val Glu Ser Leu Ser Leu Gly Phe Leu His
        670             675             680 aac atg ccc aag gag gaa gag gag gaa aag gaa ggc cga cac ctt         2235
Asn Met Pro Lys Glu Glu Glu Glu Glu Lys Glu Gly Arg His Leu
        685             690             695 gat atg gtg cag tgt gtc ctc cca agc tcc tct cat gct gcc tgt tct     2283
Asp Met Val Gln Cys Val Leu Pro Ser Ser Ser His Ala Ala Cys Ser
700             705             710             715 cat gga ttg gtg aac agc cac ctc act tcc agt ttt tgc cgg ggc ctc     2331
His Gly Leu Val Asn Ser His Leu Thr Ser Ser Phe Cys Arg Gly Leu
            720             725             730 ttt tca gtt ctg agc acc agc cag agt cta act gaa ttg gac ctc agt     2379
Phe Ser Val Leu Ser Thr Ser Gln Ser Leu Thr Glu Leu Asp Leu Ser
            735             740             745 gac aat tct ctg ggg gac cca ggg atg aga gtg ttg tgt gaa acg ctc     2427
Asp Asn Ser Leu Gly Asp Pro Gly Met Arg Val Leu Cys Glu Thr Leu
        750             755             760 cag cat cct ggc tgt aac att cgg aga ttg tgg ttg ggg cgc tgt ggc     2475
Gln His Pro Gly Cys Asn Ile Arg Arg Leu Trp Leu Gly Arg Cys Gly
765             770             775 ctc tcg cat gag tgc tgc ttc gac atc tcc ttg gtc ctc agc agc aac     2523
Leu Ser His Glu Cys Cys Phe Asp Ile Ser Leu Val Leu Ser Ser Asn
780             785             790             795 cag aag ctg gtg gag ctg gac ctg agt gac aac gcc ctc ggt gac ttc     2571
Gln Lys Leu Val Glu Leu Asp Leu Ser Asp Asn Ala Leu Gly Asp Phe
            800             805             810 gga atc aga ctt ctg tgt gtg gga ctg aag cac ctg ttg tgc aat ctg     2619
Gly Ile Arg Leu Leu Cys Val Gly Leu Lys His Leu Leu Cys Asn Leu
        815             820             825 aag aag ctc tgg ttg gtc agc tgc tgc ctc aca tca gca tgt tgt cag     2667
Lys Lys Leu Trp Leu Val Ser Cys Cys Leu Thr Ser Ala Cys Cys Gln
        830             835             840 gat ctt gca tca gta ttg agc acc agc cat tcc ctg acc aga ctc tat     2715
Asp Leu Ala Ser Val Leu Ser Thr Ser His Ser Leu Thr Arg Leu Tyr
845             850             855 gtg ggg gag aat gcc ttg gga gac tca gga gtc gca att tta tgt gaa     2763
Val Gly Glu Asn Ala Leu Gly Asp Ser Gly Val Ala Ile Leu Cys Glu
860             865             870             875 aaa gcc aag aat cca cag tgt aac ctg cag aaa ctg ggg ttg gtg aat     2811
Lys Ala Lys Asn Pro Gln Cys Asn Leu Gln Lys Leu Gly Leu Val Asn
            880             885             890
```

FIG. 4D

```
tct ggc ctt acg tca gtc tgt tgt tca gct ttg tcc tcg gta ctc agc    2859
Ser Gly Leu Thr Ser Val Cys Cys Ser Ala Leu Ser Ser Val Leu Ser
            895             900             905 act aat cag aat ctc acg cac ctt tac ctg cga ggc aac act ctc gga    2907
Thr Asn Gln Asn Leu Thr His Leu Tyr Leu Arg Gly Asn Thr Leu Gly
            910             915             920 gac aag ggg atc aaa cta ctc tgt gag gga ctc ttg cac ccc gac tgc    2955
Asp Lys Gly Ile Lys Leu Leu Cys Glu Gly Leu Leu His Pro Asp Cys
        925             930             935 aag ctt cag gtg ttg gaa tta gac aac tgc aac ctc acg tca cac tgc    3003
Lys Leu Gln Val Leu Glu Leu Asp Asn Cys Asn Leu Thr Ser His Cys
940             945             950             955 tgc tgg gat ctt tcc aca ctt ctg acc tcc agc cag agc ctg cga aag    3051
Cys Trp Asp Leu Ser Thr Leu Leu Thr Ser Ser Gln Ser Leu Arg Lys
            960             965             970 ctg agc ctg ggc aac aat gac ctg ggc gac ctg ggg gtc atg atg ttc    3099
Leu Ser Leu Gly Asn Asn Asp Leu Gly Asp Leu Gly Val Met Met Phe
            975             980             985 tgt gaa gtg ctg aaa cag cag agc tgc ctc ctg cag aac ctg ggg ttg    3147
Cys Glu Val Leu Lys Gln Gln Ser Cys Leu Leu Gln Asn Leu Gly Leu
            990             995             1000 tct gaa atg tat ttc aat tat gag aca aaa agt gcg tta gaa aca ctt    3195
Ser Glu Met Tyr Phe Asn Tyr Glu Thr Lys Ser Ala Leu Glu Thr Leu
    1005            1010            1015 caa gaa gaa aag cct gag ctg acc gtc gtc ttt gag cct tct tgg tag    3243
Gln Glu Glu Lys Pro Glu Leu Thr Val Val Phe Glu Pro Ser Trp *
1020            1025            1030 gagtggaaac ggggctgcca gacgccagtg ttctccggtc cctccagctg ggggccctca   3303
ggtggagaga gctgcgatcc atccaggcca agaccacagc tctgtgatcc ttccggtgga   3363
gtgtcggaga agagagcttg ccgacgatgc cttcctgtgc agagcttggg catctccttt   3423
acgccagggt gaggaagaca ccaggacaat gacagcatcg ggtgttgttc tcatcacagc   3483
gcctcagtta gaggatgttc ctcttggtga cctcatgtaa ttagctcatt caataaagca   3543
ctttctttat ttttctcttc tctgtctaac tttcttttc ctatcttttt ttcttctttg    3603
ttctgtttac ttttgctcat atcatcattc ccgctaactt tctattaact gaccataaca   3663
cagaactagt tgactatata ttatgttgaa attttatggc agctatttat ttatttaaat   3723
tttttgtaat agtttgttt tctaataaga aaaatccatg cttttgtag ctggttgaaa     3783
attcaggaat atgtaaaact ttttggtatt taattaaatt gattcctttt cttaattta    3843
aaaaaaaaaa aaaa                                                     3857
```

FIG. 4E

LRR_RI_2: domain 1 of 8, from 726 to 752: score 0.1, E = ...
       ->npsLreLdlsnNkIgdeGaraLaeaLks<-*
          ++  L  L++N+   d+   aL+e+L++
NBS1  726 HKTVTYLTLQGND-QDDMFPALCEVLRH 752

FIG. 8A

LRR_RI_2: domain 2 of 8, from 782 to 809: score 20.8, E = 0.031
       ->npsLreLdlsnNkIgdeGaraLaeaLks<-*
          n+sL  +Ls+N l deGa+ L   -L++
NBS1  782 NQSLTCVNLSDNELLDEGAKLLYTTRH 809

FIG. 8B

LRR_RI_2: domain 3 of 8, from 811 to 838: score 21.9, E = 0.016
       ->npsLreLdlsnNkIgdeGaraLaeaLks<-*
          ++ L++L+L+n++l+++ ++ La++L
NBS1  811 KCFLQRLSLENCHLTEANCKDLAAVLVV 838

FIG. 8C

LRR_RI_2: domain 4 of 8, from 839 to 866: score 13.4, E = 0.56
                *->npsLreLdLsnNkLgdeGaraLaeaLks<-*
                   ++ L  L L+ N++g  G++ L+e+L+
NBS1    839    SRELTHLCLAKNPIGNTGVKFLCEGLRY    866

FIG. 8D

LRR_RI_2: domain 5 of 8, from 868 to 895: score 17.0, E = 0.17
                *->npsLreLdLsnNkLgdeGaraLaeaLks<-*
                   ++L++L L+n++++ +G+  L  ++L++
NBS1    868    ECKLQTLVLWNCDITSDGCCDLTKLLQE    895

FIG. 8E

LRR_RI_2: domain 6 of 8, from 896 to 923: score 22.6, E = 0.0091
                *->npsLreLdLsnNkLgdeGaraLaeaLks<-*
                   ++sL+ LdL+ N++g +G++ L+eaL+
NBS1    896    KSSLLCLDLGLNHIGVKGMKFLCEALRK    923

FIG. 8F

```
LRR_RI_2: domain 7 of 8, from 925 to 952: score 15.8, E = 0.26
             *->npsLreLdLsnNklgdeGaraLaeaLks<-*
                +++Lr L+L+++ + +    L++aL+
    NBS1   925   LCNLRCLWLWGCSIPPFSCEDLCSALSN   952
```

FIG. 8G

```
LRR_RI_2: domain 8 of 8, from 953 to 979: score 14.0, E = 0.47
             *->npsLreLdLsnNklgdeGaraLaeaLks<-*
                +sL +LdL++N+lg +G++ L e+L+
    NBS1   953   -QSLVTLDLGQNPLGSSGVKMLFETLTC   979
```

```
LRR: domain 1 of 9, from 740 to 767: score 10.9, E = 25       FIG. 10A
              *->nLeeLdLsnN.Lt....slppglfsnLp<-*
                 +L+eLdLs+N+L +++  +   +++++
    pyrin-1  740    SLTELDLSDNsLGdpgmRVLCETLQHPG    767

LRR: domain 2 of 9, from 769 to 796: score 2.3, E = 4.6e+02
              *->nLeeLdLsnN.Lt.....slppglfsnLp<-*
                 n+++L+L +++L+++     +++   ++s+ +           FIG. 10B
    pyrin-1  769    NIRRLWLGRCgLSheccfDISL-VLSSNQ  796

LRR: domain 3 of 9, from 797 to 821: score 9.7, E = 39       FIG. 10C
              *->nLeeLdLsnN.Lt..slppglfsnLp<-*
                 +L eLdLs+N L +  ++    l+ +L+
    pyrin-1  797    KLVELDLSDNaLGdfGIRL-LCVGLK   821

LRR: domain 4 of 9, from 826 to 849: score 4.1, E = 2.5e+02
              *->nLeeLdLsnN.LtslppglfsnLp<-*
                 nL++L+L ++ Lts         +++          FIG. 10D
    pyrin-1  826    NLKKLWLVSCcLTSACCQDLASVL   849

LRR: domain 5 of 9, from 854 to 878: score 0.6, E = 8.2e+02
              *->nLeeLdLsnN.Lt..slppglfsnLp<-*
                 +L++L++   N L ++++     l+++ +          FIG. 10E
    pyrin-1  854    SLTRLYVGENaLGdsGVAI-LCEKAK  878

LRR: domain 6 of 9, from 883 to 906: score 5.1, E = 1.8e+02
              *->nLeeLdLsnN.LtslppglfsnLp<-*
                 nL++L L n +Lts+    +++s+             FIG. 10F
    pyrin-1  883    NLQKLGLVNSgLTSVCCSALSSVL   906

LRR: domain 7 of 9, from 911 to 935: score 10.2, E = 32
              *->nLeeLdLsnN.Lt..slppglfsnLp<-*
                 nL++L+L++N+L ++++    l+++L          FIG. 10G
    pyrin-1  911    NLTHLYLRGNtLGdkGIKL-LCEGLL   935

LRR: domain 8 of 9, from 940 to 967: score 5.8, E = 1.4e+02
              *->nLeeLdLsnN.Lt.....slppglfsnLp<-*
                 +L++L L+n++Lt++    +l+  l+ + +           FIG. 10H
    pyrin-1  940    KLQVLELDNCnLTshccwDLST-LLTSSQ    967

LRR: domain 9 of 9, from 968 to 991: score 8.4, E = 59
              *->nLeeLdLsnN.LtslppglfsnLp<-*
                 +L++L+L nN+L +l    f+             FIG. 10I
    pyrin-1  968    SLRKLSLGNNdLGDLGVMMFCEVL   991
```

US 7,300,749 B2

MOLECULES OF THE PYRIN DOMAIN PROTEIN FAMILY AND USES THEREOF

RELATED APPLICATIONS

This application is a continuation-in-part and claims the benefit of priority under 35 U.S.C. 120 of U.S. application Ser. No. 10/027,629, filed on Dec. 20, 2001, now abandoned which is a continuation-in-part and claims the benefit of priority of U.S. application Ser. No. 09/964,955, filed on Sep. 26, 2001, now abandoned which is a continuation-in-part and claims the benefit of priority of U.S. application Ser. No. 09/653,901, filed on Sep. 1, 2000 now abandoned; which is a continuation-in-part of U.S. application Ser. No. 09/506,067, filed on Feb. 17, 2000 now abandoned. The disclosure of the prior applications are considered part of and incorporated by reference in the disclosure of this application.

BACKGROUND OF THE INVENTION

The CED4/Apaf1 family of proteins are intracellular, receptor-like molecules that coordinate the assembly of signaling complexes that regulate the activation of NF-kB, cytokine processing, and apoptosis. Human members of this family include: Apaf1, CARD4 (Nod1), Nod2 (CARD15), CARD 7 (DEFCAP/NAC/NALP1) and CARD12 (Ipaf/Clan) (Zou et al. (1997) Cell 90:405; Bertin et al. (1999) J. Biol. Chem. 275:41082; Inohara (1999) J. Biol Chem. 276:4812; Ogura et al. (2001) Nature 411:603; Bertin and DiStefano (2000) Cell Death Differ 7:1273; Hlaing et al. (2001) J. Biol Chem. 276:9230;, Chu et al. J. Biol. Chem. 276:9239; Geddes et al. (2001) Biochem. Biophys. Res. Commun. 284:77; Poyet (2001) J. Biol. Chem. 276:28309; Mactinon et al. (2001) Curr. Biol. 11:118; and Damiano et al. (2001) Genomics 75:77); PCT US 99/255544; PCT US 00/17691; and PCT US 00/29643. Each family member contains a CARD domain that mediates assembly with a downstream CARD-containing signaling partner, and a nucleotide-binding site that regulates activation of the signaling complex. In addition, each member contains a domain of either WD-40 repeats (Apaf1) or leucine-rich repeats (LRR; CARD4, CARD7, Nod2 and CARD12) that function as binding sites for upstream regulators. The NBS/LRR structure of CARD4, CARD7, Nod2 and CARD12 is strikingly similar to the plant NBS/LRR family of signaling proteins that induce gene expression and cell death in response to pathogen infection. However, plant NBS/LRR proteins contain either a leucine zipper motif or a Toll/interleukin-1 receptor homology region in place of a CARD domain. The regulation of NF-kB signaling by CARD4 and Nod2, and the activation of caspase-1 by CARD12 identifies these CED4/Apaf1 family members as important components of inflammatory signaling pathways. Consistent with this hypothesis, mutations within the Nod2 gene have been found to confer susceptibility to several chronic inflammatory disorders, including Crohn's disease and Blau syndrome (Hugot et al. (2001) Nature 411:537; Miceli-Richard et al. (2001) Nat. Genet. 29:19).

Nuclear factor-κB (NF-κB) is a transcription factor expressed in many cell types and which activates homologous or heterologous genes that have κB sites in their promoters. Molecules that regulate NF-κB activation play a critical role in both apoptosis and inflammation. Quiescent NF-κB resides in the cytoplasm as a heterodimer of proteins referred to as p50 and p65 and is complexed with the regulatory protein IκB. NF-κB binding to IκB causes to remain in the cytoplasm. At least two dozen stimuli that activate NF-κB are known (New England Journal of Medicine 336:1066, 1997) and they include cytokines, protein kinase C activators, oxidants, viruses, and immune system stimuli. NF-κB activating stimuli activate specific IκB kinases that phosphorylate IκB leading to its degradation. Once liberated from IκB, NF-κB translocates to the nucleus and activates genes with κB sites in their promoters. The proinflammatory cytokines TNF-α and IL-1 induce NF-κB activation by binding their cell-surface receptors and activating the NF-κB-inducing kinase, NIK, and NF-κB. NIK phosphorylates the IκB kinases α and β which phosphorylate IκB, leading to its degradation.

NF-κB and the NF-κB pathway has been implicated in mediating chronic inflammation in inflammatory diseases such as asthma, ulcerative colitis, rheumatoid arthritis (Epstein, New England Journal of Medicine 336:1066, 1997) and inhibiting NF-κB or NF-κB pathways may be an effective way of treating these diseases.

CARD7 and NBS1 are NBS/LRR proteins with N-terminal PYRIN-domains (Bertin and DiStefano, supra). The PYRIN domain is a protein-protein interaction module belonging to the death domain-fold superfamily which includes the CARD, death, and death effector domains (Bertin et al. (2000) J. Biol Chem. 275:41082; Pawlowski et al. (2001) Trends Biochem Sci. 26:85; Martinon et al. (2001) supra; Fairbrother et al. (2001) Prot. Sci. 10:1911. Proteins containing the PYRIN domain share homology with the N-terminal region of pyrin, a protein that functions to regulate inflammatory signaling in myeloid cells (Centola et al. (2000) Blood 95:3223). Mutations within the pyrin gene confer susceptibility to familial Mediterranean fever, a type of hereditary periodic inflammatory disease (The International FMF Consortium, 1997). In addition, the apoptosis proteins ASC and zebrafish caspase-13 each contain N-terminal PYRIN domains suggesting that PYRIN family members function in both inflammatory and apoptotic signaling (Masamuto et al. (1999) J. Biol. Chem. 274:33835; Inohara and Nunez, (2000) J. Biol. Chem. 276:2551.

SUMMARY OF THE INVENTION

The invention features human NBS-1 and human PYRIN-1. Both NBS-1 and PYRIN-1 have a pyrin domain, so-named for its homology to a portion of pyrin (marenostrin). NBS-1 and PYRIN-1 also have a nucleotide binding site (NBS) domain and a leucine rich repeat domain (LRR) domain, both of which are present in a number of proteins that transmit signals which activate apoptotic and inflammatory pathways in response to stress and other stimuli.

The invention features a method for identifying a compound which binds to a polypeptide comprising the amino acid sequence of SEQ ID NO:2 or SEQ ID NO:5, the method comprising the steps of: a) contacting a polypeptide comprising the amino acid sequence of SEQ ID NO:2 or SEQ ID NO:5, or a cell expressing a polypeptide comprising the amino acid sequence of SEQ ID NO:2 or SEQ ID NO:5 with a test compound; and b) determining whether the polypeptide binds to the test compound. In various embodiments, the binding of the test compound to the polypeptide is detected by a method selected from the group consisting of: a) detection of binding by direct detecting of test compound/polypeptide binding; b) detection of binding using a competition binding assay; c) detection of binding using an assay for NBS-1 or PYRIN-1-mediated signal transduction; d)

detection of binding using an assay for proteolytic activity; e) detection of binding to a pyrin domain; and f) detection of binding to ASC.

The invention also features a method for modulating the activity of a polypeptide comprising the amino acid sequence of SEQ ID NO:2 or SEQ ID NO:5 comprising contacting a polypeptide comprising the amino acid sequence of SEQ ID NO:2 or SEQ ID NO:5 or a cell expressing a polypeptide comprising the amino acid sequence of SEQ ID NO:2 or SEQ ID NO:5 with a compound which binds to the polypeptide in a sufficient concentration to modulate the activity of the polypeptide.

The invention includes a method for identifying a compound which modulates the activity of a polypeptide comprising the amino acid sequence of SEQ ID NO:2 or SEQ ID NO:5, the method comprising: a) contacting the polypeptide with a test compound; and b) determining the effect of the test compound on the activity of the polypeptide to thereby identify a compound which modulates the activity of the polypeptide.

Also within the invention is a method of treating a disorder associated with inappropriate apoptosis, the method comprising modulating the expression or activity of NBS-1 or PYRIN-1.

The invention also features a method for identifying a candidate compound for modulating the binding of PYRIN-1 to ASC, the method comprising: a) measuring the binding of a first polypeptide comprising the pyrin domain of ASC to a second polypeptide comprising the pyrin domain of PYRIN-1 in the presence of a test compound; and b) comparing the binding of the first polypeptide to the second polypeptide measured in step (a) to the binding of the first polypeptide to the second polypeptide in the absence of the test compound, wherein altered binding of the first polypeptide to the second polypeptide in the presence of the test compound compared the binding in the absence of the test compound indicates that the test compound modulates the binding of PYRIN-1 to ASC.

In another embodiment the method includes a method for identifying a candidate compound for modulating the ASC-mediated activation of NF-κB, the method comprising: a) measuring the binding of a first polypeptide comprising the pyrin domain of ASC to a second polypeptide comprising the pyrin domain of PYRIN-1 in the presence of a test compound; and b) comparing the binding of the first polypeptide to the second polypeptide measured in step (a) to the binding of the first polypeptide to the second polypeptide in the absence of the test compound, wherein altered binding of the first polypeptide to the second polypeptide in the presence of the test compound compared the binding in the absence of the test compound indicates that the test compound is candidate compound for modulating the ASC-mediated activation of NF-kB.

In another embodiment the invention features a method for identifying an modulator of NF-kB activity, the method comprising: a) providing a cell expressing recombinant ASC and recombinant PYRIN-1; b) exposing the cell to a test compound; and c) measuring the NF-kB activity of the cell in the presence of the test compound, wherein altered activation in the presence of the test compound compared to the absence of the test compound indicates that the compound is a modulator of NF-kB activity.

In another embodiment the invention features a method for identifying a candidate compound for modulating the ASC-mediated activation of NF-kB, the method comprising: a) measuring the binding of a test compound to the LRR domain of PYRIN-1; and b) determining that the test compound is a candidate compound for modulating the ASC-mediated activation of NF-kB when the test compound binds to the LRR domain of PYRIN-1.

In another embodiment the invention features a method for identifying a candidate compound for modulating the ASC-mediated activation of NF-kB, the method comprising: a) measuring the binding of a test compound to the LRR domain of PYRIN-1; and b) identifying the test compound as an LRR domain binding compound when the test compound binds to the LRR domain of PYRIN-1; c) measuring the activation of NF-B in a cell expressing ASC and PYRIN-1 in the presence and absence of the LRR domain binding compound, wherein the LRR domain binding compound is a candidate compound for modulating the ASC-mediated activation of NF-B if the activation of NF-kB in the presence of the LRR domain binding compound is greater than in the absence of the LRR domain binding compound.

In another embodiment the invention features a method for identifying a candidate modulator of PYRIN-1, the method comprising: a) contacting a purified polypeptide comprising the NBS domain of PYRIN-1 with a test compound in the presence of a nucleotide that binds to the NBS domain in the absence of the test compound; b) measuring the binding of the nucleotide to the NBS domain in the presence of the test compound; and c) identifying the test compound as a candidate modulator of PYRIN-1 if the test compound reduces the binding of the nucleotide to the NBS domain. In various embodiments: the nucleotide is bound to the NBS domain before the polypeptide is exposed to the test compound, the test compound is exposed to the polypeptide before the polypeptide is exposed to the nucleotide, the nucleotide is selected from the group consisting of an adenine nucleotide, a guanidine nucleotide, a thymidine nucleotide, a cytosine nucleotide, and a uridine nucleotide, the nucleotide is selected from the group consisting of a ribonucleotide and a dideoxribonucleotide, and the nucleotide is selected from the group consisting of: ATP, ADP, TTP, TDP, UTP, UDP, CTP, CDP, GTP, and GTP.

In another embodiment the invention features a method for identifying a candidate modulator of PYRIN-1, the method comprising: a)contacting a purified polypeptide comprising the NBS domain of PYRIN-1 with a test compound in the presence of a nucleotide that binds to the NBS domain in the absence of the test compound; b) measuring the binding of the nucleotide to the NBS domain in the presence of the test compound; c) identifying a test compound that reduces the binding of the nucleotide to the NBS domain; and d) measuring the binding of a test compound that reduces the binding of the nucleotide to the NBS domain of PYRIN-1 to an NBS domain of a protein other than PYRIN-1; wherein the test compound is a candidate modulator of PYRIN-1 if it reduces the binding of the nucleotide to the NBS domain of PYRIN-1 and does not substantially reduce the binding of the nucleotide of the NBS domain of a protein other than PYRIN-1. In certain embodiments, the NBS of a protein other than PYRIN-1 is the NBS domain of a protein selected from the group consisting of: NBS-1, CARD-12, and CARD-4.

In another embodiment the invention features a method for identifying a candidate modulator of PYRIN-1, the method comprising: a) contacting a purified polypeptide comprising the NBS domain of PYRIN-1 with a test compound in the presence of a nucleotide triphosphate that binds to the NBS domain in the absence of the test compound; b) measuring the hydrolysis of the nucleotide triphosphate in the presence of the test compound; and c) identifying the test compound is a candidate modulator of PYRIN-1 if the test compound reduces the hydrolysis of the nucleotide triphosphate.

In another embodiment the invention features a method for identifying a modulator of caspase-1 activity, the method including: a) providing a cell expressing recombinant PYRIN-1; b) exposing the cell to a test compound; and c) measuring caspase-1 activity of the cell in the presence of the test compound, wherein altered caspase-1 activity in the presence of the test compound compared to the absence of the test compound indicates that the compound is a modulator of caspase-1 activity.

A fragment of PYRIN-1, e.g., a fragment containing the pyrin domain, can be used in the methods described herein. In addition to recombinant PYRIN-1 or a fragment thereof, a cell can also express recombinant ASC, caspase-1, and/or a fragment of ASC or caspase-1. Caspase-1 activity can be detected, for example, by measuring the presence of protein products produced by caspase-1 proteolytic activity (e.g., detecting IL-1β secretion).

The method can also include an additional step of measuring the caspase-1 activity of the cell in the absence of the test compound and/or in the absence of PYRIN-1 (e.g., recombinant PYRIN-1).

In another embodiment the invention features a method for identifying a candidate modulator of PYRIN-1, the method including: a) contacting a purified polypeptide containing the pyrin domain of PYRIN-1 with a test compound in the presence of caspase-1 and a caspase-1 substrate; b) measuring the proteolysis of the caspase-1 substrate in the presence of the test compound; and c) identifying the test compound as a candidate modulator of PYRIN-1 if the test compound modulates the proteolysis of the caspase-1 substrate. For example, the caspase-1 substrate can be a unprocessed form of a cytokine, e.g., pro-IL-1β, wherein caspase-1 proteolysis results in the formation of a bioactive form of the cytokine, e.g., bioactive IL-1β.

The method can also include an additional step of measuring the proteolysis of the caspase-1 substrate in the absence of the test compound and/or comparing the proteolysis of the caspase-1 substrate in the absence of the test compound with that measured in the presence of the test compound.

The invention also features a method for modulating ASC activity in a patient, the method comprising administering a compound that alters the activity of PYRIN-1, a method for modulating NF-kB activity in a patient, the method comprising administering a compound that alters the activity of PYRIN-1, and a method for treating an inflammatory disorder in a patient, the method comprising administering a compound that alters the activity of PYRIN-1.

The above described methods can also be used for identifying a candidate compound for treating an inflammatory disorder.

In another aspect, the present invention provides a method for detecting the presence of NBS-1 or PYRIN-1 activity or expression in a biological sample by contacting the biological sample with an agent capable of detecting an indicator of NBS-1 or PYRIN-1 activity such that the presence of NBS-1 or PYRIN-1 activity is detected in the biological sample.

In another aspect, the invention provides a method for modulating NBS-1 or PYRIN-1 activity comprising contacting a cell with an agent that modulates (inhibits or stimulates) NBS-1 or PYRIN-1 activity or expression such that NBS-1 or PYRIN-1 activity or expression in the cell is modulated. In one embodiment, the agent is an antibody that specifically binds to NBS-1 or PYRIN-1 protein. In another embodiment, the agent modulates expression of NBS-1 or PYRIN-1 by modulating transcription of a NBS-1 or PYRIN-1 gene, splicing of a NBS-1 or PYRIN-1 mRNA, or translation of a NBS-1 or PYRIN-1 mRNA. In yet another embodiment, the agent is a nucleic acid molecule having a nucleotide sequence that is antisense to the coding strand of the NBS-1 or PYRIN-1 mRNA or the NBS-1 or PYRIN-1 gene.

In one embodiment, the methods of the present invention are used to treat a subject having a disorder characterized by aberrant NBS-1 or PYRIN-1 protein or nucleic acid expression or activity or related to NBS-1 or PYRIN-1 expression or activity by administering an agent which is a NBS-1 or PYRIN-1 modulator to the subject. In one embodiment, the NBS-1 or PYRIN-1 modulator is a NBS-1 or PYRIN-1 protein. In another embodiment the NBS-1 or PYRIN-1 modulator is a NBS-1 or PYRIN-1 nucleic acid molecule. In other embodiments, the NBS-1 or PYRIN-1 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a NBS-1 or PYRIN-1 protein; (ii) mis-regulation of a gene encoding a NBS-1 or PYRIN-1 protein; (iii) aberrant RNA splicing; and (iv) aberrant post-translational modification of a NBS-1 or PYRIN-1 protein, wherein a wild-type form of the gene encodes a protein with a NBS-1 or PYRIN-1 activity.

In another aspect, the invention provides a method for identifying a compound that binds to or modulates the activity of a NBS-1 or PYRIN-1 protein. In general, such methods entail measuring a biological activity of a NBS-1 or PYRIN-1 protein in the presence and absence of a test compound and identifying those compounds that alter the activity of the NBS-1 or PYRIN-1 protein.

The invention also features methods for identifying a compound that modulates the expression of NBS-1 or PYRIN-1 by measuring the expression of NBS-1 or PYRIN-1 in the presence and absence of a compound.

Because compounds that modulate the activity or expression of NBS-1 PYRIN-1 and/or ASC may be useful for modulating an inflammatory response, modulating NF-kB activation, modulating apoptotic response, treating inflammatory disorders, e.g., auto-inflammatory disorders and disorders associated with an inappropriate level of apoptosis, assays which identify compounds that modulate the activity or expression of NBS-1 or PYRIN-1 can be used to identify candidate compounds for the treatment of such disorders. Thus, an assay which identifies compounds that modulate the activity or expression of PYRIN-1 are useful for identifying candidate compounds for the treatment of Muckle-Wells syndrome or familial cold urticaria or arthritis. Such assays can also be used to identify candidate compounds for treatment of other inflammatory diseases such as inflammatory bowel disorders, Crohn's disease, ulcerative colitis, reactive arthritis, rheumatoid arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, respiratory inflammatory diseases and disorders, such as asthma and chronic obstructive pulmonary disease, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

The invention also features methods for treating disorders associated with inappropriate apoptosis (e.g., Alzheimer's diseases or other neurological disorders associated with neuronal apoptosis) by modulating the expression or activity of NBS-1 or PYRIN-1.

Among the forms of NBS-1 and PYRIN-1 useful in the method of the invention include those containing some or all of the full-length polypeptide sequences disclosed herein. In many cases a polypeptide comprising only one or a few domains of NBS-1 or PYRIN-1 will be useful. For example, polypeptides comprising the pyrin domain of PYRIN-1, but not the LRR domain of PYRIN-1 are useful in certain screening assays.

Thus, an isolated NBS-1 protein having an amino acid sequence that is at least about 65%, preferably 75%, 85%, 95%, or 98% identical to the amino acid sequence of SEQ ID NO:2; an isolated NBS-1 protein having an amino acid sequence that is at least about 65%, preferably 75%, 85%, 95%, or 98% identical to the pyrin domain of SEQ ID NO:2 (e.g., about amino acid residues 3-79 of SEQ ID NO:2); an isolated NBS-1 protein having an amino acid sequence that is at least about 65%, preferably 75%, 85%, 95%, or 98% identical to the NBS domain of SEQ ID NO:2 (e.g., about amino acids 174-605 of SEQ ID NO:2); an isolated NBS-1 protein having an amino acid sequence that is at least about 65%, preferably 75%, 85%, 95%, or 98% identical to the kinase 1a domain of SEQ ID NO:2 (e.g., about amino acids 180-195 of SEQ ID NO:2); an isolated NBS-1 protein having an amino acid sequence that is at least about 65%, preferably 75%, 85%, 95%, or 98% identical to the kinase 1a domain of SEQ ID NO:2 (e.g., about amino acids 180-195 of SEQ ID NO:2); an isolated NBS-1 protein having an amino acid sequence that is at least about 65%, preferably 75%, 85%, 95%, or 98% identical to the kinase 2 domain of SEQ ID NO:2 (e.g., about amino acids 249-264 of SEQ ID NO:2); an isolated NBS-1 protein having an amino acid sequence that is at least about 65%, preferably 75%, 85%, 95%, or 98% identical to the kinase 3a domain of SEQ ID NO:2 (e.g., about amino acids 302-313 of SEQ ID NO:2); an isolated NBS-1 protein having an amino acid sequence that is at least about 65%, preferably 75%, 85%, 95%, or 98% identical to the LRR domain of SEQ ID NO:2 (e.g., about amino acids 670-1008 of SEQ ID NO:2); and an isolated NBS-1 protein having an amino acid sequence that is at least about 65%, preferably 75%, 85%, 95%, or 98% identical to one or more of the leucine rich repeat of SEQ ID NO:2 (e.g., about amino acids residues 670-697, 698-725, 726-752, 754-781, 782-809, 811-838, 839-866, 868-895, 896-923, 925-952, 953-979, and 981-1008 of SEQ ID NO:2) can be useful in the methods of the invention.

Similarly, an isolated PYRIN-1 protein having an amino acid sequence that is at least about 65%, preferably 75%, 85%, 95%, or 98% identical to the amino acid sequence of SEQ ID NO:5; an isolated PYRIN-1 protein having an amino acid sequence that is at least about 65%, preferably 75%, 85%, 95%, or 98% identical to the pyrin domain of SEQ ID NO:5 (e.g., about amino acid residues 1-87 of SEQ ID NO:5); an isolated PYRIN-1 protein having an amino acid sequence that is at least about 65%, preferably 75%, 85%, 95%, or 98% identical to the NBS domain of SEQ ID NO:5 (e.g., about amino acids 263-357 of SEQ ID NO:5); an isolated PYRIN-1 protein having an amino acid sequence that is at least about 65%, preferably 75%, 85%, 95%, or 98% identical to the kinase 1a domain of SEQ ID NO:5 (e.g., about amino acids 224-233 of SEQ ID NO:5); an isolated PYRIN-1 protein having an amino acid sequence that is at least about 65%, preferably 75%, 85%, 95%, or 98% identical to the kinase 2 domain of SEQ ID NO:5 (e.g., about amino acids 290-306 of SEQ ID NO:5); an isolated PYRIN-1 protein having an amino acid sequence that is at least about 65%, preferably 75%, 85%, 95%, or 98% identical to the kinase 3a domain of SEQ ID NO:5 (e.g., about amino acids 344-355 of SEQ ID NO:5); an isolated PYRIN-1 protein having an amino acid sequence that is at least about 65%, preferably 75%, 85%, 95%, or 98% identical to the LRR domain of SEQ ID NO:5 (e.g., about amino acids 740-991 of SEQ ID NO:5); and an isolated PYRIN-1 protein having an amino acid sequence that is at least about 65%, preferably 75%, 85%, 95%, or 98% identical to one or more of the leucine rich repeat of SEQ ID NO:5 (e.g., about amino acids residues 740-767, 769-796, 797-821, 826-849, 854-878, 883-906, 911-935, 940-967, and 968-991 of SEQ ID NO:5) can be useful in the methods of the invention.

NBS-1 or PYRIN-1 proteins and polypeptides useful in the methods of the invention preferably have at least one biological activity possessed by naturally occurring human NBS-1 or PYRIN-1, e.g., (i) the ability to interact with proteins in an apoptotic or inflammatory signaling pathway, e.g., ASC and/or caspase-1; (ii) the ability to interact with a NBS-1 or PYRIN-1; (iii) the ability to bind to and/or hydrolyze a nucleotide, e.g., ATP or GTP; (iv) the ability to interact with an intracellular target protein; (v) the ability to interact, directly or indirectly, with one or more proteins having a pyrin domain, a CARD domain, or other domain associated with apoptotic and/or inflammatory signaling; (vi) the ability to modulate, directly or indirectly, the activity of a caspase, e.g., caspase-9, caspase-4, caspase-1, and caspase-5; (vii) the ability to induce the activity of caspase-1; (viii) the ability to modulate of ER-specific apoptosis pathways; (ix) the ability to modulate (increase or decrease), directly or indirectly, the activity of NF-kB; or (x) the ability to increase the activity of NF-kB. Other activities include: (1) modulation of cellular proliferation; (2) modulation of cellular differentiation; (3) modulation of cellular death; (4) modulation of ER-specific apoptosis pathways; (5) modulation of amyloid-2-mediated neurotoxicity; (6) modulation of the NF-kB pathway; and (7) modulation of stress-responsive signaling pathways.

In certain preferred embodiments, polypeptides comprising all or a polypeptide fragment of human PYRIN-1 (SEQ ID NO:5) are useful. The polypeptide can posses one or more biological activities of PYRIN-1, e.g., the ability to enhance ASC activation of NF-kB, the ability to selectively interact with ASC (particularly the PYRIN domain of ASC), the ability to co-localize with ASC in cytoplasmic punctate structures, the ability to activate apoptosis, the ability to activate caspase-mediated apoptosis, and the ability to activate caspase-1. The invention also includes polypeptides consisting of or consisting essentially of such polypeptides as well as isolated nucleic acid molecules encoding such polypeptides.

In certain preferred embodiments, polypeptides comprising all or a polypeptide fragment of human NBS-1 (SEQ ID NO:2) are useful. The polypeptide can posses one or more biological activities of NBS-1. The invention also includes polypeptides consisting of or consisting essentially of such polypeptides as well as isolated nucleic acid molecules encoding such polypeptides.

The NBS-1 or PYRIN-1 proteins of the present invention, or biologically active portions thereof, can be operatively linked to a non-NBS-1 or PYRIN-1 polypeptide (e.g., heterologous amino acid sequences) to form NBS-1 or PYRIN-1 fusion proteins, respectively, for use in various screening assays and other methods of the invention.

Among the nucleic acid molecules useful in the methods of the invention are those that specifically detect NBS-1 or PYRIN-1 nucleic acid molecules, relative to nucleic acid molecules encoding other members of the NBS/LRR superfamily. For example, in one embodiment, a NBS-1 or PYRIN-1 nucleic acid molecule hybridizes under stringent conditions to a nucleic acid molecule comprising the nucleotide sequence of SEQ ID NO:1, SEQ ID NO:3, SEQ ID NO:4, SEQ ID NO:6, or a complement thereof. Such molecules can be, e.g., at least 300 (350, 400, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 3850) nucleotides in length and hybridize under stringent conditions to a nucleic acid molecule comprising the nucleotide sequence shown in SEQ ID NO:1, SEQ ID NO:3, SEQ ID NO:4, SEQ ID NO:6, or a complement thereof. Also useful are nucleic acid molecules which includes a fragment of at least 150 (300, 325, 350, 375, 400, 425, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 3850) nucleotides of the nucleotide sequence shown in SEQ ID NO:1, SEQ ID NO:3, SEQ ID NO:4, SEQ ID NO:6, or a complement thereof.

Other features and advantages of the invention will be apparent from the following detailed description and claims.

BRIEF DESCRIPTION OF THE DRAWINGS

FIGS. 1A-1E depict the cDNA sequence (SEQ ID NO:1) and the predicted amino acid sequence (SEQ ID NO:2) of human NBS-1. The open reading frame of human NBS-1 (SEQ ID NO:1) extends from nucleotide 78 to nucleotide 3176 of SEQ ID NO:1 (SEQ ID NO:3).

FIGS. 4A-4E depict the cDNA sequence (SEQ ID NO:4) and the predicted amino acid sequence (SEQ ID NO:5) of human PYRIN-1. The open reading frame of human PYRIN-1 (SEQ ID NO:4) extends from nucleotide 141 to nucleotide 3240 of SEQ ID NO:4 (SEQ ID NO:6).

FIGS. 8A-8H each depict the alignment of several of the leucine rich repeats within the LRR domain of NBS-1 ((amino acids 726-752 of SEQ ID NO:2 (FIG. 8A), amino acids 782-809 of SEQ ID NO:2 (FIG. 8B), amino acids 811-838 of SEQ ID NO:2 (FIG. 8C), amino acids 839-866 of SEQ ID NO:2 (FIG. 8D), amino acids 868-895 of SEQ ID NO:2 (FIG. 8E), amino acids 896-923 of SEQ ID NO:2 (FIG. 8F), amino acids 925-952 of SEQ ID NO:2 (FIG. 8G), and amino acids 953-979 of SEQ ID NO:2 (FIG. 8H)) with a consensus leucine rich repeat (SEQ ID NO:12) derived from a hidden Markov model. The leucine rich repeats at amino acids 670-697, 698-725, 754-781 and 981-1008 of SEQ ID NO:2 are not depicted.

FIG. 9B depicts an alignment of amino acids 1-90 of human PYRIN-1 (amino acids 1-90 of SEQ ID NO:5 with the pyrin domains of pyrin (33% identity; SEQ ID NO:14), CARD-7 (24% identity; SEQ ID NO:15), ASC (25% identity; SEQ ID NO:16), NBS-1 (24% identity; amino acid residues 1-89 of SEQ ID NO:5), and POP-1 (28% identity; SEQ ID NO:17).

FIGS. 10A-10I each depict the alignment of several of the leucine rich repeats within the LRR domain of PYRIN-1 ((amino acids 740-767 of SEQ ID NO:5 (FIG. 10A), amino acids 769-796 of SEQ ID NO:5 (FIG. 10B), amino acids 797-821 of SEQ ID NO:5 (FIG. 10C), amino acids 826-849 of SEQ ID NO:5 (FIG. 10D), amino acids 854-878 of SEQ ID NO:5 (FIG. 10E), amino acids 883-906 of SEQ ID NO:5 (FIG. 10F), amino acids 911-935 of SEQ ID NO:5 (FIG. 10G), amino acids 940-967 of SEQ ID NO:5 (FIG. 10H), and amino acids 968-991 of SEQ ID NO:5 (FIG. 10I)) with a consensus leucine rich repeat (SEQ ID NO:13) derived from a hidden Markov model.

DETAILED DESCRIPTION OF THE INVENTION

Described below are studies demonstrating that PYRIN-1 interacts with ASC, activates NF-kB, and when co-expressed with ASC synergistically activates caspase-1. The pyrin domain of PYRIN-1 is shown to play a central role in these functions, and the LRR domain of PYRIN-1 is shown to act as a negative modulator of the PYRIN-1-mediated activation of NF-kB. The studies demonstrate that PYRIN-1 is a apoptotic signaling molecule that acts in apoptosis and inflammation.

A nucleotide sequence encoding a human NBS-1 protein is shown in FIGS. 1A-1E (SEQ ID NO:1; SEQ ID NO:3 includes the open reading frame only). A predicted amino acid sequence of human NBS-1 protein is also shown in FIGS. 1A-1E (SEQ ID NO:2).

A nucleotide sequence encoding a human PYRIN-1 protein is shown in FIGS. 4A-4E (SEQ ID NO:4; SEQ ID NO:6 includes the open reading frame only). A predicted amino acid sequence of human PYRIN-1 protein is also shown in FIGS. 4A-4E (SEQ ID NO:5).

Identification of Human NBS-1

A cDNA encoding human NBS-1 was identified by searching a proprietary cDNA sequence database in an effort to identify sequences that might encode an NBS. This search led to the identification of a cDNA that was used in 5' RACE to identify a complete open reading frame encoding the protein later named NBS-1.

FIGS. 1A-1E depict the sequence of a 3431 nucleotide cDNA (SEQ ID NO:1) which includes a predicted open reading frame (SEQ ID NO:3; nucleotides 78-3176 of SEQ ID NO:1) encoding a 1033 amino acid human NBS-1 protein (SEQ ID NO:2). Human NBS-1 is predicted to be an intracellular protein having a molecular weight of 113.6 kD, prior to post-translational modification.

The predicted amino acid sequence of human NBS-1 was compared to amino acid sequences of known proteins and various motifs were identified. The 1033 amino acid human NBS-1 protein includes five N-glycosylation sites (e.g., about amino acid residues 637-640, 679-682, 782-785, 789-952, and 952-955 of SEQ ID NO:2); 11 protein kinase C phosphorylation sites (amino acids 79-81, 105-107, 218-220, 307-309, 379-381, 563-565, 669-671, 806-808, 983-985, 986-988, and 1016-1018 of SEQ ID NO:2); 16 casein kinase II phosphorylation sites (amino acids 13-16, 55-58, 105-108, 218-221, 229-232, 512-515, 570-573, 584-587, 639-642, 643-646, 650-653, 669-672, 711-714, 791-794, 942-945, and 1027-1030 of SEQ ID NO:2); two tyrosine kinase phosphorylation sites (amino acids 317-325 and 858-866 of SEQ ID NO:2); and 10 N-myristoylation sites (amino acids 188-193, 266-271, 291-296, 367-372, 417-422, 446-451, 566-571, 675-680, 761-766, and 982-987 of SEQ ID NO:2)

Figure 2:
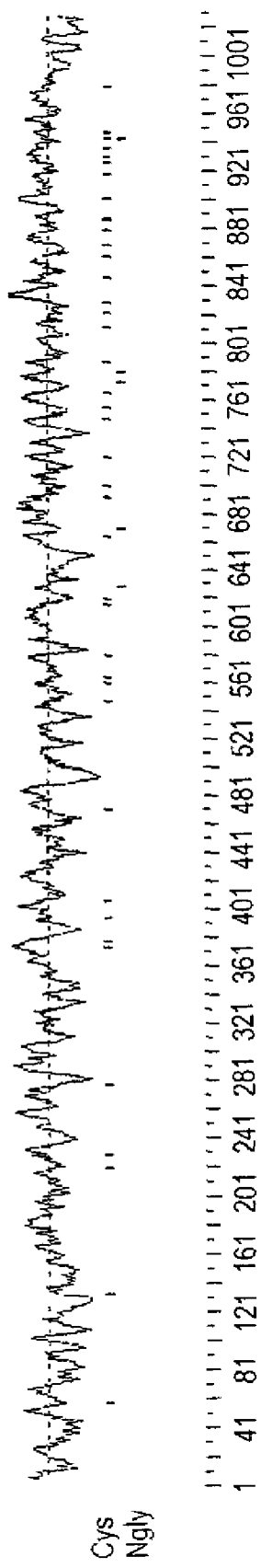
FIG. 2 depicts a hydropathy plot of human NBS-1. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 2 depicts a hydropathy plot of human NBS-1. Relatively hydrophobic residues are above the dashed horizontal line, and relatively hydrophilic residues are below the dashed horizontal line. Potential N-glycosylation sites (Ngly) and cysteine residues are indicated by short vertical lines just below the hydropathy trace.

Figure 3:
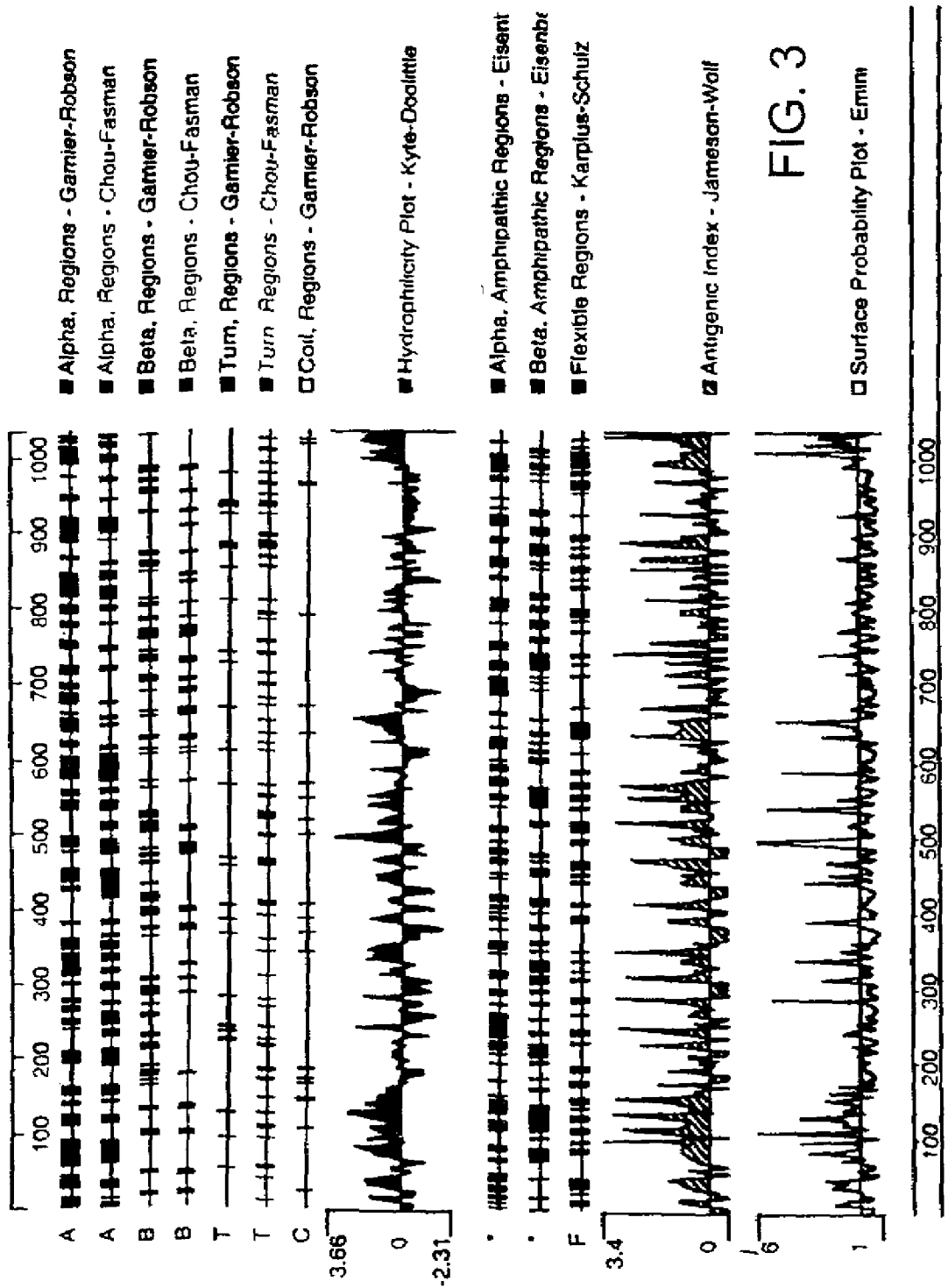
FIG. 3 depicts a plot showing the predicted structural features of a portion of human NBS-1. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of a portion of human NBS-1 is presented in FIG. 3. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

Analysis of the predicted NBS-1 amino acid sequence showed it to contain a pyrin domain (about amino acids 3-79 of SEQ ID NO:2) a nucleotide binding site (NBS; about amino acid residues 174-605 of SEQ ID NO:2) and 12 leucine rich repeats (about amino acids residues 670-697, 698-725, 726-752, 754-781, 782-809, 811-838, 839-866, 868-895, 896-923, 925-952, 953-979, and 981-1008 of SEQ ID NO:2) which form a LRR domain (about amino acids 670-1008 of SEQ ID NO:2). Within the predicted NBS there is a kinase 1a domain (P-loop) (about amino acids 180-195 of SEQ ID NO:2), a kinase 2 domain (Walker B box) (about amino acids 249-264 of SEQ ID NO:2), and a kinase 3a domain (about amino acids 302-313 of SEQ ID NO:2).

Figure 7:
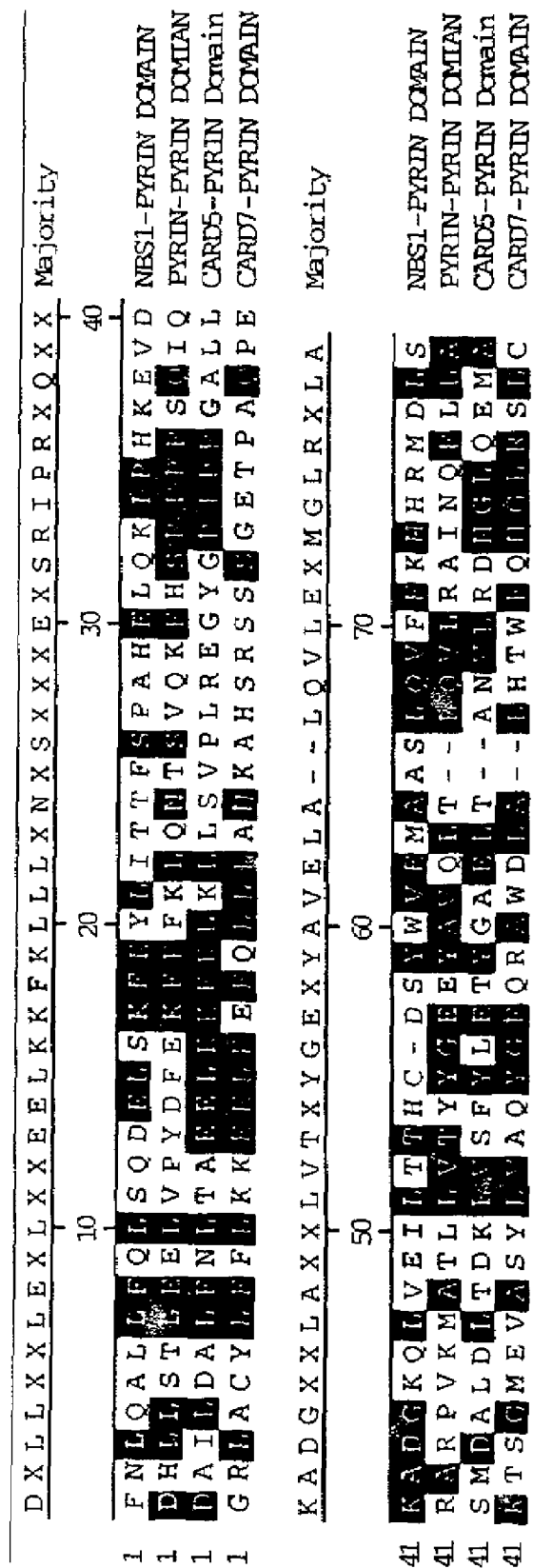
FIG. 7 depicts an alignment of amino acids 3-79 of human NBS-1 (amino acid residues 3-79 of SEQ ID NO:2) with the pyrin domains of pyrin (SEQ ID NO:7), CARD-5 (SEQ ID NO:8), and CARD-7 (SEQ ID NO:9). A consensus pyrin domain sequence (SEQ ID NO:10) is shown above the alignment.

FIG. 7 depicts an alignment of amino acids 3-79 of human NBS-1 (amino acid residues 3-79 of SEQ ID NO:2) with the pyrin domains of pyrin (SEQ ID NO:7), CARD-5 (SEQ ID NO:8), and CARD-7 (SEQ ID NO:9). A consensus pyrin domain sequence (SEQ ID NO:10) is shown above the alignment.

FIGS. 8A-8H each depict an alignment of individual leucine rich repeats within the LRR domain of NBS-1 ((amino acids 726-752 of SEQ ID NO:2 (FIG. 8A), amino acids 782-809 of SEQ ID NO:2 (FIG. 8B), amino acids 811-838 of SEQ ID NO:2 (FIG. 8C), amino acids 839-866 of SEQ ID NO:2 (FIG. 8D), amino acids 868-895 of SEQ ID NO:2 (FIG. 8E), amino acids 896-923 of SEQ ID NO:2

(FIG. 8F), amino acids 925-952 of SEQ ID NO:2 (FIG. 8G), and amino acids 953-979 of SEQ ID NO:2 (FIG. 8H)) with a consensus LRR (SEQ ID NO:12) derived from a hidden Markov model. The leucine rich repeats present at amino acids 670-697, 698-725, 754-781 and 981-1008 of SEQ ID NO:2 are not depicted in FIGS. 8A-8H. HMMs can be used to do multiple sequence alignment and very sensitive database searching, using statistical descriptions of a sequence family's consensus. Information on HMM searches is available, for example, on the Internet at www.hmmr.wustl.edu. In the alignments of FIGS. 8A-8H a single letter amino acid designation on the line between the NBS-1 sequence and the HMM-generated consensus sequence indicates an exact match between the two. A "+" on this middle line indicates a conservative substitution at the particular residue of NBS-1.

Identification of Human PYRIN-1

A cDNA encoding human PYRIN-1 was identified by searching a proprietary cDNA sequence database with a sequence encoding the pyrin domain of NBS-1. This search led to the identification of a 3.8-kilobase cDNA (clone jthPa091c07t1) from a human placenta library encoding a protein that was named PYRIN-1. This protein is also referred to as PYRIN-containing Apaf1-like protein 1 (PY-PAF-1).

FIGS. 4A-4E depict the sequence of a 3857 nucleotide cDNA (SEQ ID NO:4) which includes a predicted open reading frame (SEQ ID NO:6; nucleotides 141-3240 of SEQ ID NO:4) encoding a 1034 amino acid human PYRIN-1 protein (SEQ ID NO:5). Human PYRIN-1 is predicted to be an intracellular protein having a predicted molecular mass of 118 kDa.

The predicted amino acid sequence of human PYRIN-1 was compared to amino acid sequences of known proteins and various motifs were identified. The 1034 amino acid human PYRIN-1 protein includes three N-glycosylation sites (e.g., about amino acid residues 654-657, 911-914, and 950-953 of SEQ ID NO:5); four cAMP- and cGMP-dependent protein kinase phosphorylation sites (e.g., about amino acid residues 164-167, 290-293, 592-595, and 970-973 of SEQ ID NO:5); nine protein kinase C phosphorylation sites (e.g., about amino acid residues 3-5, 44-46, 266-268, 347-349, 426-428, 433-435, 595-597, 656-658, and 968-970 of SEQ ID NO:5); 12 casein kinase II phosphorylation sites (e.g., about amino acid residues 110-113, 177-180, 269-272, 522-525, 588-591, 624-627, 657-660, 740-743, 750-753, 921-924, 1014-1017, and 1018-1021 of SEQ ID NO:5); six N-myristoylation sites (e.g., about amino acid residues 93-98, 227-232, 491-496, 717-722, 888-893, and 919-924 of SEQ ID NO:5); an RGD cell attachment sequence (e.g., about amino acid residues 325-327 of SEQ ID NO:5); an ATP/GTP-binding site motif A (P-loop) (e.g., about amino acid residues 224-231 of SEQ ID NO:5); a leucine zipper pattern (e.g., about amino acid residues 816-837 of SEQ ID NO:5); a peroxisomal targeting signal (e.g., about amino acid residues 618-626 of SEQ ID NO:5); and 10 dileucine motifs (e.g., about amino acid residues 448-449, 533-534, 559-560, 606-607, 815-816, 823-824, 929-930, 934-935, 962-963, and 997-998 of SEQ ID NO:5).

Figure 5:
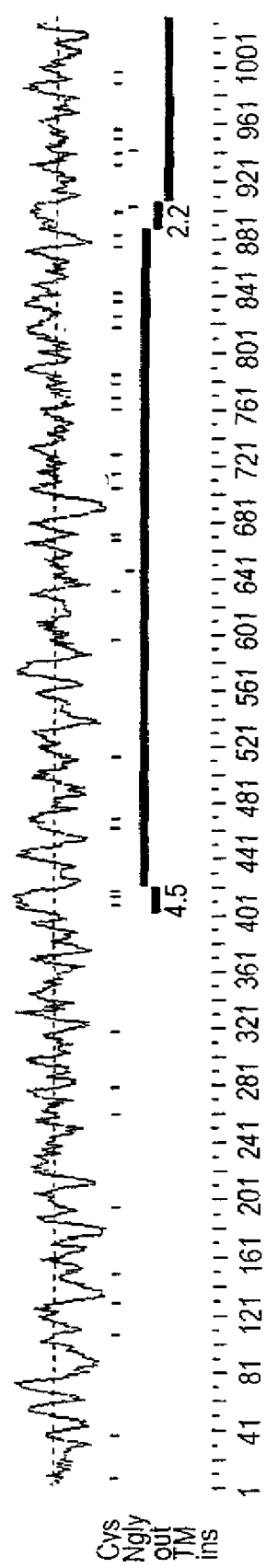
FIG. 5 depicts a hydropathy plot of a portion of human PYRIN-1. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 5 depicts a hydropathy plot of human PYRIN-1. Relatively hydrophobic residues are above the dashed horizontal line, and relatively hydrophilic residues are below the dashed horizontal line. Potential N-glycosylation sites (Ngly) and cysteine residues are indicated by short vertical lines just below the hydropathy trace.

Figure 6:
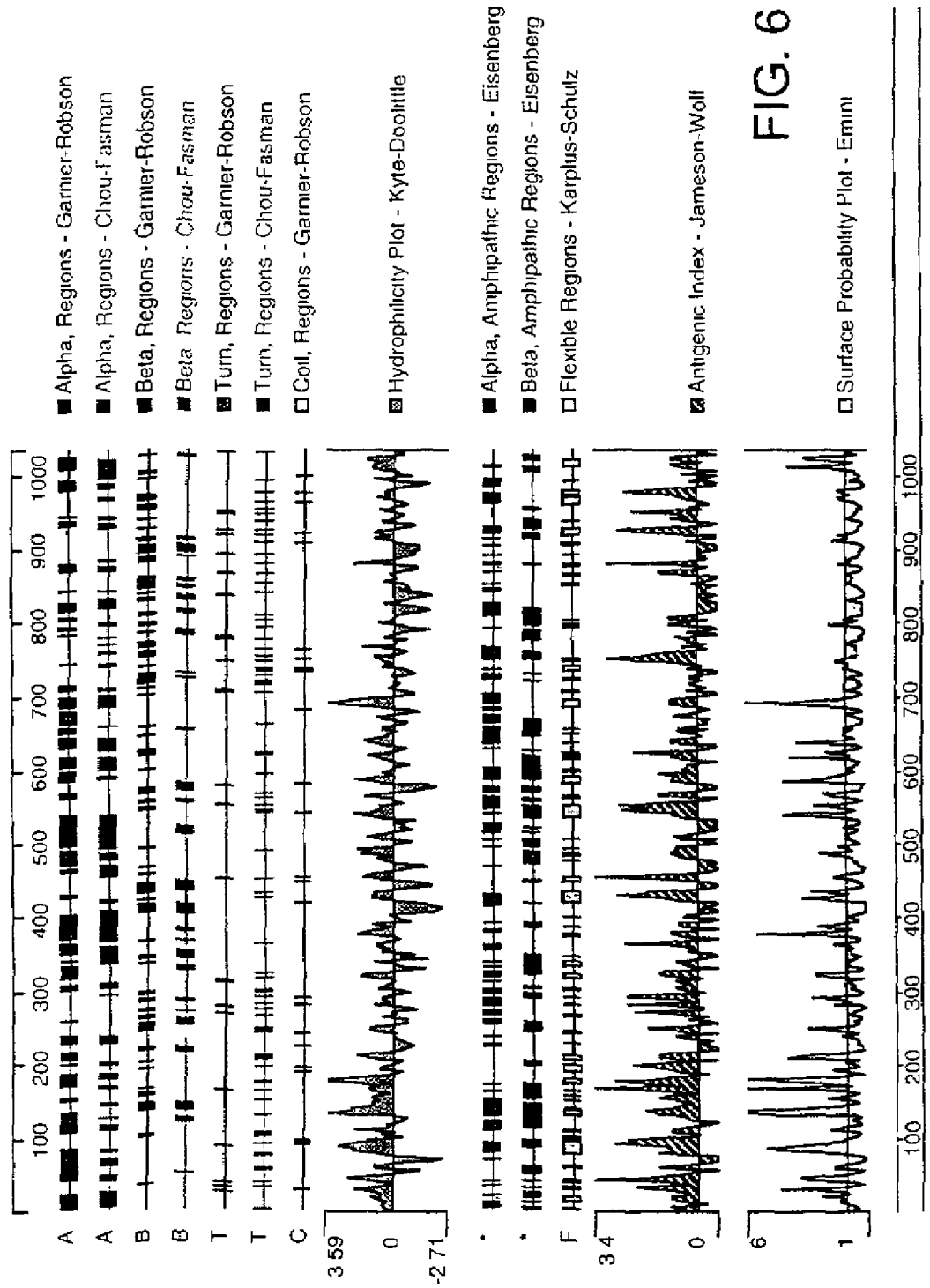
FIG. 6 depicts a plot showing the predicted structural features of a portion of human PYRIN-1. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of human PYRIN-1 is presented in FIG. 6. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

Analysis of the predicted PYRIN-1 amino acid sequence showed it to contain a pyrin domain (about amino acids 1-90 of SEQ ID NO:5) a nucleotide binding site (NBS; about amino acid residues 263-357 of SEQ ID NO:5) and nine leucine rich repeats (LRRs; about amino acids residues 740-767, 769-796, 797-821, 826-849, 854-878, 883-906, 911-935, 940-967, and 968-991 of SEQ ID NO:5) which form a LRR domain (about amino acids 740-991 of SEQ ID NO:5). Within the predicted NBS there is a kinase 1a domain (P-loop) (about amino acids 224-233 of SEQ ID NO:5), a kinase 2 domain (Walker B box) (about amino acids 290-306 of SEQ ID NO:5), and a kinase 3a domain (about amino acids 344-355 of SEQ ID NO:5).

An expanded NBS domain encompasses amino acids 219-434 of SEQ ID NO:5. This NBS domain belongs to the NACHT subfamily of NTPases and contains all seven signature motifs, including the P-loop and the $Mg^{2+}$-binding site (Koonin et al. (2000) *Trends Biochem. Sci* 25:223-224). The seven signature motifs are located a amino acids 219-241, 248-278, 282-305, 326-351, 402-422, 489-504, and 515-534 of SEQ ID NO:5.

Figure 9A:
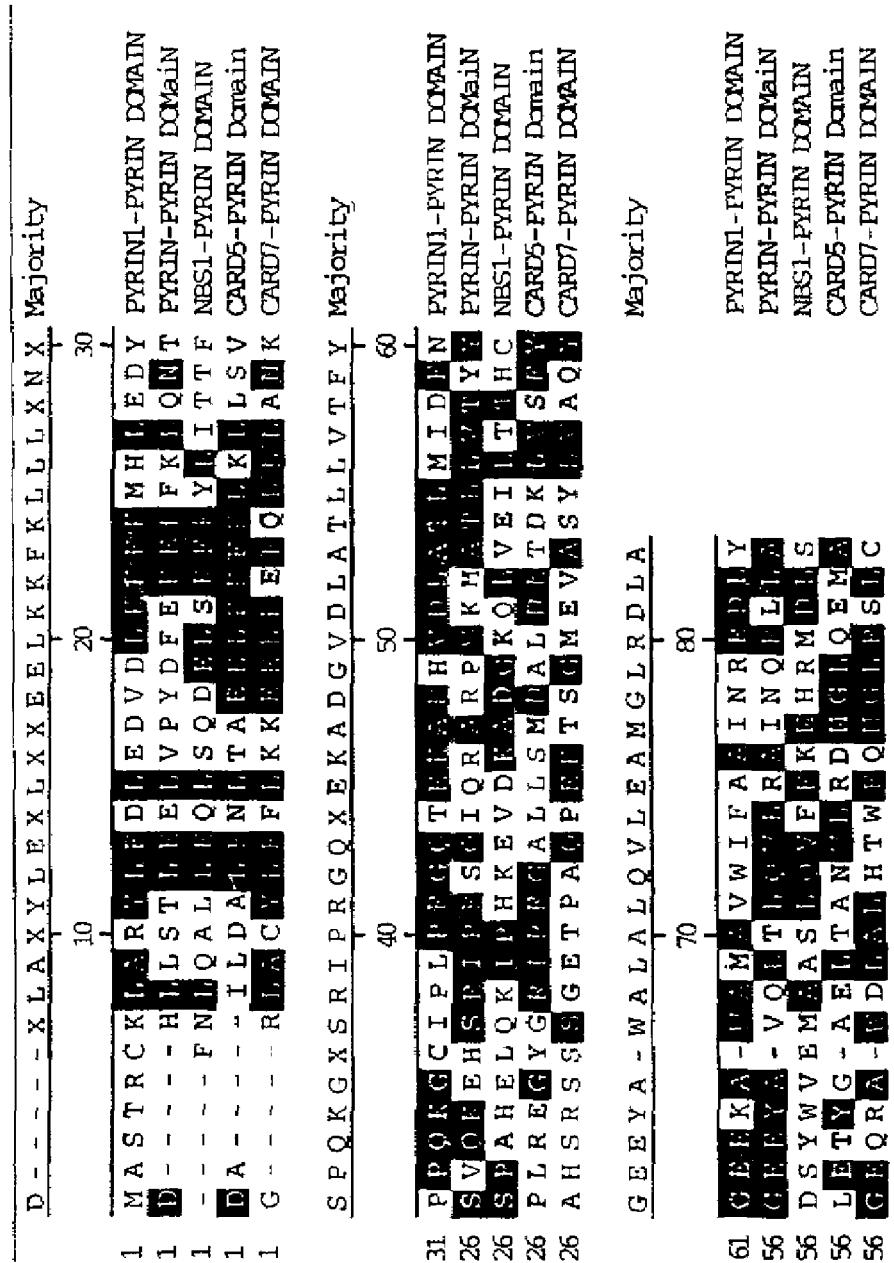
FIG. 9A depicts an alignment of amino acids 1-82 of human PYRIN-1 (amino acid residues 1-82 of SEQ ID NO:5) with the pyrin domains of pyrin (SEQ ID NO:7), NBS-1 (amino acid residues 3-79 of SEQ IID NO:2), CARD-5 (SEQ ID NO:8), and CARD-7 (SEQ ID NO:9). A consensus pyrin domain sequence (SEQ ID NO:11) is shown above the alignment.

FIG. 9A depicts an alignment of amino acids 1-82 of human PYRIN-1 (amino acid residues 1-82 of SEQ ID NO:5) with the pyrin domains of pyrin (SEQ ID NO:7), CARD-5 (SEQ ID NO:8), and CARD-7 (SEQ ID NO:9). A consensus pyrin domain sequence (SEQ ID NO:11) is shown above the alignment.

Figure 9B:
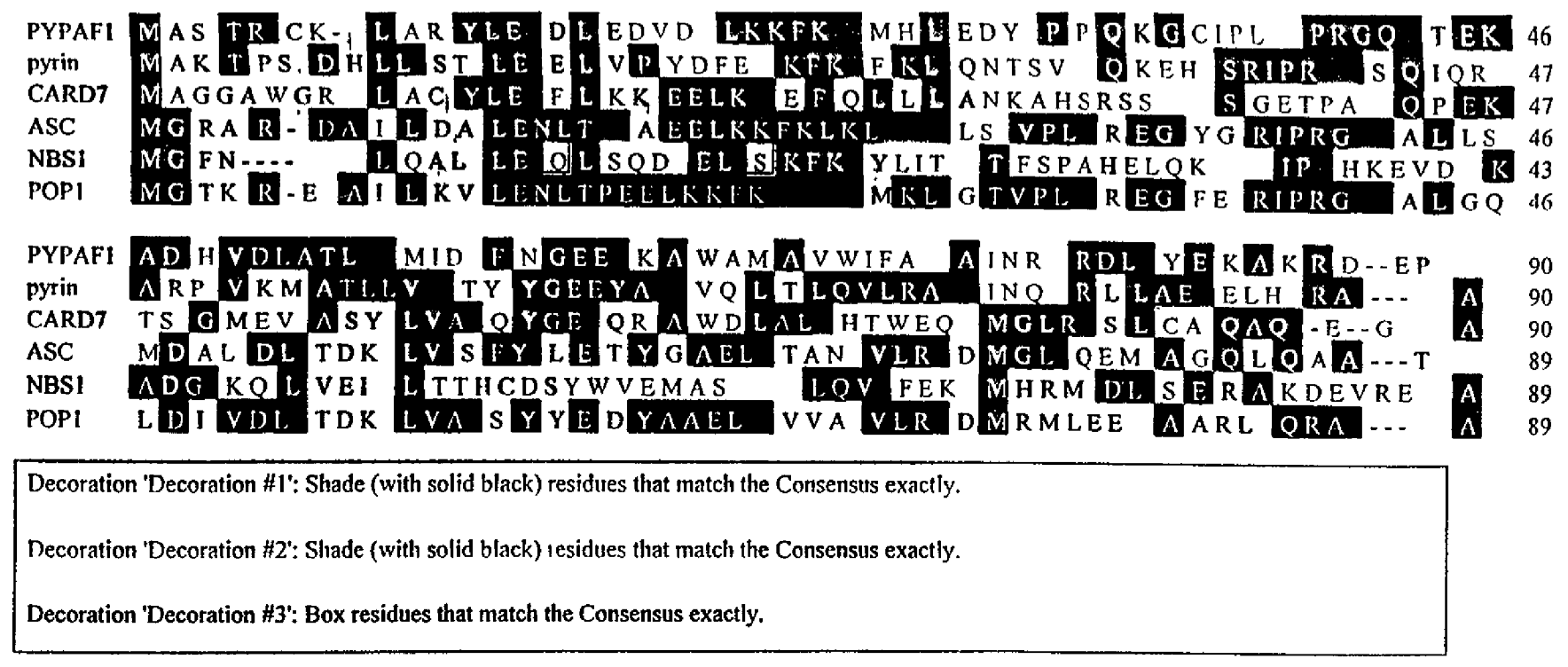

FIG. 9B depicts an alignment of amino acids 1-90 of human PYRIN-1 (amino acids 1-90 of SEQ ID NO:5 with the pyrin domains of pyrin (33% identity), CARD-7 (24% identity), ASC (25% identity), NBS-1 (24% identity), and POP-1 (28% identity).

FIGS. 10A-10I each depict an alignment of individual leucine rich repeats within the LRR domain of PYRIN-1 ((about amino acids 740-767 of SEQ ID NO:5 (FIG. 10A), amino acids 769-796 of SEQ ID NO:5 (FIG. 10B), amino acids 797-821 of SEQ ID NO:5 (FIG. 10C), amino acids 826-849 of SEQ ID NO:5 (FIG. 10D), amino acids 854-878 of SEQ ID NO:5 (FIG. 10E), amino acids 883-906 of SEQ ID NO:5 (FIG. 10F), amino acids 911-935 of SEQ ID NO:5 (FIG. 10G), amino acids 940-967 of SEQ ID NO:5 (FIG. 10H), and amino acids 968-991 of SEQ ID NO:5 (FIG. 10I)) with a consensus LRR (SEQ ID NO:13) derived from a hidden Markov model.

Chromosomal Mapping of PYRIN-1

A search of the HTG genomic database, identified a single BAC clone, RP11-433K2, containing the partial genomic sequence of PYRIN-1. This BAC clone maps to chromosome 1 at q44.

Expression of PYRIN-1

Northern blot analysis carried out using a CLONTECH Tissue Blots (La Jolla, Calif.) revealed that PYRIN-1 is expressed n peripheral blood lymphocytes as a 3.8-kilobase transcript, indicating a role for this protein in inflammatory signaling. Expression profiling using a multi-tissue expression array showed no detectable expression of PYRIN-1 in 75 other tissues and cancer cell lines, indicating a role in inflammatory signaling. To determine the cells that express PYRIN-1 mRNA, peripheral blood leukocytes were fractionated into distinct cell populations. RT-QPCR analysis showed PYRIN-1 to be predominantly expressed in monocytes. Lower level expression was observed in T cells and granulocytes. No expression was detected in macrophages and B-cells.

Interaction of PYRIN-1 with ASC

By analogy to other NBS/LRR family members such as CARD-4 and Nod2, the N-terminal PYRIN domain of PYRIN-1 was predicted to interact with another PYRIN-domain-containing protein to activate downstream signaling pathways. ASC is a small protein with an N-terminal PYRIN domain that also contains a C-terminal CARD domain (Masumoto et al. (1999) *J. Biol Chem.* 274:33835). ASC is also called CARD-5 (CARD-5 is described in U.S. patent application Ser. No. 09/841,879, filed Apr. 24, 2001, U.S. patent application Ser. No. 09/728,721, filed Dec. 1, 2000, U.S. patent application Ser. No.09/340,620, filed Jun. 28, 1999, the entire contents of which are incorporated by reference). Its bipartite domain structure indicates that ASC might function as an adaptor protein. To investigate whether PYRIN-1 interacts with ASC a mammalian two-hybrid assay was used to examine the interaction between the N-terminal PYRIN domains of both proteins.

For mammalian two-hybrid assays, pCMV-PYRIN-1-PYRIN/BD and pCMV-ASC-PYRIN/AD plasmids were constructed by inserting the PYRIN domains of PYRIN-1 (residues 1-116) and ASC (residues 1-110) into pCMV-BD and pCMV-AD vectors, respectively (Stratagene; La Jolla, Calif.). A plasmid expressing the CARD domain of ASC fused to the activation domain of NF-kB was prepared as described previously (Bertin et al. (2001) *J Biol Chem.* 276:11877-11882).

The plasmids were introduced into 293T cells transfected with the mammalian two-hybrid reporter construct pFR-Luc firefly reporter (Stratagene) or pRL-TK Renilla reporter (Promega). The PYRIN domain of PYRIN-1 fused to the DNA-binding domain of GAL4 was screened against the PYRIN and CARD domains of ASC fused to the activation domain of murine NF-kB. After 24 h, cells were collected and assayed for relative luciferase activity as a measure of protein-protein interaction using the Dual-Luciferase express reporter assay system (Promega).

This study revealed that the PYRIN domain of PYRIN-1 interacts with the PYRIN domain of ASC resulting in a 11-fold increase in relative luciferase activity. In contrast, co-expression of the PYRIN domain of PYRIN-1 with the CARD domain of ASC failed to activate luciferase expression indicating that the PYRIN domain of PYRIN-1 interacts selectively with the PYRIN domain of ASC. These findings identify ASC as a putative signaling partner of PYRIN-1.

Additional mammalian two-hybrid assays were conducted to investigate the possible interaction of the PYRIN domain of PYRIN-1 with the PYRIN domain of other proteins. For these mammalian two-hybrid assays, pCMV-PYRIN/AD plasmids were constructed by inserting individual PYRIN domains into pCMV/AD (Stratagene). In this study PYRIN domains from ASC (residues 1-110), CARD-7 (residues 2-112), PYRIN-1 (residues 1-116), NBS1 (residue 1-115), and POP1 (Pyrin-4; residues 1-89) were analyzed. Similarly, pCMV-PYRIN-1-PYRIN/BD and pCMV-ASC-CARD/AD plasmids were constructed by inserting amino acid 1-116 of PYRIN-1 and the CARD domain of ASC (residues 92-195) into pCMV-BD and pCMV-AD, respectively. These mammalian two-hyrbid assays demonstrated that the PYRIN domain of PYRIN-1 interacts with the PYRIN domain of ASC, resulting in a 16-fold increase in relative luciferase activity. However, a truncated PYRIN-1 lacking the PYRIN domain failed to bind to the PYRIN domain of other family members (CARD-7, ASC and POP1) indicating that the PYRIN domain of PYRIN-1 interacts selectively with the PYRIN domain of ASC. Furthermore, the PYRIN domain of PYRIN-1 failed to interact with the CARD domain of ASC. Taken together, these findings identify ASC as a putative signaling partner of PYRIN-1 and demonstrate that PYRIN-PYRIN interactions between family members can be highly selective.

Co-localization of PYRIN-1 and ASC

Co-localization studies were performed to further examine the interactions between PYRIN-1 and ASC. These studies were carried out by expressing HA-tagged PYRIN-1 and FLAG-tagged ASC in Vero cells using recombinant adenoviruses, and then detecting the proteins using a mixture of anti-HA and anti-FLAG antibodies. Plasmids expressing either PYRIN-1 with a C-terminal FLAG epitope or ASC with a C-terminal HA epitope were constructed using pCMV-Tag 4a (Stratagene) and pCI (Promega), respectively.

When expressed alone, PYRIN-1 and ASC exhibited a distinct pattern of cellular localization. Whereas ASC localized to speck-like structures (Masumoto et al. (1999) *J. Biol. Chem.* 274:33835-33838), PYRIN-1 showed a cytoplasmic distribution that excluded the nucleus. However, when the two proteins were expressed in the same cell, PYRIN-1 was found to co-localize with the ASC speck-like structures. This finding confirms the interaction of PYRIN-1 with ASC previously observed by mammalian two-hybrid analysis and suggests that PYRIN-1 is recruited to a cytoplasmic signaling complex with ASC.

Additional co-localization studies were carried out using FLAG-tagged PYRIN-1 and FLAG-tagged PYRIN-1 mutants and HA-tagged ASC. For these studies, plasmids expressing either full-length PYRIN-1 (PYRIN-1-FL) or a PYRIN-1 truncation mutant lacking the PYRIN domain (PYRIN-1ΔPYRIN; residues 90-1034) with a C-terminal FLAG epitope were constructed using pCMV-Tag 4a (Stratagene). Plasmids expressing either a PYRIN-1 truncation mutant lacking the LRR domain (PYRIN-1ΔLRR; residues 1-739) with a C-terminal FLAG epitope or ASC with a C-terminal HA epitope were constructed using pCI (Promega). FLAG-tagged PYPAF1 and HA-tagged ASC were expressed in 293T embryonic kidney cells and detected using a mixture of anti-HA and anti-FLAG antibodies. When expressed alone, the two proteins exhibited a distinct pattern of cellular localization. Whereas ASC localizes to cytoplasmic punctate structures, full-length PYRIN-1 (PYRIN-1-FL) showed a broad cytoplasmic distribution that excluded the nucleus. However, when the two proteins were co-expressed, PYRIN-1-FL was found to co-localize with ASC. To determine the regions of PYRIN-1 necessary for co-localization, the ability of PYRIN-1 mutants lacking either the N-terminal PYRIN domain (PYRIN-1ΔPYRIN) or C-terminal LRRs (PYRIN-1ΔLRR) to be recruited to the ASC punctate structures was examined. When expressed alone, PYRIN-1ΔPYRIN showed a broad cytoplasmic distribution similar to PYRIN-1-FL. However, PYRIN-1ΔPYRIN failed to co-localize with the ASC punctate structures, demonstrating that the PYRIN domain of PYRIN-1 is necessary for recruitment. In contrast, PYRIN-1ΔLRR co-localized with ASC indicating that the C-terminal LRRs of PYRIN-1 were dispensable for recruitment.

Taken together, the localization studies provide additional evidence that the N-terminal PYRIN domain of PYRIN-1 mediates the assembly of a PYRIN-1/ASC complex.

PYRIN-1 Activates ASC Resulting in Increased NF-kB Activity

The ability of PYRIN-1 to activate NF-kB was investigated using a NF-kB activity assay described previously (Wang et al. (2001) *J. Biol. Chem.* 276:21405-21409). Briefly, 293T cells transfected with pNF-kB luciferase reporter (Stratagene), a transfection efficiency control pRL-TK Renilla reporter (Promega), and expression plasmids. Cells were harvested and firefly and Renilla luciferase activities were determined using the Dual-Luciferase reporter assay system (Promega).

Figure 14:
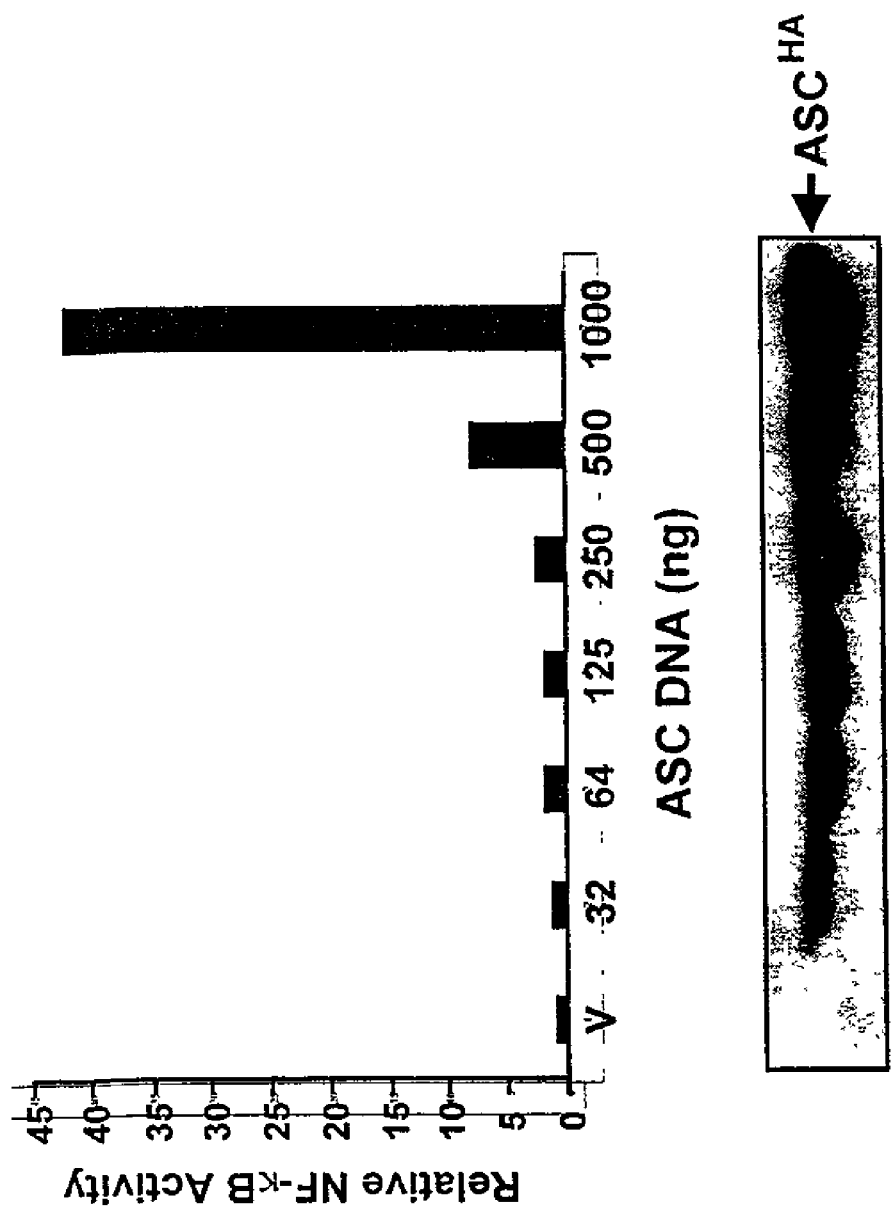
FIG. 14 is a graph depicting the results of an NF-kB activity assay showing that ASC induces NF-kB activity. In this assay plasmids expressing ASC were transfected into 293T cells and induction of NF-kB activity was assessed by measuring relative luciferase activity.
Figure 15:
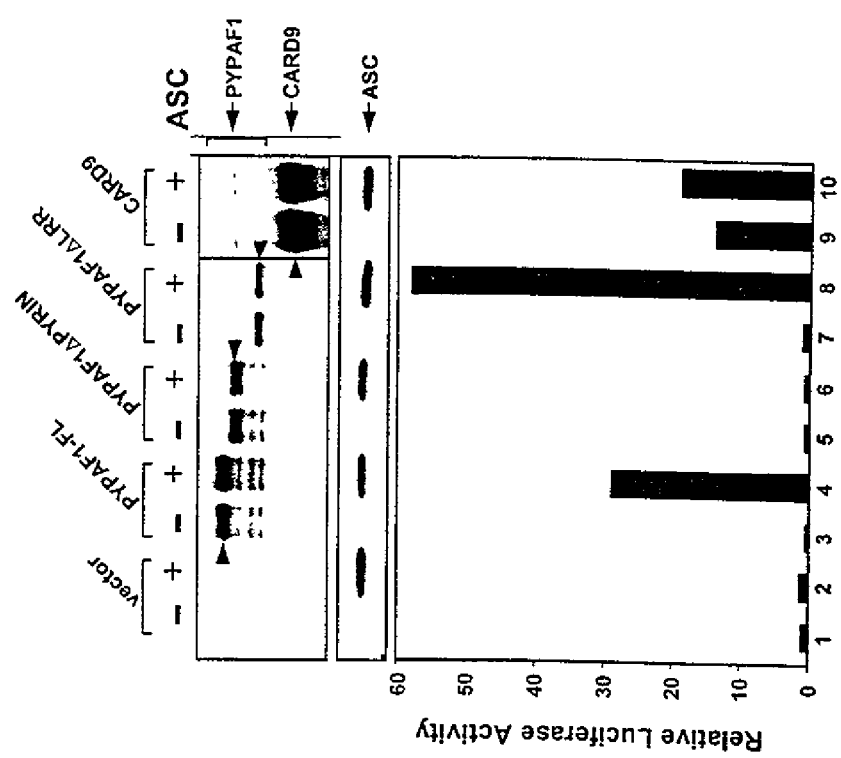
FIG. 15 depicts the results of an NF-kB activity assay showing that PYRIN-1 synergizes with ASC to induce NF-kB. In this study, 293T cells were transfected with plasmids expressing PYRIN-1-FL, PYRIN-1ΔPYRIN, PYPAF1ΔLRR, or CARD-9 (500 ng) with or without ASC (32 ng). The amount of DNAs in each transfection was kept constant by addition of empty vectors. Relative luciferase activities were then determined as a measure of NF-kB activity (lower panel). Immunoblot analysis was performed to monitor expression of PYRIN-1 or CARD-9 (upper panel) and ASC (middle panel).
Figure 16:
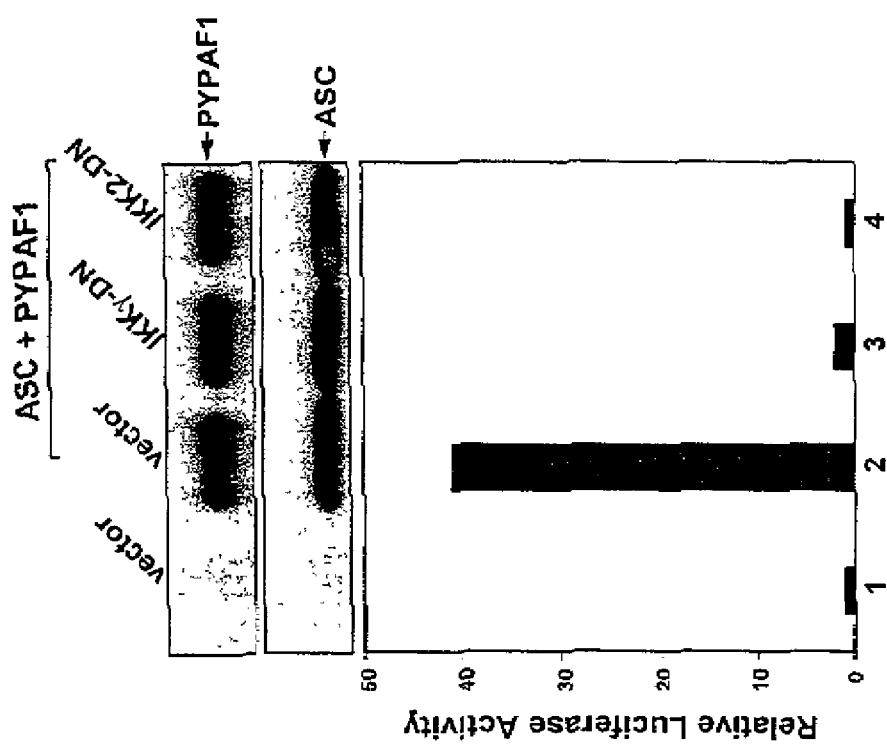
FIG. 16 depicts the results of an NF-kB activity assay showing that PYRIN-1 and ASC activate NF-kB through the IKK complex. In this study 293T cells were transfected with a plasmid expressing ASC (32 ng) and a plasmid expressing PYRIN-1 (500 ng) and either empty vector (500 ng) or a plasmid expressing dominant negative mutants of IKKγ (IKKγ-DN), or IKK2 (IKK2-DN). Immunoblot analysis was performed to monitor expression of PYRIN-1 (upper panel) and ASC (middle panel). Relative luciferase activities were measured as described (lower panel).

When expressed in 293T cells, PYRIN-1 failed to induce NF-kB activity at all protein levels. However, ASC induced NF-kB activity 40 to 50-fold when expressed at high protein levels (FIG. 14). Because PYRIN-1 interacts with ASC, the effect of co-expression of PYRIN-1 and ASC on NF-kB activity was investigated. When ASC was expressed at low protein levels that did not activate NF-kB, co-expression with PYRIN-1 resulted in a 30-fold increase in NF-kB activity (FIG. 15, lane 4). Immunoblot analysis revealed that ASC protein levels were not increased when co-expressed with PYRIN-1, demonstrating that the activation of NF-kB was not due to increased levels of ASC (FIG. 15, lanes 2 and 4). This synergistic effect on NF-kB activity was specific for PYRIN-1 since co-expression of ASC with Apaf1 failed to increase NF-kB activity. These data demonstrate that PYRIN-1 functions as an activator of ASC activity and is an upstream regulator of NF-kB signaling.

NF-kB signaling occurred through the IKK complex because dominant-negative versions of IKK-γ and IKK-2 blocked the ability of PYRIN-1 to synergistically activate NF-kB FIG. 26, lanes 3 and 4). To determine the role of individual domains in NF-kB signaling, the ability of the PYRIN-1 truncation mutants to activate NF-kB was investigated. The N-terminal PYRIN domain of PYRIN-1 was essential for NF-kB signaling, since deletion of this domain (PYRIN-1ΔPYRIN) eliminated the synergistic induction of NF-kB activity (FIG. 15, lane 6). Immunoblot analysis revealed that PYRIN-1ΔPYRIN was expressed at levels similar to that of PYRIN-1, indicating that loss of function was not due to reduced protein levels (FIG. 15, upper panel). In contrast, deletion of the C-terminal domain showed a 2-fold increase in the synergistic activation of NF-kB relative to full-length protein suggesting that the LRRs may function as a negative regulator of PYRIN-1 activity (FIG. 15, lane 8). To confirm that the synergistic effect was specific for PYRIN-9, ASC was co-expressed with CARD-9, a CARD-containing NF-kB activator (Bertin at al. (2000) *J. Biol. Chem.* 275:41082). When expressed alone, CARD-9 induced NF-kB activity 15-20-fold compared with empty vector (FIG. 15, lane 9). However, when CARD-9 and ASC were co-expressed, CARD-9 failed to synergistically activate ASC-induced NF-kB activity (FIG. 15, lane 10). Taken together, these data demonstrate that PYRIN-1 functions as an activator of ASC activity and is an upstream regulator of NF-kB signaling.

Expression of PYRIN-1 in Immune System Cells and Arthritis

Figure 17:
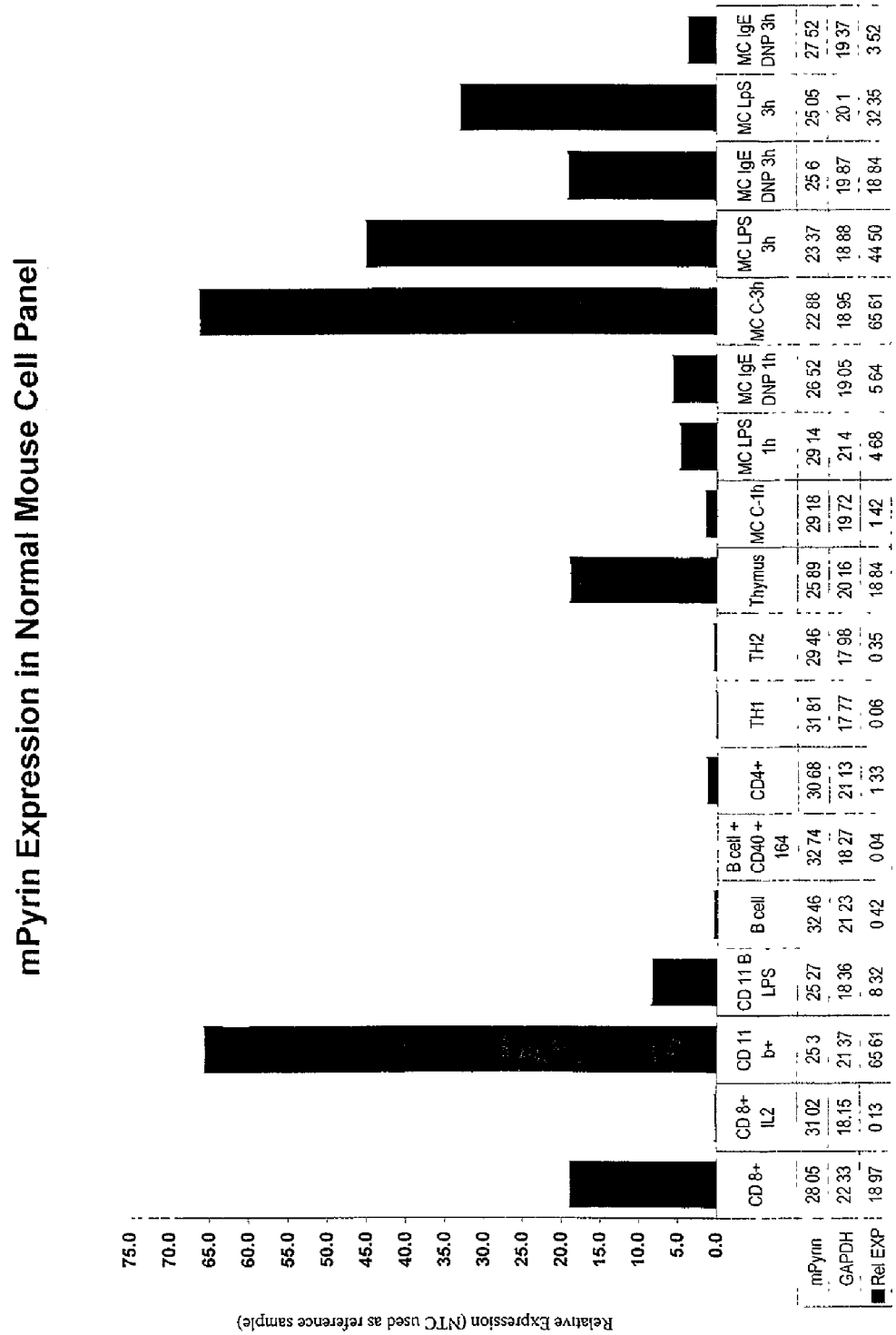
FIG. 17 depicts the results of a PYRIN-1 mRNA assay in various immune cells.

FIG. 17 is a graph depicting the results of a PYRIN-1 mRNA expression assay in various immune system cells. As can be seen from these results, PYRIN-1 is expressed at a higher level in CD8+ cells, CD11 b+ cells, MC cells treated with LPS, MC cells treated with IgE, and certain other cell types.

Figure 18:
FIG. 18 depicts the results of a assay measuring expression of PYRIN-1 in a murine ABT model of rheumatoid arthritis.
Figure 19:
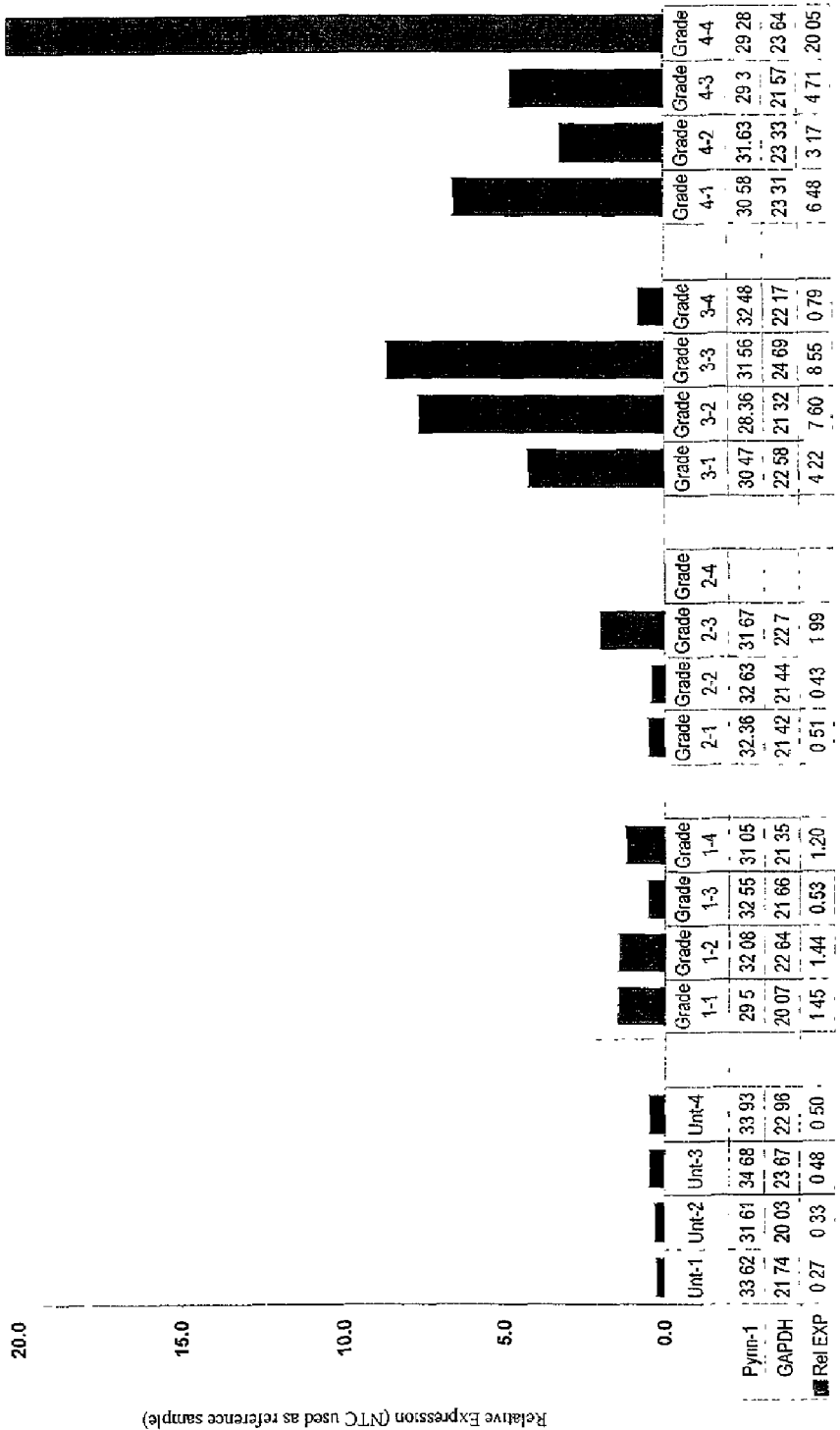
FIG. 19 depicts the results of a assay measuring expression of PYRIN-1 in a murine CIA model of rheumatoid arthritis.

FIGS. 18 and 19 depict the results of PYRIN-1 expression assays in two different murine models of rheumatoid arthritis as can be seen from these results, PYRIN-1 is elevated in rheumatoid arthritis, suggesting that inhibitors of PYRIN-1 expression or activity could be used to treat arthritis.

PYRIN-1 is an Apoptotic Signaling Molecule

PYRIN-containing proteins have been proposed to function in apoptotic signaling. Accordingly, the ability of PYRIN-1 to induce apoptosis when expressed in cells was investigated. Adenoviruses expressing either PYRIN-1 or ASC were generated as described previously (Geddes et al. (2001) *Biochem Biophys. Res. Commun.* 284:77-82). For apoptosis assays, Vero cells were transfected with recombinant adenovirus (20 plaque forming units per cell) expressing either KGFP or PYRIN-1/KGFP with or without z-VAD-fmk (100 μM) and fixed at 56 h. The nuclei were then stained with Hoescht 33342 and the percentage of apoptotic versus healthy nuclei in transfected cells was determined. Levels of apoptosis were determined as described previously (Geddes et al. (2001) supra).

Figure 11:
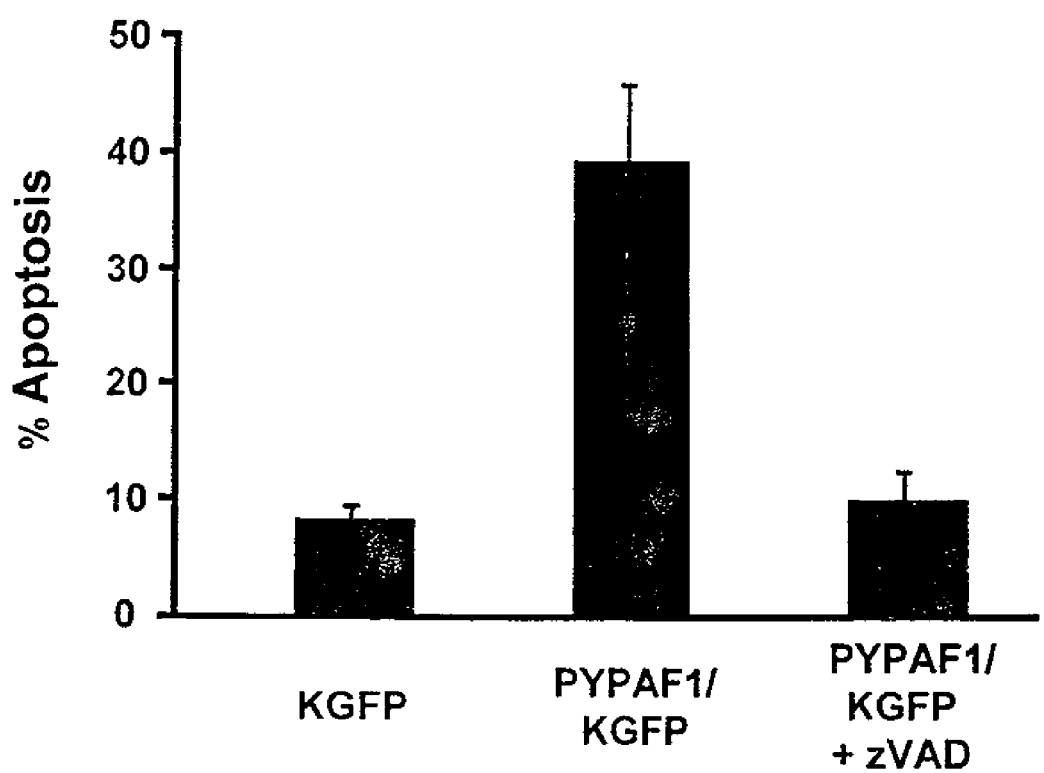
FIG. 11 is a graph depicting the results of an apoptosis assay.

Recombinant adenovirus expressing PYRIN-1 induced apoptosis in 40% of the cells compared with only 8% with control adenovirus (FIG. 11). PYRIN-1-induced apoptosis was blocked by zVAD-fmk, a potent inhibitor of caspase activity. Because both PYRIN-1 and ASC induce apoptosis when expressed in cells (FIG. 11; Masumoto et al., 1999), it is likely that CARD-containing caspases might interact with the C-terminal CARD domain of ASC.

A mammalian two-hybrid screen to determine whether ASC interacts with caspase-1, a CARD-containing caspase involved in apoptosis and cytokine processing. A mammalian two-hybrid analysis was performed using caspase-1-CARD/BD to screen a panel of individual CARD domains. The panel of CARD domains used for the mammalian two-hybrid screen and the plasmids expressing Apaf1 and caspase-1 were described previously (Bertin et al. (2001) supra, Wang et al. (2001) supra; Zou et al. (1997) *Cell* 90:405-413; Geddes et al. (2001) supra). For mammalian two-hybrid assays, 293T cells were transfected with pCMV/AD and pCMV/BD plasmids, pFR-Luc firefly reporter (Stratagene), and, as a transfection efficiency control, pRL-TK Renilla reporter (Promega). Cells were harvested and firefly and Renilla luciferase activities were determined using the Dual-Luciferase reporter assay system (Promega).

Figure 12:
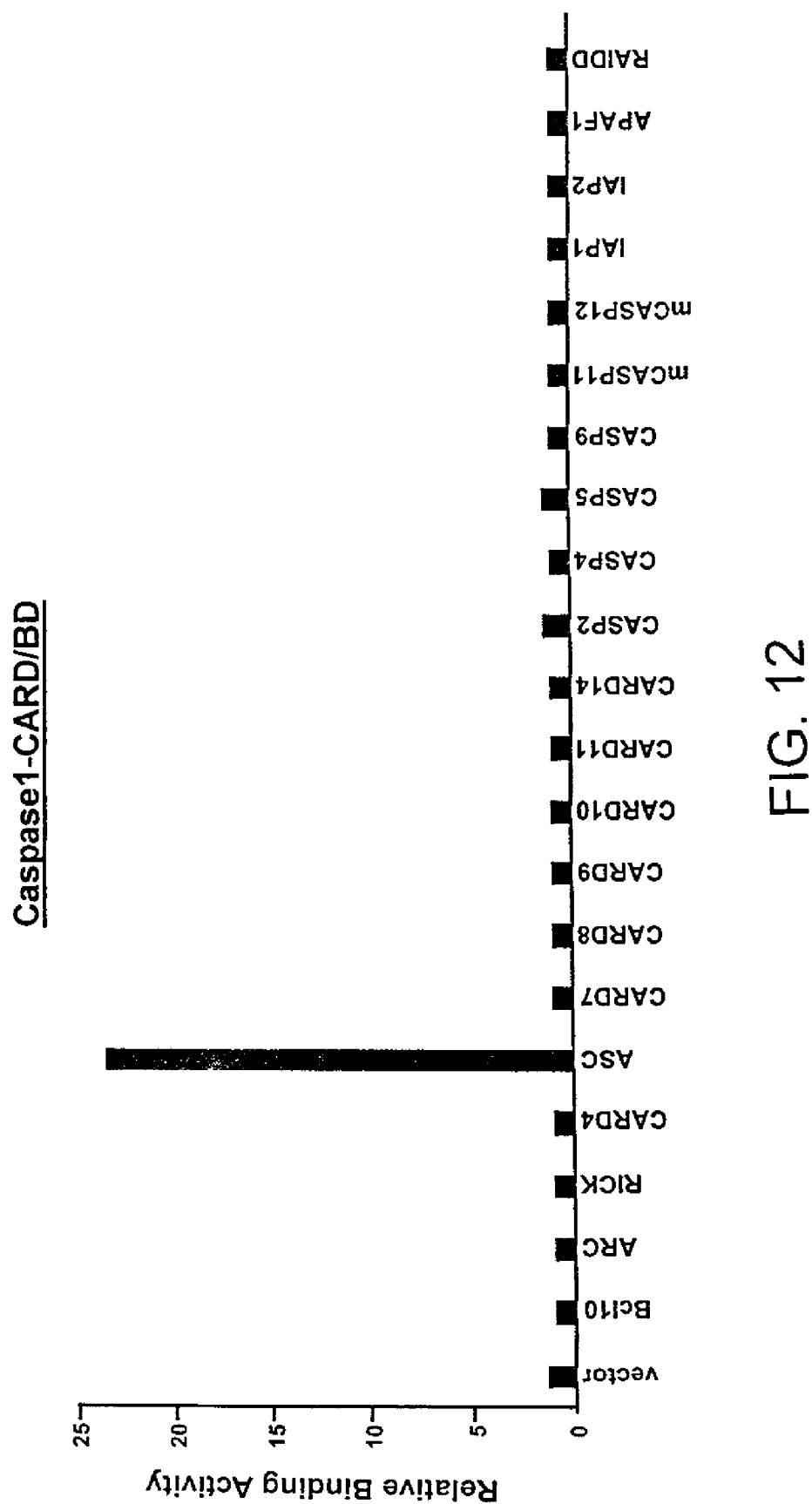
FIG. 12 is a graph depicting the result of a two-hybrid binding assay for identifying CARD domain which bind to the CARD domain of caspase-1.

The relative binding of the CARD domain caspase-1 to the CARD domains of various CARD domain-containing proteins was assessed as described above, and the results of this analysis are presented in FIG. 12. The CARD domain of caspase-1 was found to interact selectively with the CARD domain of ASC resulting in a 24-fold activation of luciferase activity.

Figure 13:
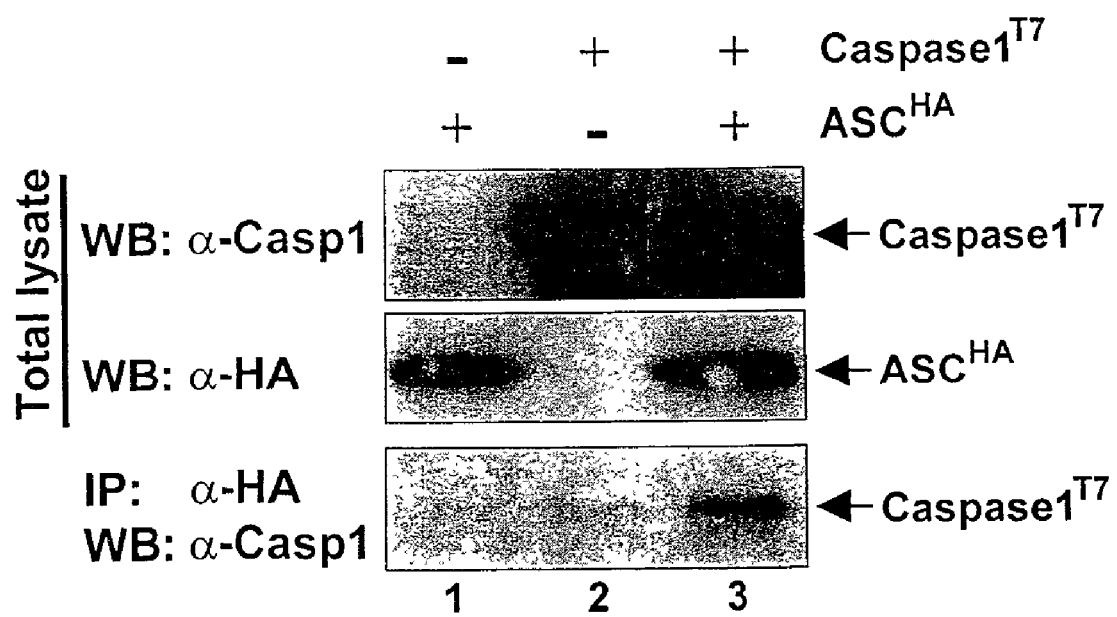
FIG. 13 is a series of blots depicting the results of a co-immunoprecipitation assay in which 293T cells were transfected with expression plasmids encoding HA epitope-tagged ASC and T7 epitope-tagged caspase-1. Cell extracts were immunoprecipitated (IP) with anti-HA immunoblotted (WB) with anti-caspase-1.

In order to further investigate the interaction between ASC and caspase-1, 293T cells were transfected with expression plasmids encoding HA epitope-tagged ASC and T7 epitope-tagged caspase-1. Cell extracts were immunoprecipitated (IP) with anti-HA and then immunoblotted (WB) with anti-caspase-1. Immunoprecipitation of HA-tagged ASC quantitatively co-precipitated T7-tagged caspase-1 (FIG. 13).

Taken together, these findings suggest that the PYRIN-1/ASC signaling complex might engage apoptotic and cytokine processing pathways through an interaction with caspase-1.

PYRIN-1 and ASC Synergistically Activate Caspase-1

Experiments were carried out using an IL-1β secretion assay to determine whether ASC and PYRIN-1 induce activation of caspase-1. Active caspase-1 cleaves pro-IL-1β, resulting in the secretion of bioactive IL-1β from cells. In the IL-1β secretion assays, COS-7L cells (GIBCO) were co-transfected in 12-well (22-mm) plates using LipofectAMINE 200 reagent (Invitrogen) with plasmids encoding mouse pro-IL-1β and indicated expression plasmids (total DNA=1.04 μg). Supernatants were collected 24 hours after transfection and subjected to ELISA for mouse IL-1β according to the manufacturer's protocol (R&D Systems).

Figure 20A:
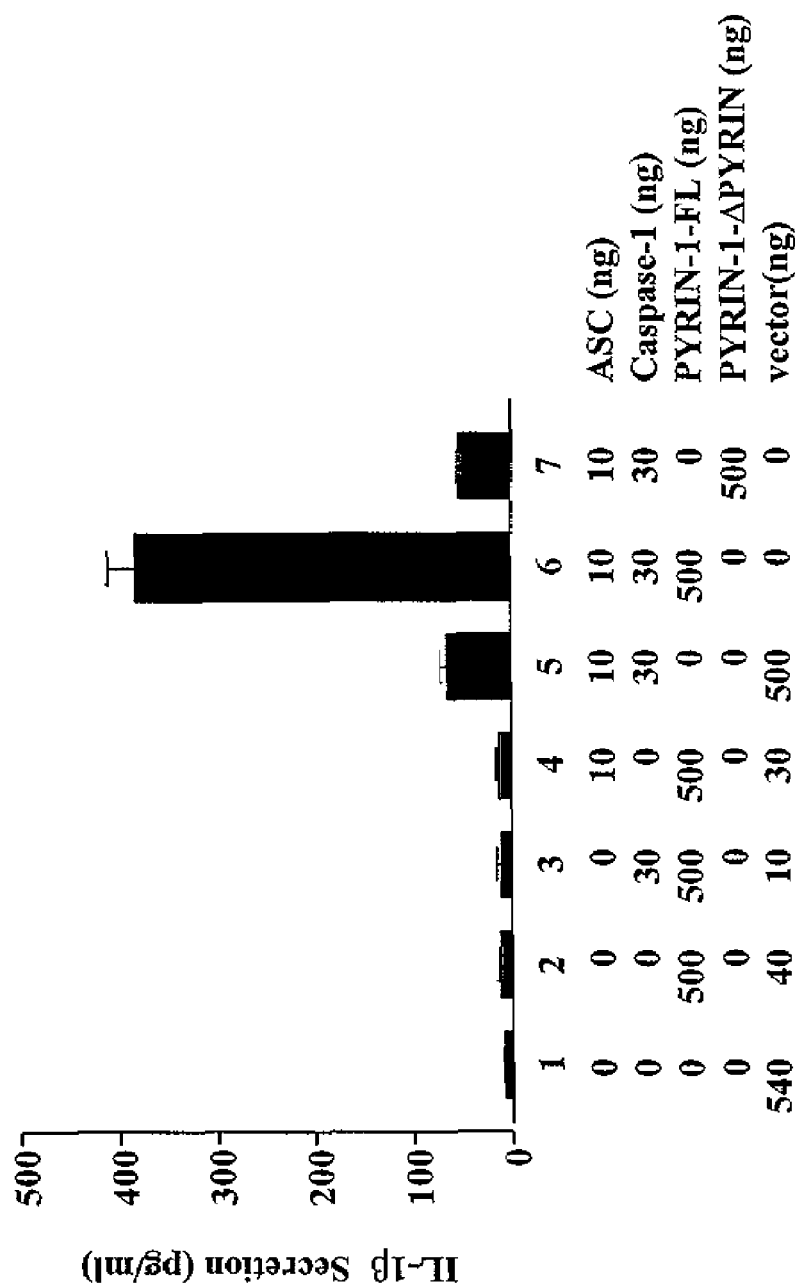
FIGS. 20A and 20B are graphs depicting: (A) the activation of caspase-1, as measured by IL-1β secretion, by PYRIN-1 and ASC; and (B) the requirement for active caspase-1 for the induction of IL-1β secretion by PYRIN-1 and ASC.
Figure 20B:
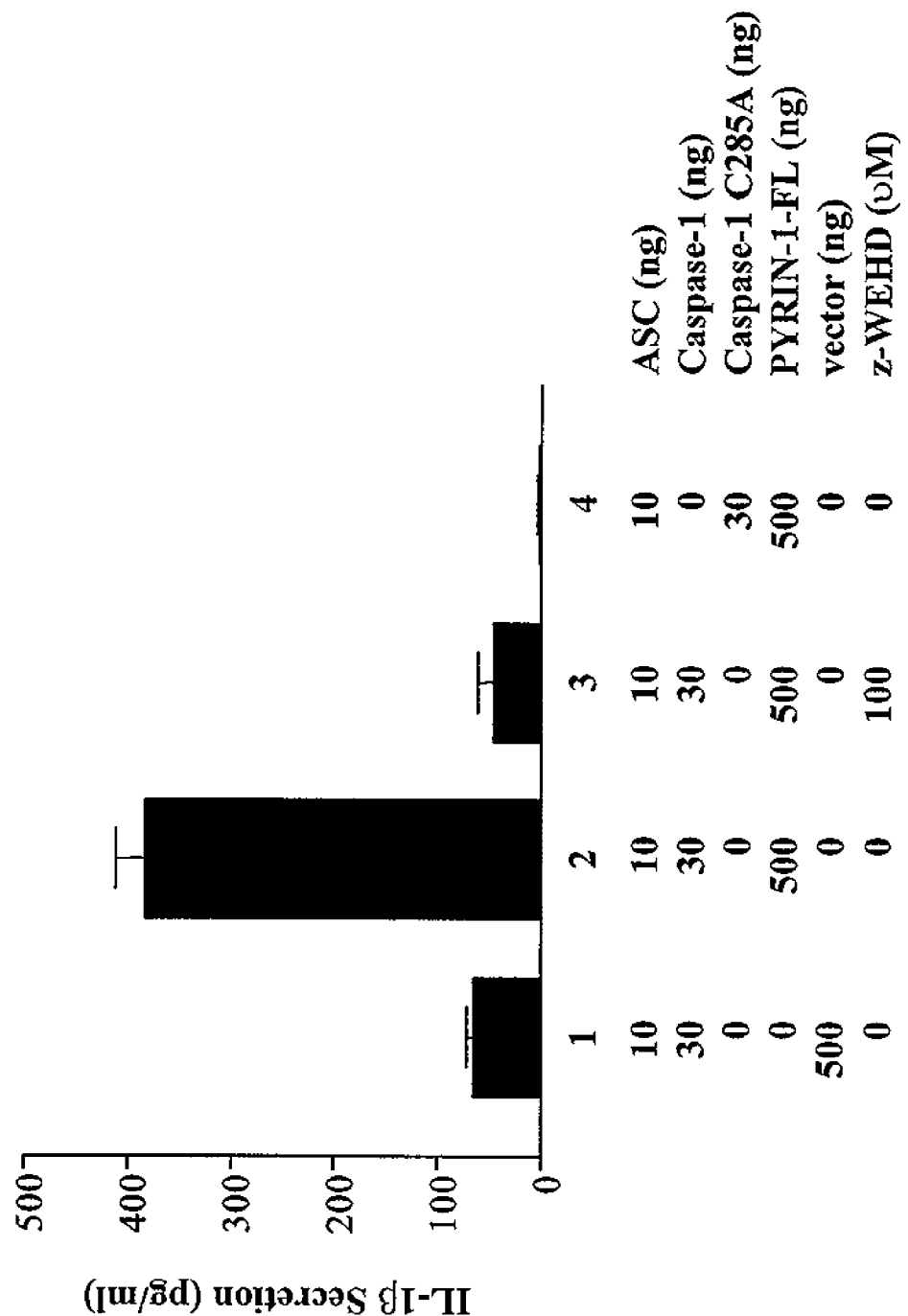

When caspase-1 was expressed at low protein levels that result in minimal levels of IL-1β secretion, co-expression with ASC resulted in a dose-dependent increase in the levels of secreted IL-1β. When caspase-1 and ASC were expressed at low protein levels that resulted in minimal levels of IL-1β secretion, co-expression with PYRIN-1 resulted in the activation of caspase-1 and a corresponding increase in IL-1β production (FIG. 20A, lane 6). The N-terminal PYRIN domain of PYRIN-1 was required for caspase-1 activation, since deletion of this domain (PYRIN-1-ΔPYRIN) eliminated the synergistic production of IL-1β (FIG. 20A, compare lanes 6 and 7). Immunoblot analysis revealed that PYRIN-1-ΔPYRIN was expressed at levels similar to that of PYRIN-1, indicating that loss of function was not due to reduced protein levels. The increase in IL-1β production was dependent on functional caspase-1, because either a caspase-1 active site C285A mutant or the presence of a caspase-1 inhibitor (Z-WEHD) showed little or no activity (FIG. 20B, lane 3 and 4). Taken together, these data demonstrate that PYRIN-1, when co-expressed with ASC, synergistically activates caspase-1-dependent cytokine processing.

PYRIN-1 may function in a manner analogous to other NBS/LRR family members and transmit upstream signals to the activation of ASC and other molecules recruited to the signaling complex. Activation of ASC by PYRIN-1 may occur through an induced-proximity mechanism analogous to the activation of caspase-9 by Apaf1(Salvesen and Dixit, (1999) Proc. Nat'l Acad. Sci USA 96:10964). The restricted expression of PYRIN-1 to immune cells indicates a role for this protein and its binding-partners in inflammatory signaling. Furthermore, the binding of caspase-1 to the CARD domain of ASC and the synergistic activation of caspase-1 by ASC and PYRIN-1 suggests that PYRIN-1 also coordinates signaling pathways that regulate apoptosis and/or the processing of pro-inflammatory cytokines. ASC has been identified recently as a signaling partner of pyrin, a protein involved in a rare inflammatory disorder known as familial Mediterranean fever (Richards et al. (2001) *J. Biol. Chem.*, In Press). The above-described findings on PYRIN-1/ASC signaling suggest that pyrin also engages NF-kB and cytokine processing pathways through its binding to ASC.

As noted above, PYRIN-1 maps to chromosome 1q44, a locus associated with Muckle-Wells syndrome and familial cold urticaria, two genetically determined inflammatory disorders that are similar to Mediterranean fever (Cuisset et al. (1999) *Am. J. Hum. Genet.* 65:1054; Hoffman et al. (2000) *Am J Hum. Genet.* 66:1693; McDermott et al. (2000) *Arthritis Rheum.* 43:2034; Hoffman (2001) *Nat. Genet.* 29:301). Thus, alterations in PYRIN-1 activity or expression, e.g., alterations caused by mutations in the PYRIN-1 gene could be associated with the deregulation of inflammatory signaling and the onset of these hereditary fever syndromes, and factors which increase PYRIN-1 activity can be used to treat these disorders

TABLE 1

Summary of Human NBS-1 and Human PYRIN-1 Sequence Information

| Gene | cDNA | Protein | ORF | FIG |
|---|---|---|---|---|
| Human NBS-1 | SEQ ID NO:1 | SEQ ID NO:2 | SEQ ID NO:3 | FIGS. 1A-E |
| Human PYRIN-1 | SEQ ID NO:4 | SEQ ID NO:5 | SEQ ID NO:6 | FIGS. 4A-4E |

TABLE 2

Summary of Domains of NBS-1 and PYRIN-1

| Domain | Location in NBS-1 | Location in PYRIN-1 |
|---|---|---|
| Pyrin domain | about amino acid residues 3-79 of SEQ ID NO:2 | about amino acid residues 1-87 of SEQ ID NO:5 |
| NBS domain | about amino acid residues 174-605 of SEQ ID NO:2 | about amino acid residues 263-357 of SEQ ID NO:5 |
| Kinase 1a domain (P-loop) | about amino acid residues 180-195 of SEQ ID NO:2 | about amino acid residues 224-233 of SEQ ID NO:5 |
| Kinase 2 domain (Walker B box) | about amino acid residues 249-264 of SEQ ID NO:2 | about amino acid residues 290-306 of SEQ ID NO:5 |
| Kinase 3a domain | about amino acid residues 302-313 of SEQ ID NO:2 | about amino acid residues 344-355 of SEQ ID NO:5 |
| Leucine rich repeats | about amino acids residues 670-697, 698-725, 726-752, 754-781, 782-809, 811-838, 839-866, 868-895, 896-923, 925-952, 953-979, and 981-1008 of SEQ ID NO:2 | about amino acids residues 740-767, 769-796, 797-821, 826-849, 854-878, 883-906, 911-935, 940-967, and 968-991 of SEQ ID NO:5 |
| LRR domain | about amino acid residues 670-1008 of SEQ ID NO:2 | about amino acid residues 740-991 of SEQ ID NO:5 |

Each of NBS-1 and PYRIN-1 are members of a family of molecules (NBS-1 and PYRIN-1 families, respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family, can contain a first protein of human origin and a homologue of that protein of murine origin, as well as a second, distinct protein of human origin and a murine homologue of that protein. Members of a family may also have common functional characteristics.

Preferred NBS-1 or PYRIN-1 polypeptides of the present invention include an amino acid sequence sufficiently identical to one or more of the following domains: a pyrin domain, and NBS domain, and a LRR domain.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeable herein a "NBS-1 or PYRIN-1 activity", "biological activity of NBS-1 or PYRIN-1 " or "functional activity of NBS-1 or PYRIN-1", refers to an activity exerted by a NBS-1 or PYRIN-1 protein, polypeptide or nucleic acid molecule on a NBS-1 or PYRIN-1 responsive cell as determined in vivo, or in vitro, according to standard techniques. NBS-1 or PYRIN-1 may act as a pro-apoptotic protein or an anti-apoptotic protein (i.e., it might act to decrease or increase apoptosis). A NBS-1 or PYRIN-1 activity can be a direct activity, such as an association with or an enzymatic activity on a second protein or an indirect activity, such as a cellular signaling activity mediated by interaction of the NBS-1 or PYRIN-1 protein with a second protein.

In one embodiment, a NBS-1 or PYRIN-1 activity can include at least one or more of the following activities: (i) the ability to interact with proteins in an apoptotic or inflammatory signaling pathway, e.g., ASC and/or caspase-1; (ii) the ability to interact with a NBS-1 or PYRIN-1; (iii) the ability to bind to and/or hydrolyze a nucleotide, e.g., ATP or GTP; (iv) the ability to interact with an intracellular target protein; (v) the ability to interact, directly or indirectly, with one or more proteins having a pyrin domain, a CARD domain, or other domain associated with apoptotic and/or inflammatory signaling; (vi) the ability to modulate, directly or indirectly, the activity of a caspase, e.g., caspase-9, caspase-4, caspase-1, and caspase-5; (vii) the ability to induce the activity of caspase-1; (viii) the ability to modulate of ER-specific apoptosis pathways; (ix) the ability to modulate (increase or decrease), directly or indirectly, the activity of NF-kB; (x) the ability to increase the activity of NF-kB; (xi) the ability to modulate, directly or indirectly, Apaf-1; (xii) the ability to modulate apoptosis and/or inflammation; (xiii) the ability to interact, directly or indirectly, with a Bcl-2 family member; (xiv) the ability to modulate, directly or indirectly, the activity of a stress activated kinase (e.g., JNK/p38); and (xv) the ability to modulate, directly or indirectly, Apaf-1. NBS-1 or PYRIN-1 nucleic acids and polypeptides as well as modulators of activity or expression of NBS-1 or PYRIN-1 might be used to modulate an Apaf-1 signaling pathway.

In another embodiment, a PYRIN-1 activity can include: (i) the ability to interact with ASC, e.g., via their respective pyrin domains; (ii) the ability to increase ASC-dependent NF-kB activity; (iii) the ability to increase apoptosis; (iv) the ability to increase caspase-mediated apoptosis or inflammation; (v) the ability to activate ASC; (vi) the ability to increase ASC-dependent caspase-1 activity; and (vii) the ability to transmit a pro-apoptotic signal to ASC.

ASC may interact with other pyrin domain-containing proteins in addition to PYRIN-1, e.g., PYRIN-2, 3, 5, 6, 7, 8, 10, and 11 (described in U.S. Ser. No. 10/066,521, filed Jan. 31, 2002, hereby incorporated by reference).

NBS-1 and PYRIN-1 nucleic acids and polypeptides, as well as modulators of NBS-1 or PYRIN-1 activity or expression, are expected to be useful in the modulation of stress-related, apoptotic and inflammatory responses, e.g., for the treatment of apoptotic and inflammatory disorders. In addition, NBS-1 and PYRIN-1 nucleic acids and polypeptides are expected to be useful in the diagnosis of apoptotic and inflammatory disorders as well as in screening assays which can be used to identify compounds which can be used to modulate stress-related, apoptotic and inflammatory responses.

Many cytoplasmic plant proteins involved in response to plant pathogens, generally referred to as "R" proteins have both an NBS domain and an LRR domain. R proteins are involved in both a rapid defense response (hypersensitive response) and more long-term nonspecific resistance (systemic acquired resistance). The hypersensitive response involves cell and tissue death that is localized to the site of infection. The LRR domains of R proteins are believed to recognize and bind to pathogen proteins, triggering defensive responses. Many R proteins have an amino terminal effector domain (e.g., a TIR domain or a leucine zipper domain) that is thought to play a role in downstream signaling of events triggered by infection and, possibly, other stresses.

The R proteins have some structural similarity to APAF-1, a protein which mediates between Bcl-2, a negative regulator of apoptosis, and caspases, which are the proteases directly responsible for the degradation of cellular proteins that leads to the morphological changes seen in cells undergoing apoptosis. APAF-1 has a CARD domain, functionally analogous to the effector domain of R proteins, an NBS domain, and a WD-40 domain, functionally analogous to the LRR domain of R proteins.

CARD-4, CARD-7, and CARD-12 each have an NBS domain and an LRR domain as well as a CARD domain (detailed information concerning CARD-4, CARD-7, and CARD-12 can be found in U.S. application Ser. No 09/245, 281, filed Feb. 5, 1999, now U.S. Pat. No. 6,369,196, U.S. application Ser. No. 09/207,359, filed Dec. 8, 1998, now U.S. Pat. No. 6,469,140, U.S. application Ser. No. 09/099, 041, filed Jun. 17, 1998, now U.S. Pat. No. 6,340,576, U.S. application Ser. No. 09/019,942, filed Feb. 6, 1998, now U.S. Pat. No. 6,033,855, U.S. application Ser. No. 09/428, 252, filed Oct. 27, 1999, and U.S. application Ser. No. 60/161,822, filed Oct. 27, 1999, all of which are incorporated herein by reference). The CARD domain, which is present in a number of apoptotic signaling molecules, is an effector domain that thought to be involved in homophilic protein-protein interactions, e.g., with downstream CARD-containing signaling molecules. For example, the CARD domain of CARD-4 interacts with the CARD domain of RICK (RIP2, CARDIAK), a serine-threonine kinase that activates NF-κB signaling pathways.

Other proteins structurally related to NBS-1 and PYRIN-1 include NBS-2, NBS-3, NBS-4, and NBS-5, each of which contains an NBS domain. NBS-2, NBS-3, and NBS-5 contain LRR domains and NBS-2 and NBS-3 contain pyrin domains. Detailed information concerning NBS-2, NBS-3, NBS-4, and NBS-5 can be found in U.S. application Ser. No. 60/201,464, filed May 3, 2000, which is incorporated herein by reference.

In general, an NBS domain includes a kinase 1 a domain (P-loop), a kinase 2 domain (Walker B box) and a kinase 3a domain. An LRR domain usually is composed of several leucine rich repeats.

Without being bound by a particular theory, it is possible that the LRR domain of NBS-1 and PYRIN-1 interacts with an upstream signaling molecule that is associated with stress, infection, or inflammation. This interaction triggers a conformational change in NBS-1 or PYRIN-1 that exposes an effector domain, e.g., the pyrin domain of NBS-1. The exposed effector domain then mediates interaction with a downstream signaling molecule or molecules to transmit a stress-related, apoptotic or inflammatory signal. In this model, the conformational change is dependent upon binding and/or hydrolysis of a nucleotide triphosphate (ATP or GTP) bound to the NBS domain.

NBS-1 and PYRIN-1 molecules are useful as modulating agents in regulating a variety of cellular processes including inflammation and apoptosis. The molecules are also useful in the identification of agent for the modulation of inflammation and apoptosis.

The invention encompasses methods of diagnosing and treating patients who are suffering from a disorder associated with an abnormal level or rate (undesirably high or undesirably low) of apoptotic cell death, abnormal activity of stress-related pathways of the endoplasmic reticulum (ER), abnormal activity of the Fas/APO-1 receptor complex, abnormal activity of the TNF receptor complex, abnormal activity of NF-kB, or abnormal activity of a caspase by administering a compound that modulates the expression of NBS-1 or PYRIN-1 (at the DNA, mRNA or protein level, e.g., by altering mRNA splicing) or by altering the activity of NBS-1 or PYRIN-1. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. NBS-1 or PYRIN-1 and compounds that modulate the expression or activity of NBS-1 or PYRIN-1 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, an autoimmune disorder can be caused by an undesirably low level of apoptosis. Accordingly, NBS-1 or PYRIN-1 and modulators of NBS-1 or PYRIN-1 activity or expression can be used to treat autoimmune disorders (e.g., systemic lupus erythematosis, immune-mediated glomerulonephritis, and arthritis).

Many diseases are associated with an undesirably high rate of apoptosis. NBS-1 or PYRIN-1 and modulators of NBS-1 or PYRIN-1 expression or activity can be used to treat or diagnose such disorders. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, Huntington's disease, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myclodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. Additional diseases associated with an undesirably high rate of apoptosis include: ischemic and hypoxic brain injury, traumatic and excitotoxic brain damage, neuronal transplantation, acute bacterial meningitis, kidney ischemia/reperfusion injury, and liver disease. NBS-1 or PYRIN-1 and modulators of NBS-1 or PYRIN-1 may therefore be useful in treating and diagnosing these conditions.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

NBS-1 or PYRIN-1 polypeptides, nucleic acids and modulators of NBS-1 or PYRIN-1 expression or activity can be used to treat inflammatory disorders and immune system disorders, e.g., by interfering with or inhibiting NF-κB activity that is stimulated by PYRIN-1. Disorders include inflammatory disorders include such as inflammatory bowel disorders, Crohn's disease, ulcerative colitis, reactive arthritis, rheumatoid arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, respiratory inflammatory diseases and disorders, such as asthma and chronic obstructive pulmonary disease, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy. Such disorders can be treated by interfering with PYRIN-1-mediated pro-inflammatory activity. Other inflammatory disorders that might be treated by decreasing PYRIN-1-mediated NF-κB activity include, e.g., bacterial infection, psoriasis, septicemia, cerebral malaria, inflammatory bowel disease, arthritis (e.g., rheumatoid arthritis, osteoarthritis) colitis (e.g., idiopathic ulcerative colitis and pseudomembranous colitis)

Ischemia is often accompanied by inflammation that causes cell death. Because NBS-1 and PYRIN-1 are expected to play a role in stress-related response, inflammation and apoptosis, NBS-1 or PYRIN-1 polypeptides, nucleic acids, and modulators of NBS-1 or PYRIN-1 expression or activity can be used to treat cells death accompanying inflammatory responses triggered by ischemia.

Invasive infection with Gram-negative bacteria and Gram-positive bacteria often results in septic shock. NBS-1 and PYRIN-1 may recognize and bind components of Gram-negative bacteria and Gram-positive bacteria or other infectious agents (e.g., intracellular parasites), triggering an inflammatory response. Thus, NBS-1 and PYRIN-1 may play a role in innate immune system responses that is similar to that of Toll-like receptor 2 (TLR2), a receptor which has some structural similarity to plant R proteins and IL-1 R. TLR2 is a signaling receptor that, in association with CD14, is activated by LPS in a response that requires LPS-binding protein. The interaction of TLR2 with LPS leads to TLR2 oligomerization and recruitment of IRAK (Yang et al. (1998) *Nature* 395:284-88; Yang et al (1999) *J. Immunol.* 163:639-43; and Yoshimura et al. (1999) *J. Immunol.* 163: 105). Thus, TLR2 is thought to be a direct mediator of signaling by LPS. TLR2 is also thought to mediate cell activation induced by peptidoglycan and lipoteichoic acid, the main stimulatory components of Gram-positive bacteria (Schwandner et al. (1999) *J. Biol. Chem.* 274:17406-09). Modulators of PYRIN-1 activity, e.g., activators of PYRIN-1 activity or expression can be used to treat Muckle-Wells syndrome and familial cold urticaria. Modulators of PYRIN-1 activity may be particularly useful for treating arthritis, e.g., rheumatoid arthritis.

In addition to the aforementioned disorders, NBS-1 or PYRIN-1 polypeptides, nucleic acids, and modulators of NBS-1 or PYRIN-1 expression or activity can be used to treat septic shock and other disorders associated with an innate immune response. For example, NBS-1 or PYRIN-1 may bind to a component of an intracellular infectious agent or a component of an infectious agent that is brought into a cell expressing NBS-1 or PYRIN-1, e.g., a component that enters a cell through a receptor or is expressed by a viral gene. In addition to the aforementioned disorders, NBS-1 or PYRIN-1 polypeptides, nucleic acids, and modulators of NBS-1 or PYRIN-1 expression or activity can be used to treat disorders of cell signaling and disorders of tissues in which NBS-1 or PYRIN-1 is expressed.

Various aspects of the invention are described in further detail in the following subsections.

I. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A NBS-1 or PYRIN-1 protein interacts with other cellular proteins and can thus be used for (i) regulation of cellular proliferation; (ii) regulation of cellular differentiation; and (iii) regulation of cell survival. The isolated nucleic acid molecules of the invention can be used to express NBS-1 or PYRIN-1 protein (e.g., via a recombinant expression vector in a host cell in gene therapy applications), to detect NBS-1 or PYRIN-1 mRNA (e.g., in a biological sample) or a genetic lesion in a NBS-1 or PYRIN-1 gene, and to modulate NBS-1 or PYRIN-1 activity. In addition, the NBS-1 or PYRIN-1 proteins can be used to screen drugs or compounds which modulate the NBS-1 or PYRIN-1 activity or expression as well as to treat disorders characterized by insufficient or excessive production of NBS-1 or PYRIN-1 protein or production of NBS-1 or PYRIN-1 protein forms which have decreased or aberrant activity compared to NBS-1 or PYRIN-1 wild type protein. In addition, the anti-NBS-1 or PYRIN-1 antibodies of the invention can be used to detect and isolate NBS-1 or PYRIN-1 proteins and modulate NBS-1 or PYRIN-1 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to NBS-1 or PYRIN-1 proteins or biologically active portions thereof or have a stimulatory or inhibitory effect on, for example, NBS-1 or PYRIN-1 expression or NBS-1 or PYRIN-1 activity. An example of a biologically active portion of human NBS-1 is a domain described herein. An example of a biologically active portion of human PYRIN-1 is a domain described herein.

Among the screening assays provided by the invention are screening to identify molecules that prevent the interaction of NBS-1 or PYRIN-1 with another protein and screening to identify a competitive inhibitor of the binding of a nucleotide to the nucleotide binding site of NBS-1 or PYRIN-1. Such assays can employ full-length NBS-1 or PYRIN-1 or a portion of NBS-1 or PYRIN-1, e.g., a domain define herein.

Screening assays can be used to identify molecules which modulate a NBS-1 or PYRIN-1 mediated increase in transcription of genes having an AP-1 or NF-κB binding site. For example, expression of a reporter gene under the control of NF-κB (or AP-1) is measured in the presence and absence of a candidate molecule and in the presence and absence of NBS-1 or PYRIN-1 to identify those molecules which alter expression of the reporter in a NBS-1 or PYRIN-1 dependent manner. In addition, screening assays can be used to identify molecules that modulate a NBS-1 or PYRIN-1 mediated increase in CHOP phosphorylation. For example, the expression of a reporter gene under the control of CHOP is measured in the presence and absence of a candidate small molecule and in the presence and absence of NBS-1 or PYRIN-1 to identify those molecules that alter expression of the reporter in a NBS-1 or PYRIN-1 dependent manner. A screening assay can be carried out to identify molecules which modulate the NBS-1 or PYRIN-1 mediated increase in CHOP phosphorylation. For example, CHOP phosphorylation is measured in the presence and absence of a candidate molecule and in the presence and absence of NBS-1 or PYRIN-1. Phosphorylation of CHOP can be measured using an antibody which binds to phosphorylated CHOP, but not to non-phosphorylated CHOP.

Molecules that bind to and/or alter the activity of an NBS domain of NBS-1 or PYRIN-1 may be useful for modulating the activity of NBS-1 or PYRIN-1. For example, molecules can be tested for their ability to modulate, e.g., antagonize, the hydrolysis of an NTP, e.g., ATP, by the NBS domain (or a fragment of an NBS domain such as an NBS motif described herein) of NBS-1 or PYRIN-1. Methods of detecting the hydrolysis of a NTP by a protein containing a nucleotide-binding site are described in, for example, Li et al. (1996) *J. Biol. Chem.* 271:28463-28468 and Gadsby et al. (1999) *Physiol. Rev.* 79: S77-S107.

A purified protein containing an NBS domain of NBS-1 or PYRIN-1 can be evaluated for its ability to mediate NTPase activity in vitro. The assay can be performed in the presence of a test compound to determine the ability of the test compound to modulate the NTPase activity of the purified protein. In addition, or alternatively, the purified protein used in an NTPase activity assay can be a variant or a fragment of NBS-1 or PYRIN-1, and the assay can be performed to determine the NTPase activity of the fragment or variant.

In one example, an NBS domain can be assayed for its ability to hydrolyze ATP. ATPase activity can measured as the production of $[\alpha^{32}\text{-P}]$ADP from $[\alpha^{32}\text{-P}]$ATP, using polyethyleneimine-cellulose chromatography for separation of the nucleotides. The assay can be carried out in a 15 µl reaction mixture containing 50 mM Tris, 50 mM NaCl, pH 7.5, 2 mM MgCl$_2$, 10% glycerol, 0.5 mM CHAPS, and 8 µCi of [α$^{32}$-P]ATP. Reaction mixtures are incubated at 30° C. and are stopped by the addition of 5 µl of 10% SDS. One µl samples are spotted on a polyethyleneimine-cellulose plate and developed in 1 M formic acid, 0.5 M LiCl. The location and quantitation of the radiolabeled ATP and ADP can determined with a Molecular Dynamics PhosphorImager. Data can be analyzed using the ImageQuant software package (Molecular Dynamics). See, e.g., Li et al. (1996) *J. Biol. Chem.* 271:28463-28468 for additional details on methods detecting ATPase activity by nucleotide binding site-containing proteins and variants thereof. Thin layer chromatography techniques similar to those described above can also be used for the measurement of NTPase activity such as GTPase activity (see, e.g., Gout et al. (1993) *Cell* 75:25-36).

Screening assays can be used to identify molecules that bind to and/or modulate the activity of a pyrin domain or a LRR domain of a NBS-1 or PYRIN-1 protein, fragment, or variant thereof.

In one embodiment, the invention provides assays for screening candidate or test compounds which bind to or modulate the activity of a NBS-1 or PYRIN-1 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145). Examples of methods for the synthesis of molecular libraries can be found in the art, for example in: DeWitt et al. (1993) *Proc. Natl. Acad. Sci USA* 90:6909; Erb et al. (1994) *Proc Natl Acad. Sci USA* 91:11422; Zuckermann et al. (1994). *J. Med. Chem.* 37:2678; Cho et al. (1993) *Science* 261:1303; Carrell et al. (1994) *Angew Chem Int Ed Engl.* 33:2059; Carell et al. (1994) *Angew. Chem Int Ed Engl.* 33:2061; and Gallop et al. (1994) *J. Med. Chem.* 37:1233.

Libraries of compounds may be :resented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad Sci USA* 89:1865-1869) or on phage (Scott and Smith (1990) *Science* 249: 386-390; Devlin (1990) *Science* 249:404-406; Cwirla et al. (1990) *Proc. Natl. Acad Sci. USA* 87:6378-6382; and Felici (1991) *J Mol Biol.* 222:301-310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of NBS-1 or PYRIN-1 or a biologically active portion thereof can be accomplished, for example, by determining the ability of the NBS-1 or PYRIN-1 protein to bind to or interact with a NBS-1 or PYRIN-1 target molecule. As used herein, a "target molecule" is a molecule with which a NBS-1 or PYRIN-1 protein binds or interacts in nature, for example, a molecule associated with the internal surface of a cell membrane or a cytoplasmic molecule. A NBS-1 or PYRIN-1 target molecule can be a non-NBS-1 or PYRIN-1 molecule or a NBS-1 or PYRIN-1 protein or polypeptide of the present invention. In one embodiment, a NBS-1 or PYRIN-1 target molecule is a component of an apoptotic signal transduction pathway. The target, for example, can be a second intracellular protein which has catalytic activity or a protein which facilitates the association of downstream signaling molecules with NBS-1 or PYRIN-1. In particular the target can be another protein having a pyrin domain (or a pyrin domain containing fragment thereof).

Determining the ability of the test compound to modulate the activity of NBS-1 or PYRIN-1 or a biologically active portion thereof can be accomplished, for example, by determining the ability of the NBS-1 or PYRIN-1 protein to bind to or interact with any of the specific proteins listed in the previous paragraph as NBS-1 or PYRIN-1 target molecules. In another embodiment, NBS-1 or PYRIN-1 target molecules include all proteins that bind to a NBS-1 or PYRIN-1 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the NBS-1 or PYRIN-1 protein to bind to or interact with a NBS-1 or PYRIN-1 target molecule can be accomplished by one of the methods described above for determining direct binding. In an embodiment, determining the ability of the NBS-1 or PYRIN-1 protein to bind to or interact with a NBS-1 or PYRIN-1 target molecule can be accomplished by determining the activity of the target molecule. For example, the activity of the target molecule can be determined by detecting induction of a cellular second messenger of the target (e.g., intracellular Ca$^{2+}$, diacylglycerol, IP3, etc.), detecting catalytic/enzymatic activity of the target on an appropriate substrate, detecting the induction of a reporter gene (e.g., a NBS-1 or PYRIN-1-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by NBS-1 or PYRIN-1 expression can be identified by expressing NBS-1 or PYRIN-1 in a cell line and conducting a transcriptional profiling experiment wherein the mRNA expression patterns of the cell line transformed with an empty expression vector and the cell line transformed with a NBS-1 or PYRIN-1 expression vector are compared. The promoters of genes induced by NBS-1 or PYRIN-1 expression can be operatively linked to reporter genes suitable for screening such as luciferase, secreted alkaline phosphatase, or beta-galactosidase and the resulting constructs could be introduced into appropriate expression vectors. A recombinant cell line containing NBS-1 or PYRIN-1 and transfected with an expression vector containing a NBS-1 or PYRIN-1 responsive promoter operatively linked to a reporter gene can be used to identify test compounds that modulate NBS-1 or PYRIN-1 activity by assaying the expression of the reporter gene in response to contacting the recombinant cell line with test compounds. NBS-1 or PYRIN-1 agonists can be identified as increasing the expression of the reporter gene and NBS-1 or PYRIN-1 antagonists can be identified as decreasing the expression of the reporter gene.

In another embodiment of the invention, the ability of a test compound to modulate the activity of NBS-1 or PYRIN-1, or biologically active portions thereof can be determined by assaying the ability of the test compound to modulate NBS-1 or PYRIN-1-dependent pathways or processes where the NBS-1 or PYRIN-1 target proteins that mediate the NBS-1 or PYRIN-1 effect are known or unknown. Potential NBS-1 or PYRIN-1-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. NBS-1 or PYRIN-1-dependent pathways or processes could be assayed by standard cell-based or cell free assays appropriate for the specific pathway or process under study. In another embodiment, cells cotransfected with NBS-1 or PYRIN-1 and a NF-κB luciferase reporter gene could be contacted with a test compound and test compounds that block NBS-1 or PYRIN-1 activity could be identified by their reduction of NBS-1 or PYRIN-1-dependent NF-κB pathway luciferase reporter gene expression. Test compounds that agonize NBS-1 or PYRIN-1 would be expected to increase reporter gene expression. In another embodiment, NBS-1 or PYRIN-1 could be expressed in a cell line and the recombinant NBS-1 or PYRIN-1-expressing cell line could be contacted with a test compound. Test compounds that inhibit NBS-1 or PYRIN-1 activity could be identified by their reduction of NBS-1 or PYRIN-1-depended NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a NBS-1 or PYRIN-1 protein or biologically active portion thereof with a test compound and determining the ability of the test compound to bind to the NBS-1 or PYRIN-1 protein or biologically active portion thereof. Binding of the test compound to the NBS-1 or PYRIN-1 protein can be determined either directly or indirectly as described above. In one embodiment, a competitive binding assay includes contacting the NBS-1 or PYRIN-1 protein or biologically active portion thereof with a compound known to bind NBS-1 or PYRIN-1 to form an assay mixture, contacting the assay mixture with a test compound, and determining the ability of the test compound to interact with a NBS-1 or PYRIN-1 protein, wherein determining the ability of the test compound to interact with a NBS-1 or PYRIN-1 protein comprises determining the ability of the test compound to preferentially bind to NBS-1 or PYRIN-1 or biologically active portion thereof as compared to the known binding compound.

In another embodiment, an assay is a cell-free assay comprising contacting NBS-1 or PYRIN-1 protein or biologically active portion thereof with a test compound and determining the ability of the test compound to modulate (e.g., stimulate or inhibit) the activity of the NBS-1 or PYRIN-1 protein or biologically active portion thereof. Determining the ability of the test compound to modulate the activity of NBS-1 or PYRIN-1 can be accomplished, for example, by determining the ability of the NBS-1 or PYRIN-1 protein to bind to or interact with a NBS-1 or PYRIN-1 target molecule by one of the methods described above for determining direct binding. In an alternative embodiment, determining the ability of the test compound to modulate the activity of NBS-1 or PYRIN-1 can be accomplished by determining the ability of the NBS-1 or PYRIN-1 protein to further modulate a NBS-1 or PYRIN-1 target molecule. For example, the catalytic/enzymatic activity of the target molecule on an appropriate substrate can be determined as previously described.

In yet another embodiment, the cell-free assay comprises contacting the NBS-1 or PYRIN-1 protein or biologically active portion thereof with a known compound which binds NBS-1 or PYRIN-1 to form an assay mixture, contacting the assay mixture with a test compound, and determining the ability of the test compound to interact with a NBS-1 or PYRIN-1 protein, wherein determining the ability of the test compound to interact with a NBS-1 or PYRIN-1 protein comprises determining the ability of the NBS-1 or PYRIN-1 protein to preferentially bind to or modulate the activity of a NBS-1 or PYRIN-1 target molecule. The cell-free assays of the present invention are amenable to use of either the soluble form or a membrane-associated form of NBS-1 or PYRIN-1. A membrane-associated form of NBS-1 or PYRIN-1 refers to NBS-1 or PYRIN-1 that interacts with a membrane-bound target molecule. In the case of cell-free assays comprising the membrane-associated form of NBS-1 or PYRIN-1, it may be desirable to utilize a solubilizing agent such that the membrane-associated form of NBS-1 or PYRIN-1 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either NBS-1 or PYRIN-1 or its target molecule to facilitate separation of complexed from uncomplexed forms of one or both of the proteins, as well as to accommodate automation of the assay. Binding of a test compound to NBS-1 or PYRIN-1, or interaction of NBS-1 or PYRIN-1 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/NBS-1 or PYRIN-1 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or NBS-1 or PYRIN-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-1 or PYRIN-1 binding or activity determined using standard techniques. In an alternative embodiment, MYC or HA epitope tag NBS-1 or PYRIN-1 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or NBS-1 or PYRIN-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-1 or PYRIN-1 binding or activity determine(d using standard techniques.

Other techniques for immobilizing proteins on matrices can also be used in the screening assays of the invention. For example, NBS-1 or PYRIN-1 or its target molecule can be immobilized utilizing conjugation of biotin and streptavidin. Biotinylated NBS-1 or PYRIN-1 target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with NBS-1 or PYRIN-1 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the NBS-1 or PYRIN-1 or target molecule, as well as enzyme-linked assays which rely on detecting an enzymatic activity associated with the NBS-1 or PYRIN-1 or a target molecule.

In another embodiment, modulators of NBS-1 or PYRIN-1 expression are identified in a method in which a cell is contacted with a candidate compound and the expression of the NBS-1 or PYRIN-1 promoter, mRNA or protein in the cell is determined. The level of expression of NBS-1 or PYRIN-1 mRNA or protein in the presence of the candidate compound is compared to the level of expression of NBS-1 or PYRIN-1 mRNA or protein in the absence of the candidate compound. The candidate compound can then be identified as a modulator of NBS-1 or PYRIN-1 expression based on this comparison. For example, when expression of NBS-1 or PYRIN-1 mRNA or protein is greater (statistically significantly greater) in the presence of the candidate compound than in its absence, the candidate compound is identified as a stimulator of NBS-1 or PYRIN-1 mRNA or protein expression. Alternatively, when expression of NBS-1 or PYRIN-1 mRNA or protein is less (statistically significantly less) in the presence of the candidate compound than in its absence, the candidate compound is identified as an inhibitor of NBS-1 or PYRIN-1 mRNA or protein expression. The level of NBS-1 or PYRIN-1 mRNA or protein expression in the cells can be determined by methods described herein for detecting NBS-1 or PYRIN-1 mRNA or protein. The activity of the NBS-1 or PYRIN-1 promoter can be assayed by linking the NBS-1 or PYRIN-1 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the NBS-1 or PYRIN-1 proteins can be used as "bait proteins" in a two-hybrid assay (for a discussion of a mammalian two-hybrid assay, see e.g., Hosfield and Chang (1999) *Strategies Newsletter* 2(2): 62-65) or three hybrid assay (see, e.g., U.S. Pat. No. 5,283,317; Zervos et al. (1993) *Cell* 72:223-232; Madura et al. (1993) *J Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with NBS-1 or PYRIN-1 ("NBS-1 or PYRIN-1-binding proteins" or "NBS-1 or PYRIN-1-bp") and modulate NBS-1 or PYRIN-1 activity. Such NBS-1 or PYRIN-1-binding proteins are also likely to be involved in the propagation of signals by the NBS-1 or PYRIN-1 proteins as, for example, upstream or downstream elements of the NBS-1 or PYRIN-1 pathway.

The two-hybrid system is based on the modular nature of most transcription factors, which consist of separable DNA-binding and activation domains. Briefly, the assay utilizes two different DNA constructs. In one construct, the gene that codes for NBS-1 or PYRIN-1 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NBS-1 or PYRIN-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with NBS-1 or PYRIN-1.

In an embodiment of the invention, the ability of a test compound to modulate the activity of NBS-1 or PYRIN-1, or a biologically active portion thereof can be determined by assaying the ability of the test compound to block the binding of NBS-1 or PYRIN-1 to its target proteins in a yeast or mammalian two-hybrid system assay. This assay could be automated for high throughput drug screening purposes. In another embodiment of the invention, NBS-1 or PYRIN-1 and a target protein could be configured in the reverse two-hybrid system (Vidal et al. (1996) *Proc Natl. Acad Sci. USA* 93:10321-6 and Vidal et al. (1996) *Proc Natl. Acad. Sci. USA* 93:10315-20) designed specifically for efficient drug screening. In the reverse two-hybrid system, inhibition of a NBS-1 or PYRIN-1 physical interaction with a target protein would result in induction of a reporter gene in contrast to the normal two-hybrid system where inhibition of NBS-1 or PYRIN-1 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to NBS-1 or PYRIN4-1. NBS-1 or PYRIN-1 interactors could be configured into two-hybrid system baits and used in two-hybrid screens to identify additional members of the NBS-1 or PYRIN-1 pathway. The interactors of NBS-1 or PYRIN-1 interactors identified in this way could be useful targets for therapeutic intervention in NBS-1 or PYRIN-1 related diseases and pathologies and an assay of their enzymatic or binding activity could be useful for the identification of test compounds that modulate NBS-1 or PYRIN-1 activity.

This invention further pertains to novel agents identified by the above-described screening assays and uses thereof for treatments as described herein.

B. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining NBS-1 or PYRIN-1 protein and/or nucleic acid expression as well as NBS-1 or PYRIN-1 activity, in the context of a biological sample (e.g., blood, serum, cells, tissue) to thereby determine whether an individual is afflicted with a disease or disorder, or is at risk of developing a disorder, associated with aberrant NBS-1 or PYRIN-1 expression or activity. The invention also provides for prognostic (or predictive) assays for determining whether an individual is at risk of developing a disorder associated with NBS-1 or PYRIN-1 protein, nucleic acid expression or activity. For example, mutations in a NBS-1 or PYRIN-1 gene can be assayed in a biological sample. Such assays can be used for prognostic or predictive purpose to thereby prophylactically treat an individual prior to the onset of a disorder characterized by or associated with NBS-1 or PYRIN-1 protein, nucleic acid expression or activity.

Another aspect of the invention provides methods for determining NBS-1 or PYRIN-1 protein, nucleic acid expression or NBS-1 or PYRIN-1 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of NBS-1 or PYRIN-1 in clinical trials.

These and other agents are described in further detail in the following sections.

1. Diagnostic Assays

An exemplary method for detecting the presence or absence of NBS-1 or PYRIN-1 in a biological sample involves obtaining a biological sample from a test subject and contacting the biological sample with a compound or an agent capable of detecting NBS-1 or PYRIN-1 protein or nucleic acid (e.g., mRNA, genomic DNA) that encodes NBS-1 or PYRIN-1 protein such that the presence of NBS-1 or PYRIN-1 is detected in the biological sample. An agent for detecting NBS-1 or PYRIN-1 mRNA or genomic DNA is a labeled nucleic acid probe capable of hybridizing to NBS-1 or PYRIN-1 mRNA or genomic DNA. The nucleic acid probe can be, for example, a full-length NBS-1 or PYRIN-1 nucleic acid, such as the nucleic acid of SEQ ID NO:1, SEQ ID NO:3, SEQ ID NO:4, SEQ ID NO:6, or a portion thereof, such as an oligonucleotide of at least 15, 30, 50, 100, 250, 500, 750, 1000, 1250, or 1500 nucleotides in length and sufficient to specifically hybridize under stringent conditions to mRNA or genomic DNA. Other suitable probes for use in the diagnostic assays of the invention are described herein.

An agent for detecting NBS-1 or PYRIN-1 protein can be an antibody capable of binding to NBS-1 or PYRIN-1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, biological fluids, and stool samples isolated from a subject, as well as tissues, cells and fluids present within a subject. That is, the detection method of the invention can be used to detect NBS-1 or PYRIN-1 mRNA, protein, or genomic DNA in a biological sample in vitro as well as in vivo. For example, in vitro techniques for detection of NBS-1 or PYRIN-1 mRNA include Northern hybridizations and in situ hybridizations. In vitro techniques for detection of NBS-1 or PYRIN-1 protein include enzyme linked immunosorbent assays (ELISAs), Western blots, immunoprecipitations and immunofluorescence. In vitro techniques for detection of NBS-1 or PYRIN-1 genomic DNA include Southern hybridizations. Furthermore, in vivo techniques for detection of NBS-1 or PYRIN-1 protein include introducing into a subject a labeled anti-NBS-1 or PYRIN-1 antibody. For example, the antibody can be labeled with a radioactive marker whose presence and location in a subject can be detected by standard imaging techniques.

Stool samples may be analyzed using various in vitro techniques, including techniques directed to analysis of DNA, RNA, or protein in the sample (Machiels et al. (2000) *BioTechniques* 28:286-290).

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting NBS-1 or PYRIN-1 protein, mRNA, or genomic DNA, such that the presence of NBS-1 or PYRIN-1 protein, mRNA or genomic DNA is detected in the biological sample, and comparing the presence of NBS-1 or PYRIN-1 protein, mRNA or genomic DNA in the control sample with the presence of NBS-1 or PYRIN-1 protein, mRNA or genomic DNA in the test sample.

The invention also encompasses kits for detecting the presence of NBS-1 or PYRIN-1 in a biological sample (a test sample). Such kits can be used to determine if a subject is suffering from or is at increased risk of developing a disorder associated with aberrant expression of NBS-1 or PYRIN-1 (e.g., an immunological disorder). For example, the kit can comprise a labeled compound or agent capable of detecting NBS-1 or PYRIN-1 protein or mRNA in a biological sample and means for determining the amount of NBS-1 or PYRIN-1 in the sample (e.g., an anti-NBS-1 or PYRIN-1 antibody or an oligonucleotide probe which binds to DNA encoding NBS-1 or PYRIN-1, e.g., SEQ ID NO:1, SEQ ID NO:3, SEQ ID NO:4, SEQ ID NO:6). Kits may also include instruction for observing that the tested subject is suffering from or is at risk of developing a disorder associated with aberrant expression of NBS-1 or PYRIN-1 if the amount of NBS-1 or PYRIN-1 protein or mRNA is above or below a normal level.

For antibody-based kits, the kit may comprise, for example: (1) a first antibody (e.g., attached to a solid support) which binds to NBS-1 or PYRIN-1 protein; and, optionally, (2) a second, different antibody which binds to NBS-1 or PYRIN-1 protein or the first antibody and is conjugated to a detectable agent. For oligonucleotide-based kits, the kit may comprise, for example: (1) a oligonucleotide, e.g., a detectably labeled oligonucleotide, which hybridizes to a NBS-1 or PYRIN-1 nucleic acid sequence or (2) a pair of primers useful for amplifying a NBS-1 or PYRIN-1 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of NBS-1 or PYRIN-1.

2. Prognostic Assays

The methods described herein can furthermore be utilized as diagnostic or prognostic assays to identify subjects having or at risk of developing a disease or disorder associated with aberrant NBS-1 or PYRIN-1 expression or activity. For example, the assays described herein, such as the preceding diagnostic assays or the following assays, can be utilized to identify a subject having or at risk of developing a disorder associated with NBS-1 or PYRIN-1 protein, nucleic acid expression or activity. Alternatively, the prognostic assays can be utilized to identify a subject having or at risk for developing such a disease or disorder. Thus, the present invention provides a method in which a test sample is obtained from a subject and NBS-1 or PYRIN-1 protein or nucleic acid (e.g., mRNA, genomic DNA) is detected, wherein the presence of NBS-1 or PYRIN-1 protein or nucleic acid is diagnostic for a subject having or at risk of developing a disease or disorder associated with aberrant NBS-1 or PYRIN-1 expression or activity. As used herein, a "test sample" refers to a biological sample obtained from a subject of interest. For example, a test sample can be a biological fluid (e.g., serum), cell sample, tissue, or stool sample. Stool samples may be analyzed using various in vitro techniques, including techniques directed to analysis of DNA, RNA, or protein in the sample (Machiels et al. (2000) *BioTechniques* 28:286-290). Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NBS-1 or PYRIN-1 expression or activity. For example, such methods can be used to determine whether a subject can be effectively treated with a specific agent or class of agents (e.g., agents of a type which decrease NBS-1 or PYRIN-1 activity). Thus, the present invention provides methods for determining whether a subject can be effectively treated with an agent for a disorder associated with aberrant NBS-1 or PYRIN-1 expression or activity in which a test sample is obtained and NBS-1 or PYRIN-1 protein or nucleic acid is detected (e.g., wherein the presence of NBS-1 or PYRIN-1 protein or nucleic acid is diagnostic for a subject that can be administered the agent to treat a disorder associated with aberrant NBS-1 or PYRIN-1 expression or activity).

The methods of the invention can also be used to detect genetic lesions or mutations in a NBS-1 or PYRIN-1 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a NBS-1 or PYRIN-1-protein, or the mis-expression of the NBS-1 or PYRIN-1 gene. For example, such genetic lesions can be detected by ascertaining the existence of at least one of 1) a deletion of one or more nucleotides from a NBS-1 or PYRIN-1 gene; 2) an addition of one or more nucleotides to a NBS-1 or PYRIN-1 gene; 3) a substitution of one or more nucleotides of a NBS-1 or PYRIN-1 gene; 4) a chromosomal rearrangement of a NBS-1 or PYRIN-1 gene; 5) an alteration in the level of a messenger RNA transcript of a NBS-1 or PYRIN-1 gene; 6) aberrant modification of a NBS-1 or PYRIN-1 gene, such as of the methylation pattern of the genomic DNA; 7) the presence of a non-wild type splicing pattern of a messenger RNA transcript of a NBS-1 or PYRIN-1 gene (e.g., caused by a mutation in a splice donor or splice acceptor site); 8) a non-wild type level of a NBS-1 or PYRIN-1-protein; 9) allelic loss of a NBS-1 or PYRIN-1 gene; and 10) inappropriate post-translational modification of a NBS-1 or PYRIN-1-protein. As described herein, there are a large number of assay techniques known in the art which can be used for detecting lesions in a NBS-1 or PYRIN-1 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad Sci. USA* 91:360-364), the latter of which can be particularly useful for detecting point mutations in the NBS-1 or PYRIN-1 gene (see, e.g., Abravaya et al. (1995) *Nucleic, Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a NBS-1 or PYRIN-1 gene under conditions such that hybridization and amplification of the NBS-1 or PYRIN-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc Natl. Acad. Sci. USA* 87:1874-1878), transcriptional amplification system (Kwoh, et al. (1989) *Proc. Natl. Acad Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NBS-1 or PYRIN-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in NBS-1 or PYRIN-1 can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). For example, genetic mutations in NBS-1 or PYRIN-1 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NBS-1 or PYRIN-1 gene and detect mutations by comparing the sequence of the sample NBS-1 or PYRIN-1 with the corresponding wild-type (control) sequence. Examples of sequencing reactions include those based on techniques developed by Maxam and Gilbert ((1977) *Proc Natl Acad Sci USA* 74:560) or Sanger ((1977) *Proc. Natl. Acad. Sci. USA* 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohenetal. (1996) *Adv. Chromatogr.* 36:127-162; and Griffin et al. (1993) *Appl. Biochem. Biotechnol.* 38:147-159).

Other methods for detecting mutations in the NBS-1 or PYRIN-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type NBS-1 or PYRIN-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217: 286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NBS-1 or PYRIN-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a NBS-1 or PYRIN-1 sequence, e.g., a wild-type NBS-1 or PYRIN-1 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NBS-1 or PYRIN-1 genes. For example, single strand conformation polymorphism (SSCP) may be used to detect differences in electrophoretic mobility between mutant and wild type nucleic acids (Orita et al. (1989) *Proc Natl. Acad Sci USA:* 86:2766, see also Cotton (1993) *Mutat. Res.* 285:125-144; and Hayashi (1992) *Genet Anal Tech Appl* 9:73-79). Single-stranded DNA fragments of sample and control NBS-1 or PYRIN-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA,* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NBS-1 or PYRIN-1 gene.

Furthermore, any cell type or tissue, preferably peripheral blood leukocytes, in which NBS-1 or PYRIN-1 is expressed may be utilized in the prognostic assays described herein.

3. Pharmacogenomics

Agents, or modulators which have a stimulatory or inhibitory effect on NBS-1 or PYRIN-1 activity (e.g., NBS-1 or PYRIN-1 gene expression) as identified by a screening assay described herein can be administered to individuals to treat (prophylactically or therapeutically) disorders (e.g., a neurodegenerative disease such as Alzheimer's disease) associated with aberrant NBS-1 or PYRIN-1 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NBS-1 or PYRIN-1 protein, expression of NBS-1 or PYRIN-1 nucleic acid, or mutation content of NBS-1 or PYRIN-1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultrarapid metabolizers who do not respond to standard doses. Recently, the molecular basis of ultra-rapid metabolism has been identified to be due to CYP2D6 gene amplification.

Thus, the activity of NBS-1 or PYRIN-1 protein, expression of NBS-1 or PYRIN-1 nucleic acid, or mutation content of NBS-1 or PYRIN-1 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NBS-1 or PYRIN-1 modulator, such as a modulator identified by one of the exemplary screening assays described herein.

4. Monitoring of Effects During Clinical Trials

Monitoring the influence of agents (e.g., drugs, compounds) on the expression or activity of NBS-1 or PYRIN-1 (e.g., the ability to modulate aberrant cell proliferation and/or differentiation) can be applied not only in basic drug screening, but also in clinical trials. For example, the effectiveness of an agent determined by a screening assay as described herein to increase NBS-1 or PYRIN-1 gene expression, protein levels, or upregulate NBS-1 or PYRIN-1 activity, can be monitored in clinical trails of subjects exhibiting decreased NBS-1 or PYRIN-1 gene expression, protein levels, or downregulated NBS-1 or PYRIN-1 activity. Alternatively, the effectiveness of an agent determined by a screening assay to decrease NBS-1 or PYRIN-1 gene expression, protein levels, or downregulated NBS-1 or PYRIN-1 activity, can be monitored in clinical trials of subjects exhibiting increased NBS-1 or PYRIN-1 gene expression, protein levels, or upregulated NBS-1 or PYRIN-1 activity. In such clinical trials, the expression or activity of NBS-1 or PYRIN-1 and, preferably, other genes that have been implicated in, for example, a cellular proliferation disorder can be used as a "read out" or markers of the immune responsiveness of a particular cell.

For example, and not by way of limitation, genes, including NBS-1 or PYRIN-1, that are modulated in cells by treatment with an agent (e.g., compound, drug or small molecule) which modulates NBS-1 or PYRIN-1 activity (e.g., identified in a screening assay as described herein) can be identified. Thus, to study the effect of agents on cellular proliferation disorders, for example, in a clinical trial, cells can be isolated and RNA prepared and analyzed for the levels of expression of NBS-1 or PYRIN-1 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NBS-1 or PYRIN-1 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a NBS-1 or PYRIN-1 protein, mRNA, or genomic DNA in the preadministration sample; (iii) obtaining one or more post-administration samples from the subject; (iv) detecting the level of expression or activity of the NBS-1 or PYRIN-1 protein, mRNA, or genomic DNA in the post-administration samples; (v) comparing the level of expression or activity of the NBS-1 or PYRIN-1 protein, mRNA, or genomic DNA in the pre-administration sample with the NBS-1 or PYRIN-1 protein, mRNA, or genomic DNA in the post administration sample or samples; and (vi) altering the administration of the agent to the subject accordingly. For example, increased administration of the agent may be desirable to increase the expression or activity of NBS-1 or PYRIN-1 to higher levels than detected, i.e., to increase the effectiveness of the agent. Alternatively, decreased administration of the agent may be desirable to decrease expression or activity of NBS-1 or PYRIN-1 to lower levels than detected, i.e., to decrease the effectiveness of the agent.

5. Transcriptional Profiling

The NBS-1 or PYRIN-1 nucleic acid molecules described herein, including small oligonucleotides, can be used in transcriptionally profiling. For example, these nucleic acids can be used to examine the expression of NBS-1 or PYRIN-1 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of NBS-1 or PYRIN-1, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant NBS-1 or PYRIN-1 expression or activity, examples of which are provided herein.

1. Prophylactic Methods

In one aspect, the invention provides a method for preventing in a subject, a disease or condition associated with an aberrant NBS-1 or PYRIN-1 expression or activity, by administering to the subject an agent which modulates NBS-1 or PYRIN-1 expression or at least one NBS-1 or PYRIN-1 activity. Subjects at risk for a disease which is caused or contributed to by aberrant NBS-1 or PYRIN-1 expression or activity can be identified by, for example, any or a combination of diagnostic or prognostic assays as described herein. Administration of a prophylactic agent can occur prior to the manifestation of symptoms characteristic of the NBS-1 or PYRIN-1 aberrancy, such that a disease or disorder is prevented or, alternatively, delayed in its progression. Depending on the type of NBS-1 or PYRIN-1 aberrancy, for example, a NBS-1 or PYRIN-1 agonist or NBS-1 or PYRIN-1 antagonist agent can be used for treating the subject. The appropriate agent can be determined based on screening assays described herein.

2. Therapeutic Methods

Another aspect of the invention pertains to methods of modulating NBS-1 or PYRIN-1 expression or activity for therapeutic purposes. The modulatory method of the invention involves contacting a cell with an agent that modulates one or more of the activities of NBS-1 or PYRIN-1 protein activity associated with the cell. An agent that modulates NBS-1 or PYRIN-1 protein activity can be an agent as described herein, such as a nucleic acid or a protein, a naturally-occurring cognate ligand of a NBS-1 or PYRIN-1 protein, a peptide, a NBS-1 or PYRIN-1 peptidomimetic, or other small molecule. In one embodiment, the agent stimulates one or more of the biological activities of NBS-1 or PYRIN-1 protein. Examples of such stimulatory agents include active NBS-1 or PYRIN-1 protein and a nucleic acid molecule encoding NBS-1 or PYRIN-1 that has been introduced into the cell. In another embodiment, the agent inhibits one or more of the biological activities of NBS-1 or PYRIN-1 protein. Examples of such inhibitory agents include antisense NBS-1 or PYRIN-1 nucleic acid molecules and anti-NBS-1 or PYRIN-1 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NBS-1 or PYRIN-1 protein or nucleic acid molecule or a disorder related to NBS-1 or PYRIN-1 expression or activity. In one embodiment, the method involves administering an agent (e.g., an agent identified by a screening assay described herein), or combination of agents that modulates (e.g., upregulates or downregulates) NBS-1 or PYRIN-1 expression or activity. In another embodiment, the method involves administering a NBS-1 or PYRIN-1 protein or nucleic acid molecule as therapy to compensate for reduced or aberrant NBS-1 or PYRIN-1 expression or activity. Stimulation of NBS-1 or PYRIN-1 activity is desirable in situations in which NBS-1 or PYRIN-1 is abnormally downregulated and/or in which increased NBS-1 or PYRIN-1 activity is likely to have a beneficial effect. Conversely, inhibition of NBS-1 or PYRIN-1 activity is desirable in situations in which NBS-1 or PYRIN-1 is abnormally upregulated, e.g., in myocardial infarction, and/or in which decreased NBS-1 or PYRIN-1 activity is likely to have a beneficial effect.

This invention is further illustrated by the following examples which should not be construed as limiting. The contents of all references, patents and published patent applications cited throughout this application are hereby incorporated by reference.

II. Isolated Nucleic Acid Molecules

Isolated nucleic acid molecules that encode NBS-1 or PYRIN-1 proteins or biologically active portions thereof, as well as nucleic acid molecules sufficient for use as hybridization probes to identify NBS-1 or PYRIN-1-encoding nucleic acids (e.g., NBS-1 or PYRIN-1 mRNA) and fragments for use as PCR primers for the amplification or mutation of NBS-1 or PYRIN-1 nucleic acid molecules are useful in the methods of the invention. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated NBS-1 or PYRIN-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule which is complementary to a given nucleotide sequence is one which is sufficiently complementary to the given nucleotide sequence that it can hybridize to the given nucleotide sequence thereby forming a stable duplex.

NBS-1 or PYRIN-1 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

Nucleic acid molecules can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to NBS-1 or PYRIN-1 nucleotide sequences can be prepared by standard synthetic techniques, e.g., using an automated DNA synthesizer.

Fragments of NBS-1 or PYRIN-1 nucleic acid molecules, for example, a fragment which can be used as a probe or primer or a fragment encoding a biologically active portion of NBS-1 or PYRIN-1 can be useful in the methods of the invention. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:4, SEQ ID NO:6, or of a naturally occurring mutant of one of SEQ ID NO:1, SEQ ID NO:3, SEQ ID NO:4, or SEQ ID NO:6.

Probe can comprise a label group attached thereto, e.g., a radioisotope, a fluorescent compound, an enzyme, or an enzyme co-factor. Such probes can be used as a part of a diagnostic test kit for identifying allelic variants and orthologs of the NBS-1 or PYRIN-1 proteins of the present invention, identifying cells or tissue which mis-express a NBS-1 or PYRIN-1 protein, such as by measuring a level of a NBS-1 or PYRIN-1-encoding nucleic acid in a sample of cells from a subject, e.g., detecting NBS-1 or PYRIN-1 mRNA levels or determining whether a genomic NBS-1 or PYRIN-1 gene has been mutated or deleted.

A nucleic acid fragment encoding a "biologically active portion" of NBS-1 or PYRIN-1 can be prepared by isolating a portion of SEQ ID NO:1, SEQ ID NO:3, SEQ ID NO:4, or SEQ ID NO:6, which encodes a polypeptide having a NBS-1 or PYRIN-1 biological activity, expressing the encoded portion of NBS-1 or PYRIN-1 protein (e.g., by recombinant expression in vitro) and assessing the activity of the encoded portion of NBS-1 or PYRIN-1.

Nucleic acid molecules that differ from the nucleotide sequence of SEQ ID NO:1, SEQ ID NO:3, SEQ ID NO:4, and SEQ ID NO:6, due to degeneracy of the genetic code and thus encode the same NBS-1 or PYRIN-1 protein as that encoded by the nucleotide sequence shown in SEQ ID NO:1, SEQ ID NO:3, SEQ ID NO:4, or SEQ ID NO:6, are also useful.

It will be appreciated by those skilled in the art that DNA sequence polymorphisms that lead to changes in the amino acid sequences of NBS-1 or PYRIN-1 may exist within a population (e.g., the human population). Such genetic polymorphism in the NBS-1 or PYRIN-1 gene may exist among individuals within a population due to natural allelic variation, and such variants can be useful in the methods of the invention.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, New York (1989), 6.3.1-6.3.6. An, non-limiting example of stringent hybridization conditions are hybridization in 6× sodium chloride/sodium citrate (SSC) at about 45° C., followed by one or more washes in 0.2×SSC, 0.1% SDS at 50-65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the NBS-1 or PYRIN-1 sequence that may exist in the population, the skilled artisan will further appreciate that changes can be introduced by mutation into the nucleotide sequence of SEQ ID NO:1, SEQ ID NO:3, SEQ ID NO:4, or SEQ ID NO:6, thereby leading to changes in the amino acid sequence of the encoded protein without altering the functional ability of the protein and that such variants are also useful. For example, one can make nucleotide substitutions leading to amino acid substitutions at "non-essential" amino acid residues. A "non-essential" amino acid residue is a residue that can be altered from the wild-type sequence of NBS-1 or PYRIN-1 protein without altering the biological activity, whereas an "essential" amino acid residue is required for biological activity. For example, amino acid residues that are conserved among the NBS-1 or PYRIN-1, proteins of various species are predicted to be particularly unamenable to alteration.

For example, conserved domains are less likely to be amenable to mutation. Other amino acid residues, however, (e.g., those that are not conserved or only semi-conserved among NBS-1 or PYRIN-1 of various species) may not be essential for activity and thus are likely to be amenable to alteration.

NBS-1 or PYRIN-1 proteins that contain changes in amino acid residues that are not essential for activity are useful in the invention. Such NBS-1 or PYRIN-1 proteins differ in amino acid sequence from SEQ ID NO:2 or SEQ ID NO:5 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2 or SEQ ID NO:5.

An isolated nucleic acid molecule encoding a NBS-1 or PYRIN-1 protein having a sequence which differs from that of SEQ ID NO:1, SEQ ID NO:3, SEQ ID NO:4, or SEQ ID NO:6, can be created by introducing one or more nucleotide substitutions, additions or deletions into the nucleotide sequence of NBS-1 or PYRIN-1 (SEQ ID NO:1, SEQ ID NO:3, SEQ ID NO:4, or SEQ ID NO:6, such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in NBS-1 or PYRIN-1 is preferably replaced with another amino acid residue from the same side chain family. Alternatively, mutations can be introduced randomly along all or part of a NBS-1 or PYRIN-1 coding sequence, such as by saturation mutagenesis, and the resultant mutants can be screened for NBS-1 or PYRIN-1 biological activity to identify mutants that retain activity. Following mutagenesis, the encoded protein can be expressed recombinantly and the activity of the protein can be determined.

In an embodiment, a mutant NBS-1 or PYRIN-1 protein can be assayed for: (1) the ability to form protein:protein interactions with proteins in the apoptotic signaling pathway; (2) the ability to bind a NBS-1 or PYRIN-1 ligand; or (3) the ability to bind to an intracellular target protein.

The present invention encompasses the use of antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NBS-1 or PYRIN-1 coding strand, or to only a portion thereof, e.g., all or part of the protein coding region (or open reading frame). An antisense nucleic acid molecule can be antisense to a noncoding region of the coding strand of a nucleotide sequence encoding NBS-1 or PYRIN-1. The noncoding regions ("5' and 3' untranslated regions") are the 5' and 3' sequences that flank the coding region and are not translated into amino acids. Given the coding strand sequences encoding NBS-1 or PYRIN-1 disclosed herein, antisense nucleic acids of the invention can be designed according to the rules of Watson and Crick base pairing. The antisense nucleic acid molecule can be complementary to the entire coding region of NBS-1 or PYRIN-1 mRNA, but more preferably is an oligonucleotide which is antisense to only a portion of the coding or noncoding region of NBS-1 or PYRIN-1 mRNA. For example, the antisense oligonucleotide can be complementary to the region surrounding the translation start site of NBS-1 or PYRIN-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Antisense nucleic acid molecules are typically administered to a subject or generated in situ such that they hybridize with or bind to cellular mRNA and/or genomic DNA encoding a NBS-1 or PYRIN-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecules can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave NBS-1 or PYRIN-1 mRNA transcripts to thereby inhibit translation of NBS-1 or PYRIN-1 mRNA. A ribozyme having specificity for a NBS-1 or PYRIN-1-encoding nucleic acid can be designed based upon the nucleotide sequence of a NBS-1 or PYRIN-1 cDNA disclosed herein. For example, a derivative of a Tetrahymena L-19 IVS RNA can be constructed in which the nucleotide sequence of the active site is complementary to the nucleotide sequence to be cleaved in a NBS-1 or PYRIN-1-encoding mRNA. See, e.g., Cech et al. U.S. Pat. No. 4,987,071; and Cech et al. U.S. Pat. No. 5,116,742. Alternatively, NBS-1 or PYRIN-1 mRNA can be used to select a catalytic RNA having a specific ribonuclease activity from a pool of RNA molecules. See, e.g., Bartel and Szostak (1993) *Science* 261: 1411-1418.

Nucleic acid molecules which form triple helical structures are useful in certain aspects of the invention. For example, NBS-1 or PYRIN-1 gene expression can be inhibited by targeting nucleotide sequences complementary to the regulatory region of the NBS-1 or PYRIN-1 (e.g., the NBS-1 or PYRIN-1 promoter and/or enhancers) to form triple helical structures that prevent transcription of the NBS-1 or PYRIN-1 gene in target cells. See generally, Helene (1991) *Anticancer Drug Des.* 6:569-84; Helene (1992) *Ann. N.Y. Acad Sci.* 660:27-36; and Maher (1992) *Bioassays* 14:807-15.

NBS-1 and PYRIN-1 nucleic acid molecules can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl Acad Sci. USA* 93:14670-675.

PNAs of NBS-1 or PYRIN-1 can be used for therapeutic and diagnostic applications. For example, PNAs can be used as antisense or antigene agents for sequence-specific modulation of gene expression by, e.g., inducing transcription or translation arrest or inhibiting replication. PNAs of NBS-1 or PYRIN-1 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) *Proc. Natl. Acad Sci USA* 93: 14670-675).

PNAs of NBS-1 or PYRIN-1 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NBS-1 or PYRIN-1 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) *Nucleic Acids Research* 24:3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) *Nucleic Acid Res.* 17:5973-88). PNA monomers are then coupled in a stepwise manner to produce a chimeric molecule with a 5' PNA segment and a 3' DNA segment (Finn et al. (1996) *Nucleic Acids Research* 24:3357-63). Alternatively, chimeric molecules can be synthesized with a 5' DNA segment and a 3' PNA segment (Peterser et al. (1975) *Bioorganic Med. Chem. Lett.* 5:1119-11124).

The oligonucleotide may include other appended groups such as peptides (e.g., for targeting host cell receptors in vivo), or agents facilitating transport across the cell membrane (see, e.g., Letsinger et al. (1989) *Proc Natl. Acad. Sci. USA* 86:6553-6556; Lemaitre et al. (1987) *Proc Natl Acad Sci USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

III. Isolated NBS-1 or PYRIN-1 Proteins and Anti-NBS-1 or PYRIN-1 Antibodies

NBS-1 or PYRIN-1 proteins, and biologically active portions thereof, as well as polypeptide fragments suitable for use as immunogens to raise anti-NBS-1 or PYRIN-1 antibodies are useful in the methods of the invention. Native NBS-1 or PYRIN-1 proteins can be isolated from cells or tissue sources by an appropriate purification scheme using standard protein purification techniques. NBS-1 or PYRIN-1 proteins can also be produced by recombinant DNA techniques. Alternative to recombinant expression, a NBS-1 or PYRIN-1 protein or polypeptide can be synthesized chemically using standard peptide synthesis techniques.

An "isolated" or "purified" protein or biologically active portion thereof is substantially free of cellular material or other contaminating proteins from the cell or tissue source from which the NBS-1 or PYRIN-1 protein is derived, or substantially free from chemical precursors or other chemicals when chemically synthesized. The language "substantially free of cellular material" includes preparations of NBS-1 or PYRIN-1 protein in which the protein is separated from cellular components of the cells from which it is isolated or recombinantly produced. Trius, NBS-1 or PYRIN-1 protein that is substantially free of cellular material includes preparations of NBS-1 or PYRIN-1 protein having less than about 30%, 20%, 10%, or 5% (by dry weight) of non- NBS-1 or PYRIN-1 protein (also referred to herein as a "contaminating protein"). When the NBS-1 or PYRIN-1 protein or biologically active portion thereof is recombinantly produced, it is also preferably substantially free of culture medium, i.e., culture medium represents less than about 20%, 10%, or 5% of the volume of the protein preparation. When NBS-1 or PYRIN-1 protein is produced by chemical synthesis, it is preferably substantially free of chemical precursors or other chemicals, i.e., it is separated from chemical precursors or other chemicals which are involved in the synthesis of the protein. Accordingly such preparations of NBS-1 or PYRIN-1 protein have less than about 30%, 20%, 10%, 5% (by dry weight) of chemical precursors or non- NBS-1 or PYRIN-1 chemicals.

Biologically active portions of a NBS-1 or PYRIN-1 protein include peptides comprising amino acid sequences sufficiently identical to or derived from the amino acid sequence of the NBS-1 or PYRIN-1 protein (e.g., the amino acid sequence shown in SEQ ID NO:2 or SEQ ID NO:5), which include less amino acids than the full length NBS-1 or PYRIN-1 protein, and exhibit at least one activity of a NBS-1 or PYRIN-1 protein. Typically, biologically active portions comprise a domain or motif with at least one activity of the NBS-1 or PYRIN-1 protein. A biologically active portion of a NBS-1 or PYRIN-1 protein can be a polypeptide which is, for example, 10, 25, 50, 72, 100, 125, 150, 175, 200, 225, 250, 272, 300, 325, 350, 375, 400, 425, 450 or more amino acids in length. Preferred biologically active polypeptides include one or more identified NBS-1 or PYRIN-1 structural domains, e.g., the pyrin domain.

Moreover, other biologically active portions, in which other regions of the protein are deleted, can be prepared by recombinant techniques and evaluated for one or more of the functional activities of a native NBS-1 or PYRIN-1 protein.

Human NBS-1 and human PYRIN-1 proteins have the amino acid sequences of SEQ ID NO:2 or SEQ ID NO:5. Other useful NBS-1 or PYRIN-1 proteins are substantially identical to SEQ ID NO:2 or SEQ ID NO:5 and retain the functional activity of the protein of SEQ ID NO:2 or SEQ ID NO:5, yet differ in amino acid sequence due to natural allelic variation or mutagenesis.

A useful NBS-1 or PYRIN-1 protein is a protein which includes an amino acid sequence at least about 45%, preferably 55%, 65%, 75%, 85%, 95%, or 99% identical to the amino acid sequence of SEQ ID NO:2 or SEQ ID NO:5, and retains the functional activity of the NBS-1 or PYRIN-1 protein of SEQ ID NO:2 or SEQ ID NO:5.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad Sci USA* 87:2264-2268, modified as in Karlin and Altschul (1993) *Proc Nat'l Acad Sci. USA* 90:5873-5877. Such an algorithm is incorporated into the NBLAST and XBLAST programs of Altschul, et al. (1990) *J Mol. Biol.* 215:403-410. BLAST nucleotide searches can be performed with the NBLAST program, score=100, wordlength=12 to obtain nucleotide sequences similar or homologous to NBS-1 or PYRIN-1 nucleic acid molecules of the invention. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used. Another preferred example of a mathematical algorithm utilized for the comparison of sequences is the Needleman and Wunsch (*J. Mol. Biol.* (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

NBS-1 or PYRIN-1 chimeric or fusion proteins are also useful in the methods of the invention. As used herein, a NBS-1 or PYRIN-1 "chimeric protein" or "fusion protein-"comprises a NBS-1 or PYRIN-1 polypeptide operatively linked to a non- NBS-1 or PYRIN-1 polypeptide. A "NBS-1 or PYRIN-1 polypeptide" refers to a polypeptide having an amino acid sequence corresponding to all or a portion (preferably a biologically active portion) of a NBS-1 or PYRIN-1, whereas a "non-NBS-1 or PYRIN-1 polypeptide" refers to a polypeptide having an amino acid sequence corresponding to a protein which is not substantially identical to the NBS-1 or PYRIN-1 protein, e.g., a protein which is different from the NBS-1 or PYRIN-1 proteins and which is derived from the same or a different organism. Within the fusion protein, the term "operatively linked" is intended to indicate that the NBS-1 or PYRIN-1 polypeptide and the non-NBS-1 or PYRIN-1 polypeptide are fused in-frame to each other. The heterologous polypeptide can be fused to the N-terminus or C-terminus of the NBS-1 or PYRIN-1 polypeptide.

One useful fusion protein is a GST fusion protein in which the NBS-1 or PYRIN-1 sequences are fused to the C-terminus of the GST sequences. Such fusion proteins can facilitate the purification of recombinant NBS-1 or PYRIN-1. In another embodiment, the fusion protein contains a signal sequence from another protein. In certain host cells (e.g., mammalian host cells), expression and/or secretion of NBS-1 or PYRIN-1 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

NBS-1 or PYRIN-1-immunoglobulin fusion protein in which all or part of NBS-1 or PYRIN-1 is fused to sequences derived from a member of the immunoglobulin protein family are also useful. The NBS-1 or PYRIN-1-immunoglobulin fusion proteins can be incorporated into pharmaceutical compositions and administered to a subject to inhibit an interaction between a NBS-1 or PYRIN-1 ligand and a NBS-1 or PYRIN-1 protein on the surface of a cell, to thereby suppress NBS-1 or PYRIN-1-mediated signal transduction in vivo. The NBS-1 or PYRIN-1-immunoglobulin fusion proteins can be used to affect the bioavailability of a NBS-1 or PYRIN-1 cognate ligand. Inhibition of the NBS-1 or PYRIN-1 ligand/NBS-1 or PYRIN-1 interaction may be useful therapeutically for both the treatment of proliferative and differentiative disorders, as well as modulating (e.g., promoting or inhibiting) cell survival. Moreover, the NBS-1 or PYRIN-1-immunoglobulin fusion proteins can be used as immunogens to produce anti-NBS-1 or PYRIN-1 antibodies in a subject, to purify NBS-1 or PYRIN-1 ligands and in screening assays to identify molecules which inhibit the interaction of NBS-1 or PYRIN-1 with a NBS-1 or PYRIN-1 ligand.

Preferably, a NBS-1 or PYRIN-1 chimeric or fusion proteins can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A NBS-1 or PYRIN-1-encoding nucleic acid can be cloned into such an expression vector such that the fusion moiety is linked in-frame to the NBS-1 or PYRIN-1 protein.

Variants of the NBS-1 or PYRIN-1 proteins which function as either NBS-1 or PYRIN-1 agonists (mimetics) or as NBS-1 or PYRIN-1 antagonists are useful in the invention. Variants of the NBS-1 or PYRIN-1 proteins can be generated by mutagenesis, e.g., discrete point mutation or truncation of the NBS-1 or PYRIN-1 proteins. An agonist of the NBS-1 or PYRIN-1 protein can retain substantially the same, or a subset, of the biological activities of the naturally occurring form of the NBS-1 or PYRIN-1 protein. An antagonist of the NBS-1 or PYRIN-1 protein can inhibit one or more of the activities of the naturally occurring form of the NBS-1 or PYRIN-1 protein by, for example, competitively binding to a downstream or upstream member of a cellular signaling cascade which includes the NBS-1 or PYRIN-1 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the NBS-1 or PYRIN-1 proteins.

Variants of the NBS-1 or PYRIN-1 protein which function as either NBS-1 or PYRIN-1 agonists (mimetics) or as NBS-1 or PYRIN-1 antagonists can be identified by screening combinatorial libraries of mutants, e.g., truncation mutants of the NBS-1 or PYRIN-1 protein for NBS-1 or PYRIN-1 protein agonist or antagonist activity. In one embodiment, a variegated library of NBS-1 or PYRIN-1 variants is generated by combinatorial mutagenesis at the nucleic acid level and is encoded by a variegated gene library. A variegated library of NBS-1 or PYRIN-1 variants can be produced by, for example, enzymatically ligating a mixture of synthetic oligonucleotides into gene sequences such that a degenerate set of potential NBS-1 or PYRIN-1 sequences is expressible as individual polypeptides, or alternatively, as a set of larger fusion proteins (e.g., for phage display) containing the set of NBS-1 or PYRIN-1 sequences therein. There are a variety of methods which can be used to produce libraries of potential NBS-1 or PYRIN-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NBS-1 or PYRIN-1 sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

Useful fragments of NBS-1 or PYRIN-1, include fragments comprising or consisting of a domain or subdomain described herein, e.g., LRR or NBS or pyrin domain.

In addition, libraries of fragments of the NBS-1 or PYRIN-1 protein coding sequence can be used to generate a variegated population of NBS-1 or PYRIN-1 fragments for screening and subsequent selection of variants of a NBS-1 or PYRIN-1 protein. In one embodiment, a library of coding sequence fragments can be generated by treating a double stranded PCR fragment of a NBS-1 or PYRIN-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the NBS-1 or PYRIN-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NBS-1 or PYRIN-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify NBS-1 or PYRIN-1 variants (Arkin and Yourvan (1992) *Proc Natl Acad Sci. USA* 89:7811-7815; Delgrave et al. (1993) *Protein Engineering* 6(3): 327-331).

An isolated NBS-1 or PYRIN-1 protein, or a portion or fragment thereof, can be used as an immunogen to generate antibodies that bind NBS-1 or PYRIN-1 using standard techniques for polyclonal and monoclonal antibody preparation. The full-length NBS-1 or PYRIN-1 protein can be used or, alternatively, the invention provides antigenic peptide fragments of NBS-1 or PYRIN-1 for use as immunogens. The antigenic peptide of NBS-1 or PYRIN-1 comprises at least 8 (preferably 10, 15, 20, or 30) amino acid residues of the amino acid sequence shown in SEQ ID NO:2 or SEQ ID NO:5 and encompasses an epitope of NBS-1 or PYRIN-1 such that an antibody raised against the peptide forms a specific immune complex with NBS-1 or PYRIN-1.

Useful antibodies include antibodies which bind to a domain or subdomain of NBS-1 or PYRIN-1 described herein (e.g., a LRR or NBS or pyrin domain).

Preferred epitopes encompassed by the antigenic peptide are regions of NBS-1 or PYRIN-1 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIGS. 3 and 6).

A NBS-1 or PYRIN-1 immunogen typically is used to prepare antibodies by immunizing a suitable subject, (e.g., rabbit, goat, mouse or other mammal) with the immunogen. An appropriate immunogenic preparation can contain, for example, recombinantly expressed NBS-1 or PYRIN-1 protein or a chemically synthesized NBS-1 or PYRIN-1 polypeptide. The preparation can further include an adjuvant, such as Freund's complete or incomplete adjuvant, or similar immunostimulatory agent. Immunization of a suitable subject with an immunogenic NBS-1 or PYRIN-1 preparation induces a polyclonal anti-NBS-1 or PYRIN-1 antibody response.

The term "antibody" as used herein refers to immunoglobulin molecules and immunologically active portions of immunoglobulin molecules, i.e., molecules that contain an antigen binding site which specifically binds an antigen, such as NBS-1 or PYRIN-1. A molecule which specifically binds to NBS-1 or PYRIN-1 is a molecule which binds NBS-1 or PYRIN-1, but does not substantially bind other molecules in a sample, e.g., a biological sample, which naturally contains NBS-1 or PYRIN-1. Examples of immunologically active portions of immunoglobulin molecules include F(ab) and F(ab')2 fragments which can be generated by treating the antibody with an enzyme such as pepsin. The invention provides polyclonal and monoclonal antibodies that bind NBS-1 or PYRIN-1. The term "monoclonal antibody" or "monoclonal antibody composition", as used herein, refers to a population of antibody molecules that contain only one species of an antigen binding site capable of immunoreacting with a particular epitope of NBS-1 or PYRIN-1. A monoclonal antibody composition thus typically displays a single binding affinity for a particular NBS-1 or PYRIN-1 protein with which it immunureacts.

Polyclonal anti-NBS-1 or PYRIN-1 antibodies can be prepared as described above by immunizing a suitable subject with a NBS-1 or PYRIN-1 immunogen. The anti-NBS-1 or PYRIN-1 antibody titer in the immunized subject can be monitored over time by standard techniques, such as with an enzyme linked immunosorbent assay (ELISA) using immobilized NBS-1 or PYRIN-1. If desired, the antibody molecules directed against NBS-1 or PYRIN-1 can be isolated from the mammal (e.g., from the blood) and further purified by well-known techniques, such as protein A chromatography to obtain the IgG fraction. At an appropriate time after immunization, e.g., when the anti-NBS-1 or PYRIN-1 antibody titers are highest, antibody-producing cells can be obtained from the subject and used to prepare monoclonal antibodies by standard techniques, such as the hybridoma technique originally described by Kohler and Milstein (1975) *Nature* 256.495-497, the human B cell hybridoma technique (Kozbor et al. (1983) *Immunol Today* 4:72), the EBV-hybridoma technique (Cole et al. (1985),

*Monoclonal Antibodies and Cancer Therapy*, Alan R. Liss, Inc., pp. 77-96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a NBS-1 or PYRIN-1 immunogen as described above, and the culture supernatants of the resulting hybridoma cells are screened to identify a hybridoma producing a monoclonal antibody that binds NBS-1 or PYRIN-1.

Any of the many well known protocols used for fusing lymphocytes and immortalized cell lines can be applied for the purpose of generating an anti-NBS-1 or PYRIN-1 monoclonal antibody (see, e.g., Current Protocols in Immunology, supra; Galfre et al. (1977) *Nature* 266:55052; R. H. Kenneth, in Monoclonal Antibodies: A New Dimension In Biological Analyses, Plenum Publishing Corp., New York, N.Y. (1980); and Lerner (1981) *Yale J. Biol Med.*, 54:387-402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from American Type Culture Collection (ATCC. Mannassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NBS-1 or PYRIN-1, e.g., using a standard ELISA assay.

Alternative to preparing monoclonal antibody-secreting hybridomas, a monoclonal anti-NBS-1 or PYRIN-1 antibody can be identified and isolated by screening a recombinant combinatorial immunoglobulin library (e.g., an antibody phage display library) with NBS-1 or PYRIN-1 to thereby isolate immunoglobulin library members that bind NBS-1 or PYRIN-1. Kits for generating and screening phage display libraries are commercially available (e.g., the Pharmacia Recombinant Phage Antibody System, Catalog No. 27-9400-01; and the Stratagene SurfZAP Phage Display Kit Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod Hybridomas* 3:81-85; Huse et al. (1989) *Science* 246:1275-1281; Griffiths et al. (1993) *EMBO J.* 12:725-734.

Additionally, recombinant anti-NBS-1 or PYRIN-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et ;1. (1987) *Proc. Natl. Acad Sci USA* 84:3439-3443; Liu et al. (1987) *J Immunol.* 139:3521-3526; Sun et al. (1987) *Proc. Natl. Acad. Sci USA* 84:214-218; Nishimura et al. (1987) *Canc. Res.* 47:999-1005; Wood et al. (1985) *Nature* 314:446-449; and Shawetal. (1988) *J. Natl. Cancer Inst.* 80:1553-1559); Morrison, (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-NBS-1 or PYRIN-1 antibody (e.g., monoclonal antibody) can be used to isolate NBS-1 or PYRIN-1 by standard techniques, such as affinity chromatography or immunoprecipitation. An anti-NBS-1 or PYRIN-1 antibody can facilitate the purification of natural NBS-1 or PYRIN-1 from cells and of recombinantly produced NBS-1 or PYRIN-1 expressed in host cells. Moreover, an anti-NBS-1 or PYRIN-1 antibody can be used to detect NBS-1 or PYRIN-1 protein (e.g., in a cellular lysate or cell supernatant) in order to evaluate the abundance and pattern of expression of the NBS-1 or PYRIN-1 protein. Anti-NBS-1 or PYRIN-1 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in *Monoclonal Antibodies and Cancer Therapy*, Reisfeld et al. (eds.), pp. 243-56 (Alan R. Liss, Inc. 1985); Hellstrom et al., "Antibodies for Drug Delivery", in *Controlled Drug Delivery* (2nd Ed.), Robinson et al. (eds.), pp. 623-53 (Marcel Dekker, Inc. 1987); Thorpe, "Antibody Carriers of Cytotoxic Agents in Cancer Therapy: A Review", in *Monoclonal Antibodies '84: Biological and Clinical Applications*, Pinchera et al. (eds.), pp. 475-506 (1985); "Analysis, Results, and Future Prospective of The Therapeutic Use of Radiolabeled Antibody In Cancer Therapy", in *Monoclonal Antibodies for Cancer Detection and Therapy*, Baldwin et al. (eds.), pp. 303-16 (Academic Press 1985), and Thorpe et al., "The Preparation and Cytotoxic Properties of Antibody-Toxin Conjugates", *Immunol Rev.*, 62:119-58 (1982). Alternatively, an antibody can be conjugated to a second antibody to form an antibody heteroconjugate as described by Segal in U.S. Pat. No. 4,676,980.

In addition, antibodies, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a NBS-1 or PYRIN-1 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a NBS-1 or PYRIN-1 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a NBS-1 or PYRIN-1 polypeptide of the present invention wherein the composition comprises a polypeptide or polynucleotide of NBS-1 or PYRIN-1. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

IV. Recombinant Expression Vectors and Host Cells

Another aspect of the invention pertains to vectors, preferably expression vectors, containing a nucleic acid encoding NBS-1 or PYRIN-1 (or a portion thereof) that are useful in the methods of the invention. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

Recombinant expression vectors comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: *Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NBS-1 or PYRIN-1 proteins, mutant forms of NBS-1 or PYRIN-1, fusion proteins, etc.).

The recombinant expression vectors can be designed for expression of NBS-1 or PYRIN-1 in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: *Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., Gene Expression Technology: *Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident ë prophage harboring a T7 gn1 gene under the transcriptional control of the lacUV5 promoter.

One strategy to maximize recombinant protein expression in *E. coli* is to express the protein in a bacterial having an impaired capacity to proteolytically cleave the recombinant protein (Gottesman, Gene Expression Technology: *Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the NBS-1 or PYRIN-1 expression vector is a yeast expression vector. Examples of vectors for expression in yeast *S. cerivisae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) *Yeast* 9:1299-1308), pYPGE15 (Brunelli and Pall, (1993) *Yeast* 9:1309-1318), pACTII (Dr. S. E. Elledge, Baylor College of Medicine), and picZ (In Vitrogen Corp, San Diego, Calif.).

Alternatively, NBS-1 or PYRIN-1 can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840), pCI (Promega), and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NBS-1 or PYRIN-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Also useful in the invention are host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NBS-1 or PYRIN-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding NBS-1 or PYRIN-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a NBS-1 or PYRIN-1 protein. Accordingly, the invention further provides methods for producing NBS-1 or PYRIN-1 protein using the host cells of the invention. In one embodiment, the method comprises culturing the host cell of the invention (into which a recombinant expression vector or isolated nucleic acid molecule encoding NBS-1 or PYRIN-1 has been introduced) in a suitable medium such that NBS-1 or PYRIN-1 protein is produced. In another embodiment, the method further comprises isolating NBS-1 or PYRIN-1 from the medium or the host cell.

NBS-1 and PYRIN-1 nucleic acid molecules can be used in viral gene delivery systems for gene therapy, e.g., adenoviral or retroviral gene delivery systems.

NBS-1 and PYRIN-1 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) *Nonviral Vectors for Gene Therapy*, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by bioballistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site. For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the Helios™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyethyleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) *BioTechniques* 28:304-315).

The host cells can also be used to produce nonhuman transgenic animals. For example, in one embodiment, a host cell of the invention is a fertilized oocyte or an embryonic stem cell into which NBS-1 or PYRIN-1-coding sequences have been introduced. Such host cells can then be used to create non-human transgenic animals in which exogenous NBS-1 or PYRIN-1 sequences have been introduced into their genome or homologous recombinant animals in which endogenous NBS-1 or PYRIN-1 sequences have been altered. Such animals are useful for studying the function and/or activity of NBS-1 or PYRIN-1 and for identifying and/or evaluating modulators of NBS-1 or PYRIN-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous NBS-1 or PYRIN-1 gene has been altered by homologous recombination between the endogenous gene and an exogenous DNA molecule introduced into a cell of the animal, e.g., an embryonic cell of the animal, prior to development of the animal.

A transgenic animal can created by introducing NBS-1 or PYRIN-1-encoding nucleic acid into the male pronuclei of a fertilized oocyte, e.g., by microinjection, retroviral infection, and allowing the oocyte to develop in a pseudopregnant female foster animal. Such transgenic animals are useful in screening assays and other methods of the invention.

The NBS-1 or PYRIN-1 cDNA sequence, e.g., that of SEQ ID NO:1, SEQ ID NO:3, SEQ ID NO:4, or SEQ ID NO:6, can be introduced as a transgene into the genome of a non-human animal. Alternatively, a nonhuman homolog or ortholog of the human NBS-1 or PYRIN-1 gene, such as a mouse NBS-1 or PYRIN-1 gene, can be isolated based on hybridization to the human NBS-1 or PYRIN-1 cDNA and used as a transgene. Intronic sequences and polyadenylation signals can also be included in the transgene to increase the efficiency of expression of the transgene. A tissue-specific regulatory sequence(s) can be operably linked to the NBS-1 or PYRIN-1 transgene to direct expression of NBS-1 or PYRIN-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the NBS-1 or PYRIN-1 transgene in its genome and/or expression of NBS-1 or PYRIN-1 mRNA in tissues or cells of the animals. A transgenic founder animal can then be used to breed additional animals carrying the transgene. Moreover, transgenic animals carrying a transgene encoding NBS-1 or PYRIN-1 can further be bred to other transgenic animals carrying other transgenes.

To create an homologous recombinant animal, a vector is prepared which contains at least a portion of a NBS-1 or PYRIN-1 gene (e.g., a human or a non-human homolog of the NBS-1 or PYRIN-1 gene, e.g., a murine NBS-1 or PYRIN-1 gene) into which a deletion, addition or substitution has been introduced to thereby alter, e.g., functionally disrupt, the NBS-1 or PYRIN-1 gene. In an embodiment, the vector is designed such that, upon homologous recombination, the endogenous NBS-1 or PYRIN-1 gene is functionally disrupted (i.e., no longer encodes a functional protein; also referred to as a "knock out" vector). Alternatively, the vector can be designed such that, upon homologous recombination, the endogenous NBS-1 or PYRIN-1 gene is mutated or otherwise altered but still encodes functional protein (e.g., the upstream regulatory region can be altered to thereby alter the expression of the endogenous NBS-1 or PYRIN-1 protein). In the homologous recombination vector, the altered portion of the NBS-1 or PYRIN-1 gene is flanked at its 5' and 3' ends by additional nucleic acid of the NBS-1 or PYRIN-1 gene to allow for homologous recombination to occur between the exogenous NBS-1 or PYRIN-1 gene carried by the vector and an endogenous NBS-1 or PYRIN-1 gene in an embryonic stem cell. The additional flanking NBS-1 or PYRIN-1 nucleic acid is of sufficient length for successful homologous recombination with the endogenous gene. Typically, several kilobases of flanking DNA (both at the 5' and 3' ends) are included in the vector (see, e.g., Thomas and Capecehi (1987) Cell 51:503 for a description of homologous recombination vectors). The vector is introduced into an embryonic stem cell line (e.g., by electroporation) and cells in which the introduced NBS-1 or PYRIN-1 gene has homologously recombined with the endogenous NBS-1 or PYRIN-1 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication Nos. WO 90/11354, WO 91/01140, WO 92/0968, and WO 93/04169.

Transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad Sci USA 89:6232-6236. Another example of a recombinase system is the FLP recombinase system of Saccharomyces cerevisiae (O'Gorman et al. (1991) Science 251:1351-1355. If a cre/loxP recombinase system is used to regulate expression of the transgene, animals containing transgenes .encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous NBS-1 or PYRIN-1 gene within a cell line or microorganism may be modified by inserting a heterologous DNA regulatory element into the genome of a stable cell line or cloned microorganism such that the inserted regulatory element is operatively linked with the endogenous NBS-1 or PYRIN-1 gene. For example, an endogenous NBS-1 or PYRIN-1 which is normally "transcriptionally silent," i.e. a NBS-1 or PYRIN-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous NBS-1 or PYRIN-1 gene may be activated by insertion of a promiscuous regulatory element that works across cell types.

A heterologous regulatory element may be inserted into a stable cell line or cloned microorganism, such that it is operatively linked with an endogenous NBS-1 or PYRIN-1 gene, using techniques, such as targeted homologous recombination, which are well known to those of skill in the art, and described e.g., in Chappel, U.S. Pat. No. 5,272,071; PCT publication No. WO 91/06667, publish,d May 16,1991.

V. Pharmaceutical Compositions

The NBS-1 or PYRIN-1 nucleic acid molecules, NBS-1 or PYRIN-1 proteins, and anti-NBS-1 or PYRIN-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NBS-1 or PYRIN-1 protein or anti-NBS-1 or PYRIN-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of protein, polypeptide, or antibody can include a single treatment or, preferably, can include a series of treatments.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) *Nonviral Vectors for Gene Therapy* (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) *BioTechniques* 28:304-315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound that binds to PYRIN-1, the method comprising the steps of:
   a) contacting a polypeptide or a cell from the group consisting of:
      i) a polypeptide comprising an amino acid sequence at least 95% identical to SEQ ID NO:5, wherein the polypeptide binds a nucleotide;
      ii) a polypeptide comprising a fragment of SEQ ID NO:5, wherein the fragment comprises the pyrin domain (amino acid residues 1-87 of SEQ ID NO:5) of PYRIN-1 and interacts with ASC;
      iii) a polypeptide comprising a fragment of SEQ ID NO:5, wherein the fragment comprises the NBS domain (amino acid residues 263-357 of SEQ ID NO:5) of PYRIN-1 and binds a nucleotide; and
      iv) a cell expressing the polypeptide of i), ii), or iii), with a test compound; and
   b) determining whether the polypeptide binds to the test compound.

2. The method of claim 1, wherein the binding of the test compound to the polypeptide is detected by a method selected from the group consisting of:
   a) detection of binding by direct detecting of test compound/polypeptide binding;
   b) detection of binding using a competition binding assay;
   c) detection of binding using an assay for PYRIN-1-mediated activation of NF-κB;
   d) detection of binding using an assay for caspase-1 proteolytic activity;
   e) detection of binding to a pyrin domain; and
   f) detection of binding to ASC.

3. A method for identifying a compound that inhibits the activity of PYRIN-1, the method comprising the steps of:
   a) contacting a polypeptide or a cell from the group consisting of:

i) a polypeptide comprising an amino acid sequence at least 95% identical to SEQ ID NO:5, wherein said polypeptide binds a nucleotide; and ii) a cell expressing the polypeptide of i), with a test compound; and b) determining the effect of the test compound on the activity of the polypeptide to thereby identify a compound that inhibits the: activity of the polypeptide.

4. A method for identifying a candidate compound for inhibiting the binding of PYRIN-1 to ASC, the method comprising:

a) measuring the binding of a first polypeptide comprising the pyrin domain of ASC (SEQ ID NO:8) to a second polypeptide comprising a fragment of SEQ ID NO:5, wherein the fragment comprises the pyrin domain (amino acid residues 1-87 of SEQ ID NO:5) of PYRIN-1 and interacts with ASC, in the presence of a test compound; and b) comparing the binding of the first polypeptide tote second polypeptide measured in step (a) to the binding of the first polypeptide to the second polypeptide in the absence of the test compound, wherein decreased binding of the first polypeptide to the second polypeptide in the presence of the test compound compared the binding in the absence of the test compound indicates that the test compound inhibits the binding of PYRIN-1 to ASC.

5. A method for identifying a candidate compound for inhibiting the ASC-mediated activation of NF-κB, the method comprising:

a) measuring the binding of a first polypeptide comprising the pyrin domain of ASC (SEQ ID NO:8) to a second polypeptide comprising a fragment of SEQ ID NO:5, wherein the fragment comprises the pyrin domain (amino acid residues 1-87 of SEQ ID NO:5) of PYRIN-1 and interacts with ASC, in the presence of a test compound; and b) comparing the binding of the first polypeptide to the second polypeptide measured in step (a) to the binding of the first polypeptide to the second polypeptide in the absence of the test compound, wherein decreased binding of the first polypeptide to the second polypeptide in the presence of the test compound compared the binding in the absence of the test compound indicates that the test compound is candidate compound for inhibiting the ASC-mediated activation of NF-κB.

6. A method for identifying an inhibitor of NF-κB activity, the method comprising:

a) providing a cell expressing recombinant ASC and recombinant PYRIN-1 (having an amino acid sequence at least 95% identical to SEQ ID NO:5), wherein said recombinant PYRIN-1 binds a nucleotide;

b) exposing the cell to a test compound; and c) measuring the NF-κB activity of the cell in the presence of the test compound wherein decreased activation in the presence of the test compound compared to the absence of the test compound indicates that the compound is an inhibitor of NF-κB activity.

7. A method for identifying a candidate inhibitor of PYRIN-1, the method comprising:

a) contacting a purified polypeptide comprising a polypeptide comprising a fragment of SEQ ID NO:5, wherein the fragment comprises the NIBS domain (amino acid residues 263-357 of SEQ ID NO:5) of PYRIN-1 and binds a nucleotide, with a test compound in the presence of a nucleotide that binds to the NBS domain in the absence of the test compound;

b) measuring the binding of the nucleotide to the NIBS domain in the presence of the test compound; and c) identifying the test compound as a candidate inhibitor of PYRIN-1 if the test compound reduces the binding of the nucleotide to the NIBS domain.

8. The method of claim 7, wherein the nucleotide is bound to the NBS domain before the polypeptide is exposed to the test compound.

9. The method of claim 7, wherein the test compound is exposed to the polypeptide before the polypeptide is exposed to the nucleotide.

10. The method of claim 7, wherein the nucleotide is selected from the group consisting of an adenine nucleotide, a guanidine nucleotide, a thymidine nucleotide, a cytosine nucleotide, and a uridine nucleotide.

11. The method of claim 7, wherein the nucleotide is selected from the group consisting of a ribonucleotide and a dideoxnbonucleotide.

12. The method of claim 7, wherein the nucleotide is selected from the group consisting of: ATP, ADP, TTP, TDP, UTP, UDP, CTP, CDP, GTP, and GDP.

13. A method for identifying a candidate compound for treating an inflammatory disorder, the method comprising:

a) measuring the binding of a first polypeptide comprising the pyrin domain of ASC (SEQ ID NO:8) to a second polypeptide comprising a fragment of SEQ ID NO:5, wherein the fragment comprises the pyrin domain (amino acid residues 1-87 of SEQ ID NO:5) of PYRIN-1, wherein said polypeptide interacts with ASC, in the presence of a test compound; and b) comparing the binding of the first polypeptide to the second polypeptide measured in step (a) to the binding of the first polypeptide to the second polypeptide in the absence of the test compound, wherein decreased binding of the first polypeptide to the second polypeptide in the presence of the test compound compared the binding in the absence of the test compound indicates that the test compound is a candidate compound for treating an inflammatory disorder.

14. A method for identifying a candidate compound for treating an inflammatory disorder, the method comprising:

a) measuring the binding of a first polypeptide comprising the pyrin domain of ASC (SEQ ID NO:8) to a second polypeptide comprising a fragment of SEQ ID NO:5, wherein the fragment comprises the pyrin domain (amino acid residues 1-87 of SEQ ID NO:5) of PYRIN-1, wherein said polypeptide interacts with ASC, in the presence of a test compound; and b) comparing the binding of the first polypeptide to the second polypeptide measured in step (a) to the binding of the first polypeptide to the second polypeptide in the absence of the test compound, wherein decreased binding of the first polypeptide to the second polypeptide in the presence of the test compound compared the binding in the absence of the test compound indicates that the test compound is candidate compound treating an inflammatory disorder.

15. A method for identifying a candidate compound for treating an inflammatory disorder, the method comprising:

a) providing a cell expressing recombinant ASC and recombinant PYRIN-1 (having an amino acid sequence at least 95% identical to SEQ ID NO:5), wherein said recombinant PYRIN-1 binds a nucleotide;

b) exposing the cell to a test compound; and c) measuring the NF-κB activity of the cell in the presence of the test compound wherein decreased activation in the presence of the test compound compared to the absence of the test compound indicates that the compound is a candidate compound for treating an inflammatory disorder.

16. A method for identifying an inhibitor of caspase-1 activity, the method comprising:
   a) providing a cell expressing recombinant PYRIN-1 (having an amino acid sequence at least 95% identical to SEQ ID NO:5), wherein said recombinant PYRIN-1 binds a nucleotide;
   b) exposing the cell to a test compound; and
   c) measuring caspase-1 activity of the cell in the presence of the test compound,
   wherein decreased caspase-1 activity in the presence of the test compound compared to the absence of the test compound indicates that the compound is an inhibitor of caspase-1 activity.

17. The method of claim 16, wherein the cell expresses recombinant ASC.

18. A method for identifying a candidate inhibitor of PYRIN-1, the method comprising:
   a) contacting a purified polypeptide comprising a fragment of SEQ ID NO:5, wherein the fragment comprises the pyrin domain (amino acid residues 1-87 of SEQ ID NO:5) of PYRIN-1, wherein said polypeptide interacts with ASC, with a test compound in the presence of caspase-1 and a caspase-1 substrate;
   b) measuring the proteolysis of the caspase-1 substrate in the presence of the test compound; and
   c) identifying the test compound as a candidate modulator of PYRIN-1 if the test compound inhibits the proteolysis of the caspase-1 substrate.

19. A method for identifying a compound that binds to PYRIN-1, the method comprising the steps of:
   a) contacting a polypeptide comprising the amino acid sequence of SEQ ID NO:5, or a cell expressing a polypeptide comprising the amino acid sequence of SEQ ID NO:5 with a test compound; and
   b) determining whether the polypeptide hinds to the test compound.

20. A method for identifying a compound that inhibits the activity of PYRIN-1, the method comprising the steps of:
   a) contacting a polypeptide comprising the amino acid sequence of SEQ ID NO:5, or a cell expressing a polypeptide comprising the amino acid sequence of SEQ ID NO:5 with a test compound; and
   b) determining the effect of the test compound on the activity of the polypeptide to thereby identify a compound that inhibits the activity of the polypeptide.

21. A method for identifying a compound that binds to PYRIN-1, the method comprising the steps of:
   a) contacting polypeptide comprising amino acid residues 219-434 of SEQ ID NO:5 of PYRIN-1, or a cell expressing a polypeptide comprising amino acid residues 219-434 of SEQ ID NO:5 of PYRIN-1 with a test compound; and
   b) determining whether the polypeptide binds to the test compound.

22. The method of claim 3, wherein the test compound is contacted with a polypeptide comprising amino acid residues 219-434 of SEQ ID NO:5 of PYRIN-1, or a cell expressing a polypeptide comprising amino acid residues 219-434 of SEQ ID NO:5 of PYRIN-1.

23. The method of claim 7, wherein the purified polypeptide comprises amino acid residues 219-434 of SEQ ID NO:5 of PYRIN-1.

24. The method of claim 6, wherein the cell expresses a polypeptide comprising the amino acid sequence of SEQ ID NO:5.

25. The method of claim 6, wherein the NF-κB activity is selected from the group consisting of: NF-κB nuclear localization, IκB phosphorylation and IκB proteolysis.

26. The method of claim 6, wherein the cell has a reporter gene under the control of a NF-κB regulatory element.

27. The method of claim 26, wherein the method further comprises the step of assaying the activity of the reporter gene.

28. The method of claim 1, wherein the polypeptide further comprises heterologous amino acid sequences.

29. The method of claim 3, wherein the polypeptide further comprises heterologous amino acid sequences.

30. The method of claim 1, wherein the polypeptide is immobilized.

31. The method of claim 1, wherein the test compound is labeled.

32. A method for identifying a compound that binds to PYRIN-1, the method comprising the steps of:
   a) contacting a polypeptide or a cell selected from the group consisting of:
      i) a polypeptide comprising an amino acid sequence at least 95% identical to SEQ ID NO:5, wherein the polypeptide binds a nucleotide; and
      ii) a cell expressing the polypeptide of i);
   with a test compound; and
   b) determining whether the polypeptide binds to the test compound.

33. A method for identifying a compound that binds to PYRIN-1, the method comprising the steps of:
   a) contacting a polypeptide or a cell selected from the group consisting of:
      i) a polypeptide comprising a fragment of SEQ ID NO:5, wherein the fragment comprises the pyrindomain (amino acid residues 1-87 of SEQ ID NO:5) of PYRIN-1 and interacts with ASC; and
      ii) a cell expressing the polypeptide of i);
   with a test compound; and
   b) determining whether the polypeptide binds to the test compound.

34. A method for identifying a compound that binds to PYRIN-1, the method comprising the steps of:
   a) contacting a polypeptide or a cell selected from the group consisting of:
      i) a polypeptide comprising a fragment of SEQ ID NO:5, wherein the fragment comprises the NBS domain (amino acid residues 263-357 of SEQ ID NO:5) of PYRIN-1 and binds a nucleotide; and
      ii) a cell expressing the polypeptide of i);
   with a test compound; and
   b) determining whether the polypeptide binds to the test compound.

* * * * *

SEQUENCE LISTING

<160> NUMBER OF SEQ ID NOS: 17

<210> SEQ ID NO 1
<211> LENGTH: 3431
<212> TYPE: DNA
<213> ORGANISM: Homo sapiens
<220> FEATURE:
<221> NAME/KEY: CDS
<222> LOCATION: (78)...(3176)

<400> SEQUENCE: 1

```
cagccctcat ctccgccggc gagtagggcc aggtgttggg agctcccacg tgggacaagg          60
tggtgtcttc ggcgcag atg ggt ttc aac ctg cag gct ctc ctg gag cag           110
                   Met Gly Phe Asn Leu Gln Ala Leu Leu Glu Gln
                    1               5                   10 ctc agc cag gat gag ttg agc aag ttc aag tat ctg atc acg acc ttc          158
Leu Ser Gln Asp Glu Leu Ser Lys Phe Lys Tyr Leu Ile Thr Thr Phe
             15                  20                  25 tcc ccg gca cac gag ctc cag aag atc ccc cac aag gag gta gac aag          206
Ser Pro Ala His Glu Leu Gln Lys Ile Pro His Lys Glu Val Asp Lys
         30                  35                  40 gct gat ggg aag caa ctg gta gaa atc ctc acc acc cat tgt gac agc          254
Ala Asp Gly Lys Gln Leu Val Glu Ile Leu Thr Thr His Cys Asp Ser
     45                  50                  55 tac tgg gtg gag atg gcg agc ctc cag gtc ttt gaa aag atg cac cga          302
Tyr Trp Val Glu Met Ala Ser Leu Gln Val Phe Glu Lys Met His Arg
 60                  65                  70                  75 atg gat ctg tct gag aga gca aag gat gaa gtc aga gaa gca gct ttg          350
Met Asp Leu Ser Glu Arg Ala Lys Asp Glu Val Arg Glu Ala Ala Leu
                 80                  85                  90 aaa tcc ttt aat aaa agg aag cct cta tca tta ggg ata aca cgg aaa          398
Lys Ser Phe Asn Lys Arg Lys Pro Leu Ser Leu Gly Ile Thr Arg Lys
             95                 100                 105 gaa cga cca cct cta gac gtg gac gaa atg ctg gag cgc ttc aaa aca          446
Glu Arg Pro Pro Leu Asp Val Asp Glu Met Leu Glu Arg Phe Lys Thr
        110                 115                 120 gaa gca caa gac aaa gac aat agg tgc agg tat ata ttg aag acg aag          494
Glu Ala Gln Asp Lys Asp Asn Arg Cys Arg Tyr Ile Leu Lys Thr Lys
    125                 130                 135 ttc cgg gag atg tgg aag agc tgg cct gga gat agc aaa gag gtc cag          542
Phe Arg Glu Met Trp Lys Ser Trp Pro Gly Asp Ser Lys Glu Val Gln
140                 145                 150                 155 gtt atg gct gag aga tac aag atg ctg atc cca ttt agc aac ccc agg          590
Val Met Ala Glu Arg Tyr Lys Met Leu Ile Pro Phe Ser Asn Pro Arg
                160                 165                 170 gtg ctt ccc ggg ccc ttc tca tac acg gtg gtg ctg tat ggt cct gca          638
Val Leu Pro Gly Pro Phe Ser Tyr Thr Val Val Leu Tyr Gly Pro Ala
            175                 180                 185 ggc ctt ggg aaa acc acg ctg gcc cag aaa cta atg cta gac tgg gca          686
Gly Leu Gly Lys Thr Thr Leu Ala Gln Lys Leu Met Leu Asp Trp Ala
        190                 195                 200 gag gac aac ctc atc cac aaa ttc aaa tat gcg ttc tac ctc agc tgc          734
Glu Asp Asn Leu Ile His Lys Phe Lys Tyr Ala Phe Tyr Leu Ser Cys
    205                 210                 215 agg gag ctc agc cgc ctg ggc ccg tgc agt ttt gca gag ctg gtc ttc          782
Arg Glu Leu Ser Arg Leu Gly Pro Cys Ser Phe Ala Glu Leu Val Phe
220                 225                 230                 235 agg gac tgg cct gaa ttg cag gat gac att cca cac atc cta gcc caa          830
Arg Asp Trp Pro Glu Leu Gln Asp Asp Ile Pro His Ile Leu Ala Gln
```

-continued

```
                       240                 245                 250
gca cgg aaa atc ttg ttc gtg att gac ggc ttt gat gag ctg gga gcc      878
Ala Arg Lys Ile Leu Phe Val Ile Asp Gly Phe Asp Glu Leu Gly Ala
            255                 260                 265 gca cct ggg gcg ctg atc gag gac atc tgc ggg gac tgg gag aag aag      926
Ala Pro Gly Ala Leu Ile Glu Asp Ile Cys Gly Asp Trp Glu Lys Lys
        270                 275                 280 aag ccg gtg ccc gtc ctc ctg ggg agt ttg ctg aac agg gtg atg tta      974
Lys Pro Val Pro Val Leu Leu Gly Ser Leu Leu Asn Arg Val Met Leu
    285                 290                 295 ccc aag gcc gcc ctg ctg gtc acc acg cgg ccc agg gcc ctg agg gac     1022
Pro Lys Ala Ala Leu Leu Val Thr Thr Arg Pro Arg Ala Leu Arg Asp
300                 305                 310                 315 ctc cgg atc ctg gcg gag gag ccg atc tac ata agg gtg gag ggc ttc     1070
Leu Arg Ile Leu Ala Glu Glu Pro Ile Tyr Ile Arg Val Glu Gly Phe
                320                 325                 330 ctg gag gag gac aag agg gcc tat ttc ctg aga cac ttt gga gac gag     1118
Leu Glu Glu Asp Lys Arg Ala Tyr Phe Leu Arg His Phe Gly Asp Glu
            335                 340                 345 gac caa gcc atg cgt gcc ttt gag cta atg agg agc aac gcg gcc ctg     1166
Asp Gln Ala Met Arg Ala Phe Glu Leu Met Arg Ser Asn Ala Ala Leu
        350                 355                 360 ttc cag ctg ggc tcg gcc ccc gcg gtg tgc tgg atc gtg tgc acg act     1214
Phe Gln Leu Gly Ser Ala Pro Ala Val Cys Trp Ile Val Cys Thr Thr
    365                 370                 375 ctg aag ctg cag atg gag aag ggg gag gac ccg gtc ccc acc tgc ctc     1262
Leu Lys Leu Gln Met Glu Lys Gly Glu Asp Pro Val Pro Thr Cys Leu
380                 385                 390                 395 acc cgc acg ggg ctg ttc ctg cgt ttc ctc tgc agc cgg ttc ccg cag     1310
Thr Arg Thr Gly Leu Phe Leu Arg Phe Leu Cys Ser Arg Phe Pro Gln
                400                 405                 410 ggc gca cag ctg cgg ggc gcg ctg cgg acg ctg agc ctc ctg gcc gcg     1358
Gly Ala Gln Leu Arg Gly Ala Leu Arg Thr Leu Ser Leu Leu Ala Ala
            415                 420                 425 cag ggc ctg tgg gcg cag acg tcc gtg ctt cac cga gag gat ctg gaa     1406
Gln Gly Leu Trp Ala Gln Thr Ser Val Leu His Arg Glu Asp Leu Glu
        430                 435                 440 agg ctc ggg gtg cag gag tcc gac ctc cgt ctg ttc ctg gac gga gac     1454
Arg Leu Gly Val Gln Glu Ser Asp Leu Arg Leu Phe Leu Asp Gly Asp
    445                 450                 455 atc ctc cgc cag gac aga gtc tcc aaa ggc tgc tac tcc ttc atc cac     1502
Ile Leu Arg Gln Asp Arg Val Ser Lys Gly Cys Tyr Ser Phe Ile His
460                 465                 470                 475 ctc agc ttc cag cag ttt ctc act gcc ctg ttc tac acc ctg gag aag     1550
Leu Ser Phe Gln Gln Phe Leu Thr Ala Leu Phe Tyr Thr Leu Glu Lys
                480                 485                 490 gag gag gaa gag gat agg gac ggc cac acc tgg gac att ggg gac gta     1598
Glu Glu Glu Glu Asp Arg Asp Gly His Thr Trp Asp Ile Gly Asp Val
            495                 500                 505 cag aag ctg ctt tcc gga gta gaa aga ctc agg aac ccc gac ctg atc     1646
Gln Lys Leu Leu Ser Gly Val Glu Arg Leu Arg Asn Pro Asp Leu Ile
        510                 515                 520 caa gca ggc tac tac tcc ttt ggc ctc gct aac gag aag aga gcc aag     1694
Gln Ala Gly Tyr Tyr Ser Phe Gly Leu Ala Asn Glu Lys Arg Ala Lys
    525                 530                 535 gag ttg gag gcc act ttt ggc tgc cgg atg tca ccg gac atc aaa cag     1742
Glu Leu Glu Ala Thr Phe Gly Cys Arg Met Ser Pro Asp Ile Lys Gln
540                 545                 550                 555 gaa ttg ctg cga tgc gac ata agt tgt aag ggt gga cat tca acg gtg     1790
```

```
Glu Leu Leu Arg Cys Asp Ile Ser Cys Lys Gly Gly His Ser Thr Val
            560                 565                 570 aca gac ctg cag gag ctc ctc ggc tgt ctg tac gag tct cag gag gag     1838
Thr Asp Leu Gln Glu Leu Leu Gly Cys Leu Tyr Glu Ser Gln Glu Glu
        575                 580                 585 gag ctg gtg aag gag gtg atg gct cag ttc aaa gaa ata tcc ctg cac     1886
Glu Leu Val Lys Glu Val Met Ala Gln Phe Lys Glu Ile Ser Leu His
        590                 595                 600 tta aat gca gta gac gtt gtg cca tct tca ttc tgc gtc aag cac tgt     1934
Leu Asn Ala Val Asp Val Val Pro Ser Ser Phe Cys Val Lys His Cys
    605                 610                 615 cga aac ctg cag aaa atg tca ctg cag gta ata aag gag aat ctc ccg     1982
Arg Asn Leu Gln Lys Met Ser Leu Gln Val Ile Lys Glu Asn Leu Pro
620                 625                 630                 635 gag aat gtc act gcg tct gaa tca gac gcc gag gtt gag aga tcc cag     2030
Glu Asn Val Thr Ala Ser Glu Ser Asp Ala Glu Val Glu Arg Ser Gln
            640                 645                 650 gat gat cag cac atg ctt cct ttc tgg acg gac ctt tgt tcc ata ttt     2078
Asp Asp Gln His Met Leu Pro Phe Trp Thr Asp Leu Cys Ser Ile Phe
        655                 660                 665 gga tca aat aag gat ctg atg ggt cta gca atc aat gat agc ttt ctc     2126
Gly Ser Asn Lys Asp Leu Met Gly Leu Ala Ile Asn Asp Ser Phe Leu
        670                 675                 680 agt gcc tcc cta gta agg atc ctg tgt gaa caa ata gcc tct gac acc     2174
Ser Ala Ser Leu Val Arg Ile Leu Cys Glu Gln Ile Ala Ser Asp Thr
    685                 690                 695 tgt cat ctc cag aga gtg gtg ttc aaa aac att tcc cca gct gat gct     2222
Cys His Leu Gln Arg Val Val Phe Lys Asn Ile Ser Pro Ala Asp Ala
700                 705                 710                 715 cat cgg aac ctc tgc cta gct ctt cga ggt cac aag act gta acg tat     2270
His Arg Asn Leu Cys Leu Ala Leu Arg Gly His Lys Thr Val Thr Tyr
            720                 725                 730 ctg acc ctt caa ggc aat gac cag gat gat atg ttt ccc gca ttg tgt     2318
Leu Thr Leu Gln Gly Asn Asp Gln Asp Asp Met Phe Pro Ala Leu Cys
        735                 740                 745 gag gtc ttg aga cat cca gaa tgt aac ctg cga tat ctc ggg ttg gtg     2366
Glu Val Leu Arg His Pro Glu Cys Asn Leu Arg Tyr Leu Gly Leu Val
        750                 755                 760 tct tgt tcc gct acc act cag cag tgg gct gat ctc tcc ttg gcc ctt     2414
Ser Cys Ser Ala Thr Thr Gln Gln Trp Ala Asp Leu Ser Leu Ala Leu
    765                 770                 775 gaa gtc aac cag tcc ctg acg tgc gta aac ctc tcc gac aat gag ctt     2462
Glu Val Asn Gln Ser Leu Thr Cys Val Asn Leu Ser Asp Asn Glu Leu
780                 785                 790                 795 ctg gat gag ggt gct aag ttg cta tac aca act ttg aga cac ccc aag     2510
Leu Asp Glu Gly Ala Lys Leu Leu Tyr Thr Thr Leu Arg His Pro Lys
            800                 805                 810 tgc ttt ctg cag agg ttg tcg ttg gaa aac tgt cac ctt aca gaa gcc     2558
Cys Phe Leu Gln Arg Leu Ser Leu Glu Asn Cys His Leu Thr Glu Ala
        815                 820                 825 aat tgc aag gac ctt gct gct gtg ttg gtt gtc agc cgg gag ctg aca     2606
Asn Cys Lys Asp Leu Ala Ala Val Leu Val Val Ser Arg Glu Leu Thr
        830                 835                 840 cac ctg tgc ttg gcc aag aac ccc att ggg aat aca ggg gtg aag ttt     2654
His Leu Cys Leu Ala Lys Asn Pro Ile Gly Asn Thr Gly Val Lys Phe
    845                 850                 855 ctg tgt gag ggc ttg agg tac ccc gag tgt aaa ctg cag acc ttg gtg     2702
Leu Cys Glu Gly Leu Arg Tyr Pro Glu Cys Lys Leu Gln Thr Leu Val
860                 865                 870                 875
```

```
ctt tgg aac tgc gac ata act agc gat ggc tgc tgc gat ctc aca aag         2750
Leu Trp Asn Cys Asp Ile Thr Ser Asp Gly Cys Cys Asp Leu Thr Lys
            880                 885                 890 ctt ctc caa gaa aaa tca agc ctg ttg tgt ttg gat ctg ggg ctg aat         2798
Leu Leu Gln Glu Lys Ser Ser Leu Leu Cys Leu Asp Leu Gly Leu Asn
        895                 900                 905 cac ata gga gtt aag gga atg aag ttc ctg tgt gag gct ttg agg aaa         2846
His Ile Gly Val Lys Gly Met Lys Phe Leu Cys Glu Ala Leu Arg Lys
    910                 915                 920 cca ctg tgc aac ttg aga tgt ctg tgg ttg tgg gga tgt tcc atc cct         2894
Pro Leu Cys Asn Leu Arg Cys Leu Trp Leu Trp Gly Cys Ser Ile Pro
925                 930                 935 ccg ttc agt tgt gaa gac ctc tgc tct gcc ctc agc aac cag agc ctc         2942
Pro Phe Ser Cys Glu Asp Leu Cys Ser Ala Leu Ser Asn Gln Ser Leu
940                 945                 950                 955 gtc act ctg gac ctg ggt cag aat ccc ttg ggg tct agt gga gtg aag         2990
Val Thr Leu Asp Leu Gly Gln Asn Pro Leu Gly Ser Ser Gly Val Lys
            960                 965                 970 atg ctg ttt gaa acc ttg aca tgt tcc agt ggc acc ctc cgg aca ctc         3038
Met Leu Phe Glu Thr Leu Thr Cys Ser Ser Gly Thr Leu Arg Thr Leu
        975                 980                 985 agg ttg aaa atc gat gac ttt aat gat gaa ctc aat aag ctg ctg gaa         3086
Arg Leu Lys Ile Asp Asp Phe Asn Asp Glu Leu Asn Lys Leu Leu Glu
    990                 995                 1000 gaa ata gaa gaa aaa aac cca caa ctg att att gat act gag aaa cat         3134
Glu Ile Glu Glu Lys Asn Pro Gln Leu Ile Ile Asp Thr Glu Lys His
1005                1010                1015 cat ccc tgg gca gaa agg cct tct tct cat gac ttc atg atc                 3176
His Pro Trp Ala Glu Arg Pro Ser Ser His Asp Phe Met Ile
1020                1025                1030 tgaatccccc cgagtcattc attctccatg aagtcatcga ttttccaggt gttggtgaac       3236
tgcctgtgac tcctctcctc cccggcccct acccctcagg gataatgagt tcattgctgg       3296
gctagatgtt ttagccatga ttctgcctct gttttatacc tgcacacatc cttatctttg       3356
ttacatatga aatatctgta tcacgggtat attgagagaa ataaaggtga gagcattcac       3416
aaaaaaaaaa aaaaa                                                         3431

<210> SEQ ID NO 2
<211> LENGTH: 1033
<212> TYPE: PRT
<213> ORGANISM: Homo sapiens

<400> SEQUENCE: 2

Met Gly Phe Asn Leu Gln Ala Leu Leu Glu Gln Leu Ser Gln Asp Glu
1               5                   10                  15

Leu Ser Lys Phe Lys Tyr Leu Ile Thr Thr Phe Ser Pro Ala His Glu
            20                  25                  30

Leu Gln Lys Ile Pro His Lys Glu Val Asp Lys Ala Asp Gly Lys Gln
        35                  40                  45

Leu Val Glu Ile Leu Thr Thr His Cys Asp Ser Tyr Trp Val Glu Met
    50                  55                  60

Ala Ser Leu Gln Val Phe Glu Lys Met His Arg Met Asp Leu Ser Glu
65                  70                  75                  80

Arg Ala Lys Asp Glu Val Arg Glu Ala Leu Lys Ser Phe Asn Lys
                85                  90                  95

Arg Lys Pro Leu Ser Leu Gly Ile Thr Arg Lys Glu Arg Pro Pro Leu
            100                 105                 110
```

```
Asp Val Asp Glu Met Leu Glu Arg Phe Lys Thr Glu Ala Gln Asp Lys
        115                 120                 125

Asp Asn Arg Cys Arg Tyr Ile Leu Lys Thr Lys Phe Arg Glu Met Trp
    130                 135                 140

Lys Ser Trp Pro Gly Asp Ser Lys Glu Val Gln Val Met Ala Glu Arg
145                 150                 155                 160

Tyr Lys Met Leu Ile Pro Phe Ser Asn Pro Arg Val Leu Pro Gly Pro
                165                 170                 175

Phe Ser Tyr Thr Val Leu Tyr Gly Pro Ala Gly Leu Gly Lys Thr
            180                 185                 190

Thr Leu Ala Gln Lys Leu Met Leu Asp Trp Ala Glu Asp Asn Leu Ile
        195                 200                 205

His Lys Phe Lys Tyr Ala Phe Tyr Leu Ser Cys Arg Glu Leu Ser Arg
    210                 215                 220

Leu Gly Pro Cys Ser Phe Ala Glu Leu Val Phe Arg Asp Trp Pro Glu
225                 230                 235                 240

Leu Gln Asp Asp Ile Pro His Ile Leu Ala Gln Ala Arg Lys Ile Leu
                245                 250                 255

Phe Val Ile Asp Gly Phe Asp Glu Leu Gly Ala Ala Pro Gly Ala Leu
                260                 265                 270

Ile Glu Asp Ile Cys Gly Asp Trp Glu Lys Lys Pro Val Pro Val
        275                 280                 285

Leu Leu Gly Ser Leu Leu Asn Arg Val Met Leu Pro Lys Ala Ala Leu
        290                 295                 300

Leu Val Thr Thr Arg Pro Arg Ala Leu Arg Asp Leu Arg Ile Leu Ala
305                 310                 315                 320

Glu Glu Pro Ile Tyr Ile Arg Val Glu Gly Phe Leu Glu Glu Asp Lys
                325                 330                 335

Arg Ala Tyr Phe Leu Arg His Phe Gly Asp Glu Asp Gln Ala Met Arg
                340                 345                 350

Ala Phe Glu Leu Met Arg Ser Asn Ala Ala Leu Phe Gln Leu Gly Ser
        355                 360                 365

Ala Pro Ala Val Cys Trp Ile Val Cys Thr Thr Leu Lys Leu Gln Met
        370                 375                 380

Glu Lys Gly Glu Asp Pro Val Pro Thr Cys Leu Thr Arg Thr Gly Leu
385                 390                 395                 400

Phe Leu Arg Phe Leu Cys Ser Arg Phe Pro Gln Gly Ala Gln Leu Arg
                405                 410                 415

Gly Ala Leu Arg Thr Leu Ser Leu Leu Ala Ala Gln Gly Leu Trp Ala
                420                 425                 430

Gln Thr Ser Val Leu His Arg Glu Asp Leu Glu Arg Leu Gly Val Gln
        435                 440                 445

Glu Ser Asp Leu Arg Leu Phe Leu Asp Gly Asp Ile Leu Arg Gln Asp
        450                 455                 460

Arg Val Ser Lys Gly Cys Tyr Ser Phe Ile His Leu Ser Phe Gln Gln
465                 470                 475                 480

Phe Leu Thr Ala Leu Phe Tyr Thr Leu Glu Lys Glu Glu Glu Asp
                485                 490                 495

Arg Asp Gly His Thr Trp Asp Ile Gly Asp Val Gln Lys Leu Leu Ser
            500                 505                 510

Gly Val Glu Arg Leu Arg Asn Pro Asp Leu Ile Gln Ala Gly Tyr Tyr
        515                 520                 525

Ser Phe Gly Leu Ala Asn Glu Lys Arg Ala Lys Glu Leu Glu Ala Thr
```

-continued

```
            530                 535                 540
Phe Gly Cys Arg Met Ser Pro Asp Ile Lys Gln Glu Leu Leu Arg Cys
545                 550                 555                 560

Asp Ile Ser Cys Lys Gly Gly His Ser Thr Val Thr Asp Leu Gln Glu
                565                 570                 575

Leu Leu Gly Cys Leu Tyr Glu Ser Gln Glu Glu Leu Val Lys Glu
                580                 585                 590

Val Met Ala Gln Phe Lys Glu Ile Ser Leu His Leu Asn Ala Val Asp
            595                 600                 605

Val Val Pro Ser Ser Phe Cys Val Lys His Cys Arg Asn Leu Gln Lys
610                 615                 620

Met Ser Leu Gln Val Ile Lys Glu Asn Leu Pro Glu Asn Val Thr Ala
625                 630                 635                 640

Ser Glu Ser Asp Ala Glu Val Glu Arg Ser Gln Asp Gln His Met
                645                 650                 655

Leu Pro Phe Trp Thr Asp Leu Cys Ser Ile Phe Gly Ser Asn Lys Asp
                660                 665                 670

Leu Met Gly Leu Ala Ile Asn Asp Ser Phe Leu Ser Ala Ser Leu Val
                675                 680                 685

Arg Ile Leu Cys Glu Gln Ile Ala Ser Asp Thr Cys His Leu Gln Arg
            690                 695                 700

Val Val Phe Lys Asn Ile Ser Pro Ala Asp Ala His Arg Asn Leu Cys
705                 710                 715                 720

Leu Ala Leu Arg Gly His Lys Thr Val Thr Tyr Leu Thr Leu Gln Gly
                725                 730                 735

Asn Asp Gln Asp Asp Met Phe Pro Ala Leu Cys Glu Val Leu Arg His
            740                 745                 750

Pro Glu Cys Asn Leu Arg Tyr Leu Gly Leu Val Ser Cys Ser Ala Thr
            755                 760                 765

Thr Gln Gln Trp Ala Asp Leu Ser Leu Ala Leu Glu Val Asn Gln Ser
            770                 775                 780

Leu Thr Cys Val Asn Leu Ser Asp Asn Glu Leu Leu Asp Glu Gly Ala
785                 790                 795                 800

Lys Leu Leu Tyr Thr Thr Leu Arg His Pro Lys Cys Phe Leu Gln Arg
                805                 810                 815

Leu Ser Leu Glu Asn Cys His Leu Thr Glu Ala Asn Cys Lys Asp Leu
                820                 825                 830

Ala Ala Val Leu Val Ser Arg Glu Leu Thr His Leu Cys Leu Ala
            835                 840                 845

Lys Asn Pro Ile Gly Asn Thr Gly Val Lys Phe Leu Cys Glu Gly Leu
850                 855                 860

Arg Tyr Pro Glu Cys Lys Leu Gln Thr Leu Val Leu Trp Asn Cys Asp
865                 870                 875                 880

Ile Thr Ser Asp Gly Cys Cys Asp Leu Thr Lys Leu Leu Gln Glu Lys
                885                 890                 895

Ser Ser Leu Leu Cys Leu Asp Leu Gly Leu Asn His Ile Gly Val Lys
                900                 905                 910

Gly Met Lys Phe Leu Cys Glu Ala Leu Arg Lys Pro Leu Cys Asn Leu
                915                 920                 925

Arg Cys Leu Trp Leu Trp Gly Cys Ser Ile Pro Pro Phe Ser Cys Glu
            930                 935                 940

Asp Leu Cys Ser Ala Leu Ser Asn Gln Ser Leu Val Thr Leu Asp Leu
945                 950                 955                 960
```

-continued

Gly Gln Asn Pro Leu Gly Ser Ser Gly Val Lys Met Leu Phe Glu Thr
                965                 970                 975

Leu Thr Cys Ser Ser Gly Thr Leu Arg Thr Leu Arg Leu Lys Ile Asp
            980                 985                 990

Asp Phe Asn Asp Glu Leu Asn Lys Leu Leu Glu Glu Ile Glu Glu Lys
        995                 1000                1005

Asn Pro Gln Leu Ile Ile Asp Thr Glu Lys His His Pro Trp Ala Glu
    1010                1015                1020

Arg Pro Ser Ser His Asp Phe Met Ile
1025                1030

<210> SEQ ID NO 3
<211> LENGTH: 3099
<212> TYPE: DNA
<213> ORGANISM: Homo sapiens

<400> SEQUENCE: 3

| | | | | | |
|---|---|---|---|---|---|
| atgggtttca | acctgcaggc | tctcctggag | cagctcagcc | aggatgagtt | gagcaagttc | 60 |
| aagtatctga | tcacgacctt | ctccccggca | cacgagctcc | agaagatccc | ccacaaggag | 120 |
| gtagacaagg | ctgatgggaa | gcaactggta | gaaatcctca | ccacccattg | tgacagctac | 180 |
| tgggtgagag | tggcgagcct | ccaggtcttt | gaaaagatgc | accgaatgga | tctgtctgag | 240 |
| agagcaaagg | atgaagtcag | agaagcagct | ttgaaatcct | taataaaag | gaagcctcta | 300 |
| tcattaggga | taacacggaa | agaacgacca | cctctagacg | tggacgaaat | gctggagcgc | 360 |
| ttcaaaacag | aagcacaaga | caaagacaat | aggtgcaggt | atatattgaa | gacgaagttc | 420 |
| cgggagatgt | ggaagagctg | gcctggagat | agcaaagagg | tccaggttat | ggctgagaga | 480 |
| tacaagatgc | tgatcccatt | tagcaacccc | agggtgcttc | ccgggccctt | ctcatacacg | 540 |
| gtggtgctgt | atggtcctgc | aggccttggg | aaaaccacgc | tggcccagaa | actaatgcta | 600 |
| gactgggcag | aggacaacct | catccacaaa | ttcaaatatg | cgttctacct | cagctgcagg | 660 |
| gagctcagcc | gcctgggccc | gtgcagtttt | gcagagctgg | tcttcaggga | ctggcctgaa | 720 |
| ttgcaggatg | acattccaca | catcctagcc | caagcacgga | aaatcttgtt | cgtgattgac | 780 |
| ggctttgatg | agctgggagc | cgcacctggg | gcgctgatcg | aggacatctg | cggggactgg | 840 |
| gagaagaaga | agccggtgcc | cgtcctcctg | gggagtttgc | tgaacagggt | gatgttaccc | 900 |
| aaggccgccc | tgctggtcac | cacgcggccc | agggccctga | ggaccctccg | gatcctggcg | 960 |
| gaggagccga | tctacataag | ggtggagggc | ttcctggagg | aggacaagag | ggcctatttc | 1020 |
| ctgagacact | ttggagacga | ggaccaagcc | atgcgtgcct | ttgagctaat | gaggagcaac | 1080 |
| gcggccctgt | tccagctggg | ctcggccccc | gcggtgtgct | ggatcgtgtg | cacgactctg | 1140 |
| aagctgcaga | tggagaaggg | ggaggacccg | gtccccacct | gcctcacccg | cacggggctg | 1200 |
| ttcctgcgtt | tcctctgcag | ccggttcccg | cagggcgcac | agctgcgggg | cgcgctgcgg | 1260 |
| acgctgagcc | tcctggccgc | gcagggcctg | tgggcgcaga | cgtccgtgct | tcaccgagag | 1320 |
| gatctggaaa | ggctcgggt | gcaggagtcc | gacctccgtc | tgttcctgga | cggagacatc | 1380 |
| ctccgccagg | acagagtctc | caaaggctgc | tactccttca | tccacctcag | cttccagcag | 1440 |
| tttctcactg | ccctgttcta | caccctggag | aaggaggagg | aagaggatag | ggacggccac | 1500 |
| acctgggaca | ttggggacgt | acagaagctg | ctttccggag | tagaaagact | caggaacccc | 1560 |
| gacctgatcc | aagcaggcta | ctactccttt | ggcctcgcta | acgagaagag | agccaaggag | 1620 |
| ttggaggcca | cttttggctg | ccggatgtca | ccggacatca | acaggaatt | gctgcgatgc | 1680 |

```
gacataagtt gtaagggtgg acattcaacg gtgacagacc tgcaggagct cctcggctgt    1740
ctgtacgagt ctcaggagga ggagctggtg aaggaggtga tggctcagtt caaagaaata    1800
tccctgcact taaatgcagt agacgttgtg ccatcttcat tctgcgtcaa gcactgtcga    1860
aacctgcaga aaatgtcact gcaggtaata aaggagaatc tcccggagaa tgtcactgcg    1920
tctgaatcag acgccgaggt tgagagatcc caggatgatc agcacatgct tcctttctgg    1980
acggaccttt gttccatatt tggatcaaat aaggatctga tgggtctagc aatcaatgat    2040
agctttctca gtgcctccct agtaaggatc ctgtgtgaac aaatagcctc tgacacctgt    2100
catctccaga gagtggtgtt caaaaacatt tccccagctg atgctcatcg aacctctgc     2160 ctagctcttc gaggtcacaa gactgtaacg tatctgaccc ttcaaggcaa tgaccaggat    2220
gatatgtttc ccgcattgtg tgaggtcttg agacatccag aatgtaacct gcgatatctc    2280
gggttggtgt cttgttccgc taccactcag cagtgggctg atctctcctt ggcccttgaa    2340
gtcaaccagt ccctgacgtg cgtaaacctc tccgacaatg agcttctgga tgagggtgct    2400
aagttgctgt acacaacttt gagacacccc aagtgctttc tgcagaggtt gtcgttggaa    2460
aactgtcacc ttacagaagc caattgcaag gaccttgctg ctgtgttggt tgtcagccgg    2520
gagctgacac acctgtgctt ggccaagaac cccattggga atacaggggt gaagtttctg    2580
tgtgagggct tgaggtaccc cgagtgtaaa ctgcagacct tggtgctttg gaactgcgac    2640
ataactagcg atggctgctg cgatctcaca aagcttctcc aagaaaaatc aagcctgttg    2700
tgtttggatc tggggctgaa tcacatagga gttaagggaa tgaagttcct gtgtgaggct    2760
ttgaggaaac cactgtgcaa cttgagatgt ctgtggttgt ggggatgttc catccctccg    2820
ttcagttgtg aagacctctg ctctgccctc agcaaccaga gcctcgtcac tctggacctg    2880
ggtcagaatc ccttggggtc tagtggagtg aagatgctgt ttgaaacctt gacatgttcc    2940
agtggcaccc tccggacact caggttgaaa atcgatgact ttaatgatga actcaataag    3000
ctgctggaag aaatagaaga aaaaaaccca caactgatta ttgatactga gaaacatcat    3060
ccctgggcag aaaggccttc ttctcatgac ttcatgatc                          3099
```

<210> SEQ ID NO 4
<211> LENGTH: 3857
<212> TYPE: DNA
<213> ORGANISM: Homo sapiens
<220> FEATURE:
<221> NAME/KEY: CDS
<222> LOCATION: (139)...(3240)

<400> SEQUENCE: 4

```
ccacgcgtcc gcccacgcgt ccgggcatct ggggaaacct ttcttccatg gctcaggaca     60
cactcctgga tcgagccaac aggagaactt tctgtgtgga ccgaagccta aggaccctga    120
aaacagctgc agatgaag atg gca agc acc cgc tgc aag ctg gcc agg tac      171
                    Met Ala Ser Thr Arg Cys Lys Leu Ala Arg Tyr
                     1               5                  10 ctg gag gac ctg gag gat gtg gac ttg aag aaa ttt aag atg cac tta     219
Leu Glu Asp Leu Glu Asp Val Asp Leu Lys Lys Phe Lys Met His Leu
            15                  20                  25 gag gac tat cct ccc cag aag ggc tgc atc ccc ctc ccg agg ggt cag     267
Glu Asp Tyr Pro Pro Gln Lys Gly Cys Ile Pro Leu Pro Arg Gly Gln
        30                  35                  40 aca gag aag gca gac cat gtg gat cta gcc acg cta atg atc gac ttc    315
Thr Glu Lys Ala Asp His Val Asp Leu Ala Thr Leu Met Ile Asp Phe
    45                  50                  55
```

-continued

| | |
|---|---|
| aat ggg gag gag aag gcg tgg gcc atg gcc gtg tgg atc ttc gct gcg<br>Asn Gly Glu Glu Lys Ala Trp Ala Met Ala Val Trp Ile Phe Ala Ala<br>60                        65                   70                   75 | 363 |
| atc aac agg aga gac ctt tat gag aaa gca aaa aga gat gag ccg aag<br>Ile Asn Arg Arg Asp Leu Tyr Glu Lys Ala Lys Arg Asp Glu Pro Lys<br>                80                   85                   90 | 411 |
| tgg ggt tca gat aat gca cgt gtt tcg aat ccc act gtg ata tgc cag<br>Trp Gly Ser Asp Asn Ala Arg Val Ser Asn Pro Thr Val Ile Cys Gln<br>             95                   100                 105 | 459 |
| gaa gac agc att gaa gag gag tgg atg ggt tta ctg gag tac ctt tcg<br>Glu Asp Ser Ile Glu Glu Glu Trp Met Gly Leu Leu Glu Tyr Leu Ser<br>110                   115                 120 | 507 |
| aga atc tct att tgt aaa atg aag aaa gat tac cgt aag aag tac aga<br>Arg Ile Ser Ile Cys Lys Met Lys Lys Asp Tyr Arg Lys Lys Tyr Arg<br>           125                 130                135 | 555 |
| aag tac gtg aga agc aga ttc cag tgc att gaa gac agg aat gcc cgt<br>Lys Tyr Val Arg Ser Arg Phe Gln Cys Ile Glu Asp Arg Asn Ala Arg<br>140                   145                 150                155 | 603 |
| ctg ggt gag agt gtg agc ctc aac aaa cgc tac aca cga ctg cgt ctc<br>Leu Gly Glu Ser Val Ser Leu Asn Lys Arg Tyr Thr Arg Leu Arg Leu<br>                   160                 165              170 | 651 |
| atc aag gag cac cgg agc cag cag gag agg gag cag gag ctt ctg gcc<br>Ile Lys Glu His Arg Ser Gln Gln Glu Arg Glu Gln Glu Leu Leu Ala<br>               175                 180                185 | 699 |
| atc ggc aag acc aag acg tgt gag agc ccc gtg agt ccc att aag atg<br>Ile Gly Lys Thr Lys Thr Cys Glu Ser Pro Val Ser Pro Ile Lys Met<br>                   190                 195               200 | 747 |
| gag ttg ctg ttt gac ccc gat gat gag cat tct gag cct gtg cac acc<br>Glu Leu Leu Phe Asp Pro Asp Asp Glu His Ser Glu Pro Val His Thr<br>205                   210                 215 | 795 |
| gtg gtg ttc cag ggg gcg gca ggg att ggg aaa aca atc ctg gcc agg<br>Val Val Phe Gln Gly Ala Ala Gly Ile Gly Lys Thr Ile Leu Ala Arg<br>220                   225                 230                235 | 843 |
| aag atg atg ttg gac tgg gca tcg ggg aca ctc tac caa gac agg ttt<br>Lys Met Met Leu Asp Trp Ala Ser Gly Thr Leu Tyr Gln Asp Arg Phe<br>                 240                 245               250 | 891 |
| gac tat ctg ttc tat atc cac tgt cgg gag gtg agc ctt gtg aca cag<br>Asp Tyr Leu Phe Tyr Ile His Cys Arg Glu Val Ser Leu Val Thr Gln<br>               255                 260                265 | 939 |
| agg agc ctg ggg gac ctg atc atg agc tgc tgc ccc gac cca aac cca<br>Arg Ser Leu Gly Asp Leu Ile Met Ser Cys Cys Pro Asp Pro Asn Pro<br>           270                 275                280 | 987 |
| ccc atc cac aag atc gtg aga aaa ccc tcc aga atc ctc ttc ctc atg<br>Pro Ile His Lys Ile Val Arg Lys Pro Ser Arg Ile Leu Phe Leu Met<br>285                   290                 295 | 1035 |
| gac ggc ttc gat gag ctg caa ggt gcc ttt gac gag cac ata gga ccg<br>Asp Gly Phe Asp Glu Leu Gln Gly Ala Phe Asp Glu His Ile Gly Pro<br>300                   305                 310                315 | 1083 |
| ctc tgc act gac tgg cag aag gcc gag cgg gga gac att ctc ctg agc<br>Leu Cys Thr Asp Trp Gln Lys Ala Glu Arg Gly Asp Ile Leu Leu Ser<br>                 320                 325               330 | 1131 |
| agc ctc atc aga aag aag ctg ctt ccc gag gcc tct ctc ctc atc acc<br>Ser Leu Ile Arg Lys Lys Leu Leu Pro Glu Ala Ser Leu Leu Ile Thr<br>           335                 340                345 | 1179 |
| acg aga cct gtg gcc ctg gag aaa ctg cag cac ttg ctg gac cat cct<br>Thr Arg Pro Val Ala Leu Glu Lys Leu Gln His Leu Leu Asp His Pro<br>350                   355                 360 | 1227 |
| cgg cat gtg gag atc ctg ggt ttc tcc gag gcc aaa agg aaa gag tac<br>Arg His Val Glu Ile Leu Gly Phe Ser Glu Ala Lys Arg Lys Glu Tyr | 1275 |

|  |  |  |  |  |  |  |  |  |  |  |  |  |  |  |  |
|---|---|---|---|---|---|---|---|---|---|---|---|---|---|---|---|

```
                    365                 370                 375
ttc ttc aag tac ttc tct gat gag gcc caa gcc agg gca gcc ttc agt       1323
Phe Phe Lys Tyr Phe Ser Asp Glu Ala Gln Ala Arg Ala Ala Phe Ser
380                 385                 390                 395 ctg att cag gag aac gag gtc ctc ttc acc atg tgc ttc atc ccc ctg       1371
Leu Ile Gln Glu Asn Glu Val Leu Phe Thr Met Cys Phe Ile Pro Leu
            400                 405                 410 gtc tgc tgg atc gtg tgc act gga ctg aaa cag cag atg gag agt ggc       1419
Val Cys Trp Ile Val Cys Thr Gly Leu Lys Gln Gln Met Glu Ser Gly
        415                 420                 425 aag agc ctt gcc cag aca tct aag acc acc acc gcg gtg tac gtc ttc       1467
Lys Ser Leu Ala Gln Thr Ser Lys Thr Thr Thr Ala Val Tyr Val Phe
    430                 435                 440 ttc ctt tcc agt ttg ctg cag ccc cgg gga ggg agc cag gag cac ggc       1515
Phe Leu Ser Ser Leu Leu Gln Pro Arg Gly Gly Ser Gln Glu His Gly
445                 450                 455 ctc tgc gcc cac ctc tgg ggg ctc tgc tct ttg gct gca gat gga atc       1563
Leu Cys Ala His Leu Trp Gly Leu Cys Ser Leu Ala Ala Asp Gly Ile
460                 465                 470                 475 tgg aac cag aaa atc ctg ttt gag gag tcc gac ctc agg aat cat gga       1611
Trp Asn Gln Lys Ile Leu Phe Glu Glu Ser Asp Leu Arg Asn His Gly
            480                 485                 490 ctg cag aag gcg gat gtg tct gct ttc ctg agg atg aac ctg ttc caa       1659
Leu Gln Lys Ala Asp Val Ser Ala Phe Leu Arg Met Asn Leu Phe Gln
        495                 500                 505 aag gaa gtg gac tgc gag aag ttc tac agc ttc atc cac atg act ttc       1707
Lys Glu Val Asp Cys Glu Lys Phe Tyr Ser Phe Ile His Met Thr Phe
    510                 515                 520 cag gag ttc ttt gcc gcc atg tac tac ctg ctg gaa gag gaa aag gaa       1755
Gln Glu Phe Phe Ala Ala Met Tyr Tyr Leu Leu Glu Glu Glu Lys Glu
525                 530                 535 gga agg acg aac gtt cca ggg agt cgt ttg aag ctt ccc agc cga gac       1803
Gly Arg Thr Asn Val Pro Gly Ser Arg Leu Lys Leu Pro Ser Arg Asp
540                 545                 550                 555 gtg aca gtc ctt ctg gaa aac tat ggc aaa ttc gaa aag ggg tat ttg       1851
Val Thr Val Leu Leu Glu Asn Tyr Gly Lys Phe Glu Lys Gly Tyr Leu
            560                 565                 570 att ttt gtt gta cgt ttc ctc ttt ggc ctg gta aac cag gag agg acc       1899
Ile Phe Val Val Arg Phe Leu Phe Gly Leu Val Asn Gln Glu Arg Thr
        575                 580                 585 tcc tac ttg gag aag aaa tta agt tgc aag atc tct cag caa atc agg       1947
Ser Tyr Leu Glu Lys Lys Leu Ser Cys Lys Ile Ser Gln Gln Ile Arg
    590                 595                 600 ctg gag ctg ctg aaa tgg att gaa gtg aaa gcc aaa gct aaa aag ctg       1995
Leu Glu Leu Leu Lys Trp Ile Glu Val Lys Ala Lys Ala Lys Lys Leu
605                 610                 615 cag atc cag ccc agc cag ctg gaa ttg ttc tac tgt ttg tac gag atg       2043
Gln Ile Gln Pro Ser Gln Leu Glu Leu Phe Tyr Cys Leu Tyr Glu Met
620                 625                 630                 635 cag gag gag gac ttc gtg caa agg gcc atg gac tat ttc ccc aag att       2091
Gln Glu Glu Asp Phe Val Gln Arg Ala Met Asp Tyr Phe Pro Lys Ile
            640                 645                 650 gag atc aat ctc tcc acc aga atg gac cac atg gtt tct tcc ttt tgc       2139
Glu Ile Asn Leu Ser Thr Arg Met Asp His Met Val Ser Ser Phe Cys
        655                 660                 665 att gag aac tgt cat cgg gtg gag tca ctg tcc ctg ggg ttt ctc cat       2187
Ile Glu Asn Cys His Arg Val Glu Ser Leu Ser Leu Gly Phe Leu His
    670                 675                 680 aac atg ccc aag gag gaa gag gag gag gaa aag gaa ggc cga cac ctt       2235
```

```
                                                                      -continued Asn Met Pro Lys Glu Glu Glu Glu Glu Lys Glu Gly Arg His Leu
    685                 690                 695 gat atg gtg cag tgt gtc ctc cca agc tcc tct cat gct gcc tgt tct        2283
Asp Met Val Gln Cys Val Leu Pro Ser Ser Ser His Ala Ala Cys Ser
700                 705                 710                 715 cat gga ttg gtg aac agc cac ctc act tcc agt ttt tgc cgg ggc ctc        2331
His Gly Leu Val Asn Ser His Leu Thr Ser Ser Phe Cys Arg Gly Leu
                720                 725                 730 ttt tca gtt ctg agc acc agc cag agt cta act gaa ttg gac ctc agt        2379
Phe Ser Val Leu Ser Thr Ser Gln Ser Leu Thr Glu Leu Asp Leu Ser
            735                 740                 745 gac aat tct ctg ggg gac cca ggg atg aga gtg ttg tgt gaa acg ctc        2427
Asp Asn Ser Leu Gly Asp Pro Gly Met Arg Val Leu Cys Glu Thr Leu
        750                 755                 760 cag cat cct ggc tgt aac att cgg aga ttg tgg ttg ggg cgc tgt ggc        2475
Gln His Pro Gly Cys Asn Ile Arg Arg Leu Trp Leu Gly Arg Cys Gly
    765                 770                 775 ctc tcg cat gag tgc tgc ttc gac atc tcc ttg gtc ctc agc agc aac        2523
Leu Ser His Glu Cys Cys Phe Asp Ile Ser Leu Val Leu Ser Ser Asn
780                 785                 790                 795 cag aag ctg gtg gag ctg gac ctg agt gac aac gcc ctc ggt gac ttc        2571
Gln Lys Leu Val Glu Leu Asp Leu Ser Asp Asn Ala Leu Gly Asp Phe
                800                 805                 810 gga atc aga ctt ctg tgt gtg gga ctg aag cac ctg ttg tgc aat ctg        2619
Gly Ile Arg Leu Leu Cys Val Gly Leu Lys His Leu Leu Cys Asn Leu
            815                 820                 825 aag aag ctc tgg ttg gtc agc tgc tgc ctc aca tca gca tgt tgt cag        2667
Lys Lys Leu Trp Leu Val Ser Cys Cys Leu Thr Ser Ala Cys Cys Gln
        830                 835                 840 gat ctt gca tca gta ttg agc acc agc cat tcc ctg acc aga ctc tat        2715
Asp Leu Ala Ser Val Leu Ser Thr Ser His Ser Leu Thr Arg Leu Tyr
    845                 850                 855 gtg ggg gag aat gcc ttg gga gac tca gga gtc gca att tta tgt gaa        2763
Val Gly Glu Asn Ala Leu Gly Asp Ser Gly Val Ala Ile Leu Cys Glu
860                 865                 870                 875 aaa gcc aag aat cca cag tgt aac ctg cag aaa ctg ggg ttg gtg aat        2811
Lys Ala Lys Asn Pro Gln Cys Asn Leu Gln Lys Leu Gly Leu Val Asn
                880                 885                 890 tct ggc ctt acg tca gtc tgt tgt tca gct ttg tcc tcg gta ctc agc        2859
Ser Gly Leu Thr Ser Val Cys Cys Ser Ala Leu Ser Ser Val Leu Ser
            895                 900                 905 act aat cag aat ctc acg cac ctt tac ctg cga ggc aac act ctc gga        2907
Thr Asn Gln Asn Leu Thr His Leu Tyr Leu Arg Gly Asn Thr Leu Gly
        910                 915                 920 gac aag ggg atc aaa cta ctc tgt gag gga ctc ttg cac ccc gac tgc        2955
Asp Lys Gly Ile Lys Leu Leu Cys Glu Gly Leu Leu His Pro Asp Cys
    925                 930                 935 aag ctt cag gtg ttg gaa tta gac aac tgc aac ctc acg tca cac tgc        3003
Lys Leu Gln Val Leu Glu Leu Asp Asn Cys Asn Leu Thr Ser His Cys
940                 945                 950                 955 tgc tgg gat ctt tcc aca ctt ctg acc tcc agc cag agc ctg cga aag        3051
Cys Trp Asp Leu Ser Thr Leu Leu Thr Ser Ser Gln Ser Leu Arg Lys
                960                 965                 970 ctg agc ctg ggc aac aat gac ctg ggc gac ctg ggg gtc atg atg ttc        3099
Leu Ser Leu Gly Asn Asn Asp Leu Gly Asp Leu Gly Val Met Met Phe
            975                 980                 985 tgt gaa gtg ctg aaa cag cag agc tgc ctc ctg cag aac ctg ggg ttg        3147
Cys Glu Val Leu Lys Gln Gln Ser Cys Leu Leu Gln Asn Leu Gly Leu
        990                 995                 1000
```

-continued

```
tct gaa atg tat ttc aat tat gag aca aaa agt gcg tta gaa aca ctt    3195
Ser Glu Met Tyr Phe Asn Tyr Glu Thr Lys Ser Ala Leu Glu Thr Leu
    1005                1010                1015 caa gaa gaa aag cct gag ctg acc gtc gtc ttt gag cct tct tgg        3240
Gln Glu Glu Lys Pro Glu Leu Thr Val Val Phe Glu Pro Ser Trp
1020                1025                1030 taggagtgga acggggctg ccagacgcca gtgttctccg gtccctccag ctgggggccc   3300
tcaggtggag agagctgcga tccatccagg ccaagaccac agctctgtga tccttccggt   3360
ggagtgtcgg agaagagagc ttgccgacga tgccttcctg tgcagagctt gggcatctcc   3420
tttacgccag ggtgaggaag acaccaggac aatgacagca tcgggtgttg ttctcatcac   3480
agcgcctcag ttagaggatg ttcctcttgg tgacctcatg taattagctc attcaataaa   3540
gcactttctt tattttctc ttctctgtct aactttcttt ttcctatctt ttttttcttct   3600 ttgttctgtt tacttttgct catatcatca ttcccgctaa ctttctatta actgaccata   3660
acacagaact agttgactat atattatgtt gaaattttat ggcagctatt tatttattta   3720 aatttttgt aatagttttg ttttctaata agaaaaatcc atgcttttg tagctggttg     3780 aaaattcagg aatatgtaaa acttttggt atttaattaa attgattcct tttcttaatt    3840
ttaaaaaaaa aaaaaaa                                                  3857
```

<210> SEQ ID NO 5
<211> LENGTH: 1034
<212> TYPE: PRT
<213> ORGANISM: Homo sapiens

<400> SEQUENCE: 5

```
Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
            20                  25                  30

Gln Lys Gly Cys Ile Pro Leu Pro Arg Gly Gln Thr Glu Lys Ala Asp
        35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser Asp Asn
                85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140

Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
    210                 215                 220
```

```
Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
                260                 265                 270

Leu Ile Met Ser Cys Cys Pro Asp Pro Asn Pro Ile His Lys Ile
        275                 280                 285

Val Arg Lys Pro Ser Arg Ile Leu Phe Leu Met Asp Gly Phe Asp Glu
        290                 295                 300

Leu Gln Gly Ala Phe Asp Glu His Ile Gly Pro Leu Cys Thr Asp Trp
305                 310                 315                 320

Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
                340                 345                 350

Leu Glu Lys Leu Gln His Leu Leu Asp His Pro Arg His Val Glu Ile
                355                 360                 365

Leu Gly Phe Ser Glu Ala Lys Arg Lys Glu Tyr Phe Phe Lys Tyr Phe
        370                 375                 380

Ser Asp Glu Ala Gln Ala Arg Ala Ala Phe Ser Leu Ile Gln Glu Asn
385                 390                 395                 400

Glu Val Leu Phe Thr Met Cys Phe Ile Pro Leu Val Cys Trp Ile Val
                405                 410                 415

Cys Thr Gly Leu Lys Gln Gln Met Glu Ser Gly Lys Ser Leu Ala Gln
                420                 425                 430

Thr Ser Lys Thr Thr Thr Ala Val Tyr Val Phe Phe Leu Ser Ser Leu
        435                 440                 445

Leu Gln Pro Arg Gly Gly Ser Gln Glu His Gly Leu Cys Ala His Leu
        450                 455                 460

Trp Gly Leu Cys Ser Leu Ala Ala Asp Gly Ile Trp Asn Gln Lys Ile
465                 470                 475                 480

Leu Phe Glu Glu Ser Asp Leu Arg Asn His Gly Leu Gln Lys Ala Asp
                485                 490                 495

Val Ser Ala Phe Leu Arg Met Asn Leu Phe Gln Lys Glu Val Asp Cys
                500                 505                 510

Glu Lys Phe Tyr Ser Phe Ile His Met Thr Phe Gln Glu Phe Phe Ala
        515                 520                 525

Ala Met Tyr Tyr Leu Leu Glu Glu Lys Glu Gly Arg Thr Asn Val
530                 535                 540

Pro Gly Ser Arg Leu Lys Leu Pro Ser Arg Asp Val Thr Val Leu Leu
545                 550                 555                 560

Glu Asn Tyr Gly Lys Phe Glu Lys Gly Tyr Leu Ile Phe Val Val Arg
                565                 570                 575

Phe Leu Phe Gly Leu Val Asn Gln Glu Arg Thr Ser Tyr Leu Glu Lys
        580                 585                 590

Lys Leu Ser Cys Lys Ile Ser Gln Gln Ile Arg Leu Glu Leu Leu Lys
        595                 600                 605

Trp Ile Glu Val Lys Ala Lys Ala Lys Lys Leu Gln Ile Gln Pro Ser
        610                 615                 620

Gln Leu Glu Leu Phe Tyr Cys Leu Tyr Glu Met Gln Glu Glu Asp Phe
625                 630                 635                 640
```

-continued

```
Val Gln Arg Ala Met Asp Tyr Phe Pro Lys Ile Glu Ile Asn Leu Ser
                645                 650                 655

Thr Arg Met Asp His Met Val Ser Ser Phe Cys Ile Glu Asn Cys His
            660                 665                 670

Arg Val Glu Ser Leu Ser Leu Gly Phe Leu His Asn Met Pro Lys Glu
        675                 680                 685

Glu Glu Glu Glu Glu Lys Glu Gly Arg His Leu Asp Met Val Gln Cys
    690                 695                 700

Val Leu Pro Ser Ser Ser His Ala Ala Cys Ser His Gly Leu Val Asn
705                 710                 715                 720

Ser His Leu Thr Ser Ser Phe Cys Arg Gly Leu Phe Ser Val Leu Ser
                725                 730                 735

Thr Ser Gln Ser Leu Thr Glu Leu Asp Leu Ser Asp Asn Ser Leu Gly
            740                 745                 750

Asp Pro Gly Met Arg Val Leu Cys Glu Thr Leu Gln His Pro Gly Cys
        755                 760                 765

Asn Ile Arg Arg Leu Trp Leu Gly Arg Cys Gly Leu Ser His Glu Cys
    770                 775                 780

Cys Phe Asp Ile Ser Leu Val Leu Ser Ser Asn Gln Lys Leu Val Glu
785                 790                 795                 800

Leu Asp Leu Ser Asp Asn Ala Leu Gly Asp Phe Gly Ile Arg Leu Leu
                805                 810                 815

Cys Val Gly Leu Lys His Leu Leu Cys Asn Leu Lys Lys Leu Trp Leu
            820                 825                 830

Val Ser Cys Cys Leu Thr Ser Ala Cys Cys Gln Asp Leu Ala Ser Val
        835                 840                 845

Leu Ser Thr Ser His Ser Leu Thr Arg Leu Tyr Val Gly Glu Asn Ala
    850                 855                 860

Leu Gly Asp Ser Gly Val Ala Ile Leu Cys Glu Lys Ala Lys Asn Pro
865                 870                 875                 880

Gln Cys Asn Leu Gln Lys Leu Gly Leu Val Asn Ser Gly Leu Thr Ser
                885                 890                 895

Val Cys Cys Ser Ala Leu Ser Ser Val Leu Ser Thr Asn Gln Asn Leu
            900                 905                 910

Thr His Leu Tyr Leu Arg Gly Asn Thr Leu Gly Asp Lys Gly Ile Lys
        915                 920                 925

Leu Leu Cys Glu Gly Leu Leu His Pro Asp Cys Lys Leu Gln Val Leu
    930                 935                 940

Glu Leu Asp Asn Cys Asn Leu Thr Ser His Cys Cys Trp Asp Leu Ser
945                 950                 955                 960

Thr Leu Leu Thr Ser Ser Gln Ser Leu Arg Lys Leu Ser Leu Gly Asn
                965                 970                 975

Asn Asp Leu Gly Asp Leu Gly Val Met Met Phe Cys Glu Val Leu Lys
            980                 985                 990

Gln Gln Ser Cys Leu Leu Gln Asn Leu Gly Leu Ser Glu Met Tyr Phe
        995                1000                1005

Asn Tyr Glu Thr Lys Ser Ala Leu Glu Thr Leu Gln Glu Glu Lys Pro
    1010                1015                1020

Glu Leu Thr Val Val Phe Glu Pro Ser Trp
1025                1030
```

<210> SEQ ID NO 6
<211> LENGTH: 3102
<212> TYPE: DNA

<213> ORGANISM: Homo sapiens

<400> SEQUENCE: 6

| | | | | | |
|---|---|---|---|---|---|
| atggcaagca | cccgctgcaa | gctggccagg | tacctggagg | acctggagga | tgtggacttg | 60 |
| aagaaattta | agatgcactt | agaggactat | cctccccaga | agggctgcat | cccctcccg | 120 |
| agggtcaga | cagagaaggc | agaccatgtg | gatctagcca | cgctaatgat | cgacttcaat | 180 |
| ggggaggaga | aggcgtgggc | catggccgtg | tggatcttcg | ctgcgatcaa | caggagagac | 240 |
| ctttatgaga | aagcaaaaag | agatgagccg | aagtggggtt | cagataatgc | acgtgtttcg | 300 |
| aatcccactg | tgatatgcca | ggaagacagc | attgaagagg | agtggatggg | tttactggag | 360 |
| tacctttcga | gaatctctat | ttgtaaaatg | aagaaagatt | accgtaagaa | gtacagaaag | 420 |
| tacgtgagaa | gcagattcca | gtgcattgaa | gacaggaatg | cccgtctggg | tgagagtgtg | 480 |
| agcctcaaca | aacgctacac | acgactgcgt | ctcatcaagg | agcaccggag | ccagcaggag | 540 |
| agggagcagg | agcttctggc | catcggcaag | accaagacgt | gtgagagccc | cgtgagtccc | 600 |
| attaagatgg | agttgctgtt | tgaccccgat | gatgagcatt | ctgagcctgt | gcacaccgtg | 660 |
| gtgttccagg | gggcggcagg | gattgggaaa | acaatcctgg | ccaggaagat | gatgttggac | 720 |
| tgggcatcgg | ggacactcta | ccaagacagg | tttgactatc | tgttctatat | ccactgtcgg | 780 |
| gaggtgagcc | ttgtgacaca | gaggagcctg | ggggacctga | tcatgagctg | ctgccccgac | 840 |
| ccaaacccac | ccatccacaa | gatcgtgaga | aaaccctcca | gaatcctctt | cctcatggac | 900 |
| ggcttcgatg | agctgcaagg | tgcctttgac | gagcacatag | accgctctg | cactgactgg | 960 |
| cagaaggccg | agcggggaga | cattctcctg | agcagcctca | tcagaaagaa | gctgcttccc | 1020 |
| gaggcctctc | tgctcatcac | cacgagacct | gtggccctgg | agaaactgca | gcacttgctg | 1080 |
| gaccatcctc | ggcatgtgga | gatcctgggt | ttctccgagg | ccaaaaggaa | agagtacttc | 1140 |
| ttcaagtact | ctctctgatga | ggcccaagcc | agggcagcct | tcagtctgat | tcaggagaac | 1200 |
| gaggtcctct | tcaccatgtg | cttcatcccc | ctggtctgct | ggatcgtgtg | cactggactg | 1260 |
| aaacagcaga | tggagagtgg | caagagcctt | gcccagacat | ctaagaccac | caccgcggtg | 1320 |
| tacgtcttct | tcctttccag | tttgctgcag | ccccggggag | ggagccagga | gcacggcctc | 1380 |
| tgcgcccacc | tctgggggct | ctgctctttg | gctgcagatg | gaatctggaa | ccagaaaatc | 1440 |
| ctgtttgagg | agtccgacct | caggaatcat | ggactgcaga | aggcggatgt | gtctgctttc | 1500 |
| ctgaggatga | acctgttcca | aaaggaagtg | gactgcgaga | gttctacag | cttcatccac | 1560 |
| atgactttcc | aggagttctt | tgccgccatg | tactacctgc | tggaagagga | aaaggaagga | 1620 |
| aggacgaacg | ttccagggag | tcgtttgaag | cttcccagcc | gagacgtgac | agtccttctg | 1680 |
| gaaaactatg | gcaaattcga | aaagggtat | ttgattttg | ttgtacgttt | cctctttggc | 1740 |
| ctggtaaacc | aggagaggac | ctcctacttg | gagaagaaat | taagttgcaa | gatctctcag | 1800 |
| caaatcaggc | tggagctgct | gaaatggatt | gaagtgaaag | ccaaagctaa | aaagctgcag | 1860 |
| atccagccca | gccagctgga | attgttctac | tgtttgtacg | agatgcagga | ggaggacttc | 1920 |
| gtgcaaaggg | ccatggacta | tttccccaag | attgagatca | atctctccac | cagaatggac | 1980 |
| cacatggttt | cttccttttg | cattgagaac | tgtcatcggg | tggagtcact | gtccctgggg | 2040 |
| tttctccata | acatgcccaa | ggaggaagag | gaggaggaaa | aggaaggccg | acaccttgat | 2100 |
| atggtgcagt | gtgtcctccc | aagctcctct | catgctgcct | gttctcatgg | attggtgaac | 2160 |
| agccaccctca | cttccagttt | tgccgggggc | ctcttttcag | ttctgagcac | cagccagagt | 2220 |
| ctaactgaat | tggacctcag | tgacaattct | ctgggggacc | cagggatgag | agtgttgtgt | 2280 |

-continued

```
gaaacgctcc agcatcctgg ctgtaacatt cggagattgt ggttggggcg ctgtggcctc   2340
tcgcatgagt gctgcttcga catctccttg gtcctcagca gcaaccagaa gctggtggag   2400
ctggacctga gtgacaacgc cctcggtgac ttcggaatca gacttctgtg tgtgggactg   2460
aagcacctgt tgtgcaatct gaagaagctc tggttggtca gctgctgcct cacatcagca   2520
tgttgtcagg atcttgcatc agtattgagc accagccatt ccctgaccag actctatgtg   2580
ggggagaatg ccttgggaga ctcaggagtc gcaattttat gtgaaaaagc caagaatcca   2640
cagtgtaacc tgcagaaact ggggttggtg aattctggcc ttacgtcagt ctgttgttca   2700
gctttgtcct cggtactcag cactaatcag aatctcacgc acctttacct gcgaggcaac   2760
actctcggag acaaggggat caaactactc tgtgagggac tcttgcaccc cgactgcaag   2820
cttcaggtgt tggaattaga caactgcaac ctcacgtcac actgctgctg ggatctttcc   2880
acacttctga cctccagcca gagcctgcga aagctgagcc tgggcaacaa tgacctgggc   2940
gacctggggg tcatgatgtt ctgtgaagtg ctgaaacagc agagctgcct cctgcagaac   3000
ctggggttgt ctgaaatgta tttcaattat gagacaaaaa gtgcgttaga aacacttcaa   3060
gaagaaaagc ctgagctgac cgtcgtcttt gagccttctt gg                       3102
```

<210> SEQ ID NO 7
<211> LENGTH: 77
<212> TYPE: PRT
<213> ORGANISM: Homo sapiens

<400> SEQUENCE: 7

Asp His Leu Leu Ser Thr Leu Glu Glu Leu Val Pro Tyr Asp Phe Glu
1               5                   10                  15

Lys Phe Lys Phe Lys Leu Gln Asn Thr Ser Val Gln Lys Glu His Ser
                20                  25                  30

Arg Ile Pro Arg Ser Gln Ile Gln Arg Ala Arg Pro Val Lys Met Ala
            35                  40                  45

Thr Leu Leu Val Thr Tyr Tyr Gly Glu Glu Tyr Ala Val Gln Leu Thr
        50                  55                  60

Leu Gln Val Leu Arg Ala Ile Asn Gln Arg Leu Leu Ala
65                  70                  75

<210> SEQ ID NO 8
<211> LENGTH: 77
<212> TYPE: PRT
<213> ORGANISM: Homo sapiens

<400> SEQUENCE: 8

Asp Ala Ile Leu Asp Ala Leu Glu Asn Leu Thr Ala Glu Glu Leu Lys
1               5                   10                  15

Lys Phe Lys Leu Lys Leu Leu Ser Val Pro Leu Arg Glu Gly Tyr Gly
                20                  25                  30

Arg Ile Pro Arg Gly Ala Leu Leu Ser Met Asp Ala Leu Asp Leu Thr
            35                  40                  45

Asp Lys Leu Val Ser Phe Tyr Leu Glu Thr Tyr Gly Ala Glu Leu Thr
        50                  55                  60

Ala Asn Val Leu Arg Asp Met Gly Leu Gln Glu Met Ala
65                  70                  75

<210> SEQ ID NO 9
<211> LENGTH: 77
<212> TYPE: PRT

<213> ORGANISM: Homo sapiens

<400> SEQUENCE: 9

Gly Arg Leu Ala Cys Tyr Leu Glu Phe Leu Lys Lys Glu Glu Leu Lys
1               5                   10                  15
Glu Phe Gln Leu Leu Ala Asn Lys Ala His Ser Arg Ser Ser Ser
            20                  25                  30
Gly Glu Thr Pro Ala Gln Pro Glu Lys Thr Ser Gly Met Glu Val Ala
            35                  40                  45
Ser Tyr Leu Val Ala Gln Tyr Gly Glu Gln Arg Ala Trp Asp Leu Ala
50                  55                  60
Leu His Thr Trp Glu Gln Met Gly Leu Arg Ser Leu Cys
65                  70                  75

<210> SEQ ID NO 10
<211> LENGTH: 77
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(77)
<223> OTHER INFORMATION: Xaa = Any Amino Acid

<400> SEQUENCE: 10

Asp Xaa Leu Leu Xaa Xaa Leu Glu Xaa Leu Xaa Xaa Glu Glu Leu Lys
1               5                   10                  15
Lys Phe Lys Leu Leu Leu Xaa Asn Xaa Ser Xaa Xaa Xaa Glu Xaa Ser
            20                  25                  30
Arg Ile Pro Arg Xaa Gln Xaa Xaa Lys Ala Asp Gly Xaa Xaa Leu Ala
            35                  40                  45
Xaa Xaa Leu Val Thr Xaa Tyr Gly Glu Xaa Tyr Ala Val Glu Leu Ala
50                  55                  60
Leu Gln Val Leu Glu Xaa Met Gly Leu Arg Xaa Leu Ala
65                  70                  75

<210> SEQ ID NO 11
<211> LENGTH: 77
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(77)
<223> OTHER INFORMATION: Xaa = Any Amino Acid

<400> SEQUENCE: 11

Asp Xaa Leu Ala Xaa Tyr Leu Glu Xaa Leu Xaa Xaa Glu Glu Leu Lys
1               5                   10                  15
Lys Phe Lys Leu Leu Leu Xaa Asn Xaa Ser Pro Gln Lys Gly Xaa Ser
            20                  25                  30
Arg Ile Pro Arg Gly Gln Xaa Glu Lys Ala Asp Gly Val Asp Leu Ala
            35                  40                  45
Thr Leu Leu Val Thr Phe Tyr Gly Glu Glu Tyr Ala Trp Ala Leu Ala
50                  55                  60
Leu Gln Val Leu Glu Ala Met Gly Leu Arg Asp Leu Ala
65                  70                  75

<210> SEQ ID NO 12

```
<211> LENGTH: 28
<212> TYPE: PRT
<213> ORGANISM: Artificial Sequence
<220> FEATURE:
<223> OTHER INFORMATION: Consensus sequence

<400> SEQUENCE: 12

Asn Pro Ser Leu Arg Glu Leu Asp Leu Ser Asn Asn Lys Leu Gly Asp
 1               5                  10                  15

Glu Gly Ala Arg Ala Leu Ala Glu Ala Leu Lys Ser
             20                  25

<210> SEQ ID NO 13
<211> LENGTH: 23
<212> TYPE: PRT
<213> ORGANISM: Artificial Sequence
<220> FEATURE:
<223> OTHER INFORMATION: Consensus sequence

<400> SEQUENCE: 13

Asn Leu Glu Glu Leu Asp Leu Ser Asn Asn Leu Thr Ser Leu Pro Pro
 1               5                  10                  15

Gly Leu Phe Ser Asn Leu Pro
             20

<210> SEQ ID NO 14
<211> LENGTH: 90
<212> TYPE: PRT
<213> ORGANISM: Homo sapiens

<400> SEQUENCE: 14

Met Ala Lys Thr Pro Ser Asp His Leu Leu Ser Thr Leu Glu Glu Leu
 1               5                  10                  15

Val Pro Tyr Asp Phe Glu Lys Phe Lys Phe Lys Leu Gln Asn Thr Ser
             20                  25                  30

Val Gln Lys Glu His Ser Arg Ile Pro Arg Ser Gln Ile Gln Arg Ala
         35                  40                  45

Arg Pro Val Lys Met Ala Thr Leu Leu Val Thr Tyr Tyr Gly Glu Glu
     50                  55                  60

Tyr Ala Val Gln Leu Thr Leu Gln Val Leu Arg Ala Ile Asn Gln Arg
65                  70                  75                  80

Leu Leu Ala Glu Glu Leu His Arg Ala Ala
                 85                  90

<210> SEQ ID NO 15
<211> LENGTH: 90
<212> TYPE: PRT
<213> ORGANISM: Homo sapiens

<400> SEQUENCE: 15

Met Ala Gly Gly Ala Trp Gly Arg Leu Ala Cys Tyr Leu Glu Phe Leu
 1               5                  10                  15

Lys Lys Glu Glu Leu Lys Glu Phe Gln Leu Leu Leu Ala Asn Lys Ala
             20                  25                  30

His Ser Arg Ser Ser Ser Gly Glu Thr Pro Ala Gln Pro Glu Lys Thr
         35                  40                  45

Ser Gly Met Glu Val Ala Ser Tyr Leu Val Ala Gln Tyr Gly Glu Gln
     50                  55                  60

Arg Ala Trp Asp Leu Ala Leu His Thr Trp Glu Gln Met Gly Leu Arg
65                  70                  75                  80
```

```
Ser Leu Cys Ala Gln Ala Gln Glu Gly Ala
                85                  90

<210> SEQ ID NO 16
<211> LENGTH: 89
<212> TYPE: PRT
<213> ORGANISM: Homo sapiens

<400> SEQUENCE: 16

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
                20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
        50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr
                85

<210> SEQ ID NO 17
<211> LENGTH: 89
<212> TYPE: PRT
<213> ORGANISM: Homo sapiens

<400> SEQUENCE: 17

Met Gly Thr Lys Arg Glu Ala Ile Leu Lys Val Leu Glu Asn Leu Thr
1               5                   10                  15

Pro Glu Glu Leu Lys Lys Phe Lys Met Lys Leu Gly Thr Val Pro Leu
                20                  25                  30

Arg Glu Gly Phe Glu Arg Ile Pro Arg Gly Ala Leu Gly Gln Leu Asp
            35                  40                  45

Ile Val Asp Leu Thr Asp Lys Leu Val Ala Ser Tyr Tyr Glu Asp Tyr
        50                  55                  60

Ala Ala Glu Leu Val Val Ala Val Leu Arg Asp Met Arg Met Leu Glu
65                  70                  75                  80

Glu Ala Ala Arg Leu Gln Arg Ala Ala
                85
```